United States Patent [19]

Reich et al.

[11] Patent Number: 5,714,518
[45] Date of Patent: Feb. 3, 1998

[54] HIV PROTEASE INHIBITORS AND METHODS OF MAKING THE SAME

[75] Inventors: Siegfried H. Reich, San Diego, Calif.; Mark J. Pino, Washington, D.C.; Dzuy T. Nguyen; Anthony J. Trippe, both of San Diego, Calif.

[73] Assignee: Agouron Pharmaceuticals, La Jolla, Calif.

[21] Appl. No.: 325,390

[22] PCT Filed: Jan. 18, 1994

[86] PCT No.: PCT/US94/00420

§ 371 Date: Oct. 27, 1994

§ 102(e) Date: Oct. 27, 1994

[87] PCT Pub. No.: WO94/15906

PCT Pub. Date: Jul. 21, 1994

[51] Int. Cl.$^6$ .......................... A61K 31/16; C07C 231/00; C07C 233/65
[52] U.S. Cl. .......................... 514/616; 514/307; 514/311; 514/354; 514/355; 514/357; 514/374; 514/400; 514/423; 514/478; 546/143; 546/146; 546/175; 546/314; 546/315; 546/316; 546/317; 546/334; 546/336; 546/337; 548/237; 548/338.1; 548/537; 560/13; 564/156; 564/158

[58] Field of Search .................. 564/158, 156; 514/616, 354, 355, 400, 307, 311, 357, 478, 423, 374; 546/314, 315, 316, 317, 146, 175, 143, 334, 336, 337; 548/338.1, 537, 237; 560/13

[56] References Cited

U.S. PATENT DOCUMENTS

| | | | |
|---|---|---|---|
| 2,895,991 | 7/1959 | Randall et al. | 260/558 |
| 3,947,516 | 3/1976 | Hunger et al. | 260/559 S |
| 4,064,349 | 12/1977 | Papenfuhs et al. | 560/56 |
| 4,299,845 | 11/1981 | Loebenberg et al. | 424/324 |
| 5,082,862 | 1/1992 | Tarnow et al. | 514/617 |
| 5,223,539 | 6/1993 | Nosal et al. | 514/622 |

*Primary Examiner*—Shailendra Kumar
*Attorney, Agent, or Firm*—Finnegan, Henderson, Farabow, Garrett & Dunner

[57] ABSTRACT

HIV protease inhibitors, obtainable by chemical synthesis, block the biological activity of the HIV protease enzyme, causing the replication of the HIV virus to terminate. These compounds, as well as pharmaceutical compositions that contain these compounds and possibly other anti-vital agents as ingredients, are thus suitable for the treatment of the HIV virus known to cause AIDS.

12 Claims, No Drawings

HIV PROTEASE INHIBITORS AND METHODS OF MAKING THE SAME

This invention was made with support of the United States of America Government under Grant No. GM 39599-05 awarded by the National Institute of General Medical Sciences, Public Health Service, Department of Health and Human Services. The U.S. Government has certain rights in this invention.

This application is a 371 PCT/US 94/00420, filed Jan. 18, 1994.

This invention relates to a novel series of non-peptidic chemical compounds which have been found to be useful as HIV protease inhibitors and to the use of such compounds as antiviral agents.

Acquired Immune Deficiency Syndrome (AIDS) is a relatively newly recognized disease or condition. AIDS causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell which plays a vital role in the body's immune system. HIV infection of these white blood cells depletes this white cell population. Eventually, the immune system is rendered inoperative and ineffective against various opportunistic diseases such as, among others, pneumocystic carini pneumonia, Karposis sarcoma, and cancer of the lymph system.

Although the exact mechanism of the formation and working of the HIV virus is not understood, identification of the virus has led to some progress in controlling the disease. For example, the drug azidothymidine (ART) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-tranlational processing of pre-peptides. This processing is accomplished by vitally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV vital agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

In accordance with this invention, there is provided a novel class of chemical compounds that have been found to inhibit and block the activity of the HIV protease, which halts the proliferation of HIV virus, pharmaceutical compositions containing these compounds, novel intermediates for compounds which inhibit and block the activity of the HIV protease, novel methods for making such compounds, and use of the compounds as inhibitors of the HIV.

Typical examples of carbocyclic ring systems represented by A' and B! shown above include, but are not limited to, phenyl, naphthyl, anthryl, and phenanthryl, either in their aromatic or fully or partially hydrogenated states. Typical heterocyclic ring systems represented by A' and B' include (1) 5-membered monocyclic ring groups such as thienyl, pyrrolyl, imidazolyl, pyrazolyl, furyl, isothiazolyl, furazanyl, isoxazolyl, thiazolyl and the like; (2) 6-membered monocyclic groups such as pyridyl, pyrazinyl, pyrimidinyl, pyridazinyl, triazinyl and the like; and (3) polycyclic heterocyclic ring groups, such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl and fully or partially hydrogenated analogs thereof.

The term "alkyl," as used herein refers to straight or branched chain groups, preferably having one to eight, more preferably one to six, carbon atoms. For example, "alkyl" may refer to methyl, ethyl, n-propyl, isopropyl, butyl, isobutyl, sec-butyl, tert-butyl, pentyl, isopentyl tert-pentyl, hexyl, isohexyl, and the like. Suitable substituents for the substituted alkyl and aryl groups used in the invention include the mercapto, thioether, nitro, amino, aryloxy, halogen, hydroxyl, and carbonyl groups as well as aryl, cycloalkyl and non-aryl heterocyclic groups.

The term "cycloalkyl" as used herein refers to groups, prefreably having three to seven, more preferably, three to six carbon atoms. Suitable cycloalkyls include, but are not limited to, cyclopropyl, cyclobutyl, cyclopentyl, cyclohexyl, cycloheptyl and the like.

The term "aryl" as used herein refers to both carbocyclic and heterocyclic, substituted or unsubstituted, aromatic residues. Accordingly, the term includes the types of substituents identified hereinabove as typical carbocyclic or heterocyclic ring systems which contain the requisite unsaturation to retain their aromatic character.

The terms "alkoxy" and "aryloxy" refer to groups as defined hereinabove as alkyl or aryl groups, as the case may be, which also carry an oxygen atom interposed between them and the substrate residue to which they are attached.

The "halogen" substituent according to the present invention may be a fluoro, chloro, bromo or iodo substituent.

Some compounds of the invention possess one or more asymmetrically substituted carbon atoms and therefore exist in racemic and optically active forms. The invention is intended to encompass the racemic forms of the compounds as well as any of the optically active forms thereof.

In the syntheses of the novel HIV inhibiting compounds of this invention, a large number of novel intermediate compounds has also been prepared. These novel intermediate compounds also form part of the invention. One class of such novel intermediates are compounds of the formula VI

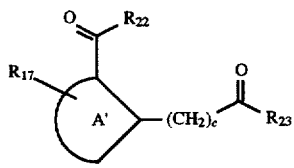

wherein:

c is 0, 1, or 2;

A' is selected from carbocyclic or heterocyclic, aromatic, saturated or partially saturated 5, 6 or 7 member rings which can be further substituted;

$R_{17}$ is selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{17}$ can form a fused ring structure with A';

$R'_1$ and $R'_2$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ can form a ring with the nitrogen atom to which they are attached;

$R_{22}$ is a substituted or unsubstituted amino group or an alkoxy group;

$R_{23}$ is hydrogen, hydroxyl, a substituted or unsubstituted amino group, or a group of the formula VII

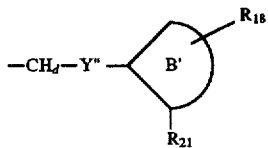

wherein:

d is 0, 1, or 2;

when d is 2, Y" is a substituted or unsubstituted amino group, oxygen, sulphur, or —$CH_2$—;

when d is 1, Y" is —CH=; —C=;

when d is 0, Y" is

B' is selected from carbocyclic or heterocyclic, aromatic, saturated or partially saturated 5, 6 or 7 member rings which can be further substituted;

$R_{18}$ is selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{18}$ can form a fused ring structure with B';

and $R_{21}$ is (1) amino, (2) nitro or (3) a group convertible to the group of the formula V,

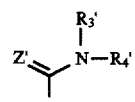

wherein

Z' is oxygen or sulphur; and $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_3$ and $R'_4$ can form a ring with the nitrogen atom to which they are attached.

The novel compounds of this invention can be prepared by a number of synthetic routes. A preferred synthesis comprises the following reaction sequence A in which all variable groups and substituents are as previously defined except the groups $R_{24}$ and $R'_{24}$ in compound X, which are individually selected from alkyl groups:

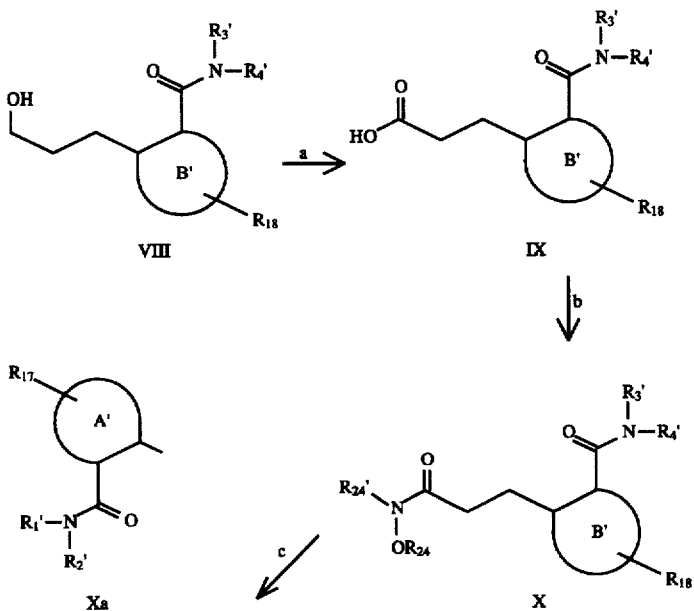

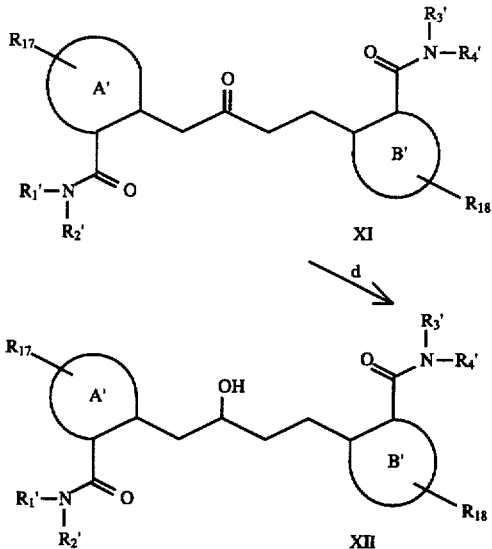

wherein:

a) the compound of the formula VIII is oxidized under conditions sufficient to obtain the compound of the formula IX;

b) the compound of the formula IX is reacted with an alkyl alkoxylamine under conditions sufficient to obtain the compound of the formula X;

c) the compound of the formula X is reacted with the compound of the formula Xa under conditions sufficient to obtain the compound of the formula XI; and d) the compound of the formula XI is reduced under conditions sufficient to obtain the compound of the formula XII.

All steps are preferably carried out in a suitable solvent.

In the first step of sequence A, compound VIII, prepared by known methods, is oxidized to the carboxylic acid IX. Oxidation can be carried out using conventional oxidizing agents such as e.g. chromium trioxide, pyridinium dichromate, under conditions conventionally known for carrying out such an oxidation, i.e. usually acid conditions and moderate temperatures.

Alternatively, the oxidation can be carried out in basic medium, which results in formation of the aldehyde corresponding to the carboxylic acid IX.

If either $R'_1$ or $R'_2$ is a hydroxyalkyl group, it is highly preferred that the hydroxyl group be protected from oxidation during this first step. Such protection is readily provided by reacting the hydroxyl group with conventional protecting groups such as e.g. an alkyl or aryl substituted silane, benzyl, or substituted benzyl group, prior to the oxidation step. The protecting group is readily removed as a final (additional) step in the sequence.

In the second step of this sequence, the carboxylic acid IX is reacted with a secondary amine to form the carboxylic acid amide X. Preferred secondary amines include N-alkyl-O-alkyl hydroxylamines, which are readily reacted in subsequent steps. The reaction can be carried out in the presence of a base, such as a lower alkyl tertiary amine, and a suitable coupling reagent, such as DCC, defined later herein, BOP, defined later herein, and EDC (1-(3-dimethylaminopropyl) -3-ethylcarbodiimide hydrochloride, preferably at moderate temperatures, e.g. about room temperature. The preferred secondary amine is N-methyl O-methyl hydroxylamine while the preferred base is a tertiary amine, such as triethylamine or diisopropyl ethylamine.

In the third step of this sequence, the carboxylic acid amide X is coupled with a compound of formula Xa to form the ketone of formula XI. This reaction can be carried out at low temperatures, i.e about −60° to −85°, preferably about −78° C., in the presence of an alkyl lithium compound and an amine. When one or more of $R'_1$, $R'_2$, $R'_3$ and $R'_4$ is hydrogen, the preferred amine is tetramethyl ethylene diamine (TMEDA). When all of $R'_1$, $R'_2$, $R'_3$ and $R'_4$ are other than hydrogen, the preferred amine is a secondary dialkyl amine, such as diisopropyl amine. In each case, the preferred alkyl lithium compound is a butyl lithium, preferably s-butyl lithium.

In the fourth step of this sequence, the ketone of formula XI is reduced to the compound of formula XII. Reduction can be carried out with a reducing agent such as, e.g. $NaBH_4$ or $LiBH_4$. Reduction with $NaBH_4$ can be carried out at relatively low temperatures, i.e. about 0° C. to room temperature.

In the case where one or both of $R'_1$ and $R'_2$ is a hydroxylalkyl group, the reduction step is preferably followed by a fifth step, i.e. a deprotection step. The deprotection method to be used depends on the identity of the protecting group. In the case of the preferred alkyl or aryl silane protecting group, deprotection can be accomplished in the presence of fluoride ion, e.g., tetrabutyl ammonium fluoride. In the case of a benzyl protecting group, deprotection can be accomplished by hydrogenation over palladium.

Still other compounds can be prepared via reaction sequence E in which all variable groups and substituents are as previously defined except for "a", which is defined below:

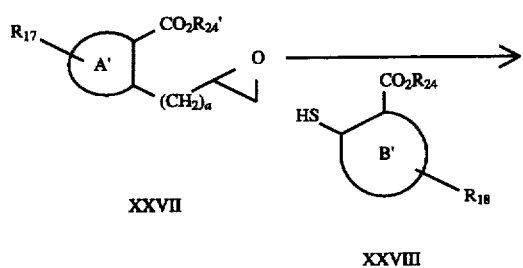

XXVII

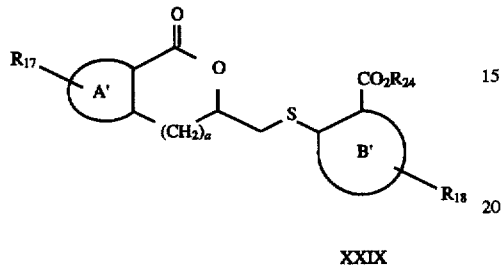

XXIX wherein the compound of the formula XXVII, wherein a is 0, 1 or 2 and R'$_{24}$ is an alkyl group, is reacted with a compound of the formula XXVIII under conditions sufficient to obtain the compound of the formula XXIX.

In reaction E, a compound of XXVII is reacted with a compound of formula XXVIII to form a compound of formula XXIX. The compound of formula XXIX can be reacted with an aminoaluminum dialkyl to open the lactone ring and form an amide.

The novel class of compounds according to this invention may be represented by

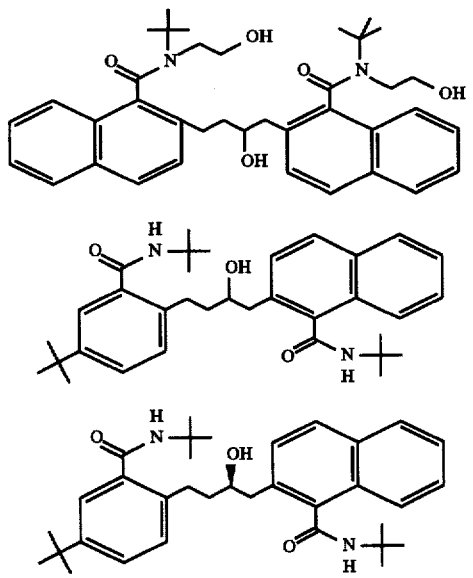

-continued

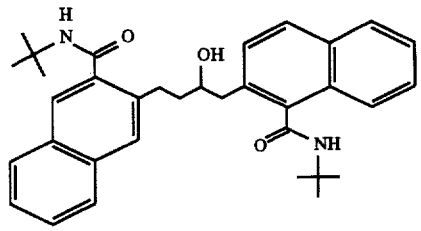

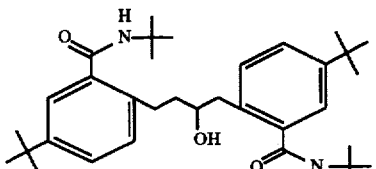

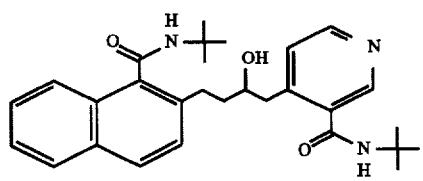

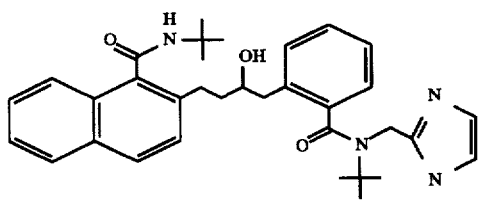

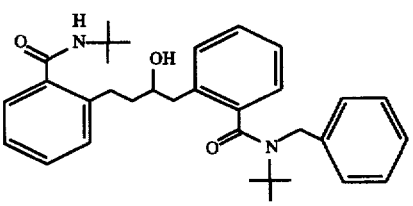

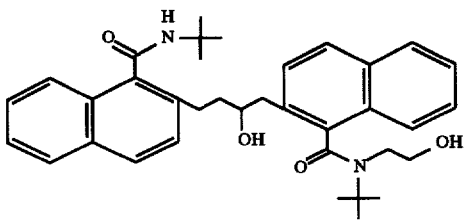

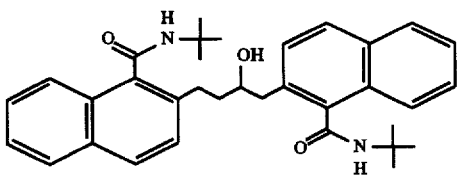

-continued
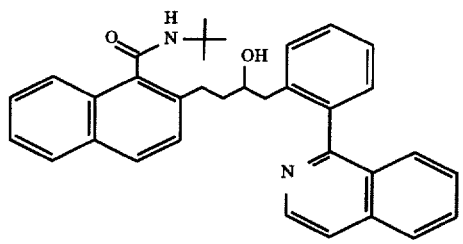
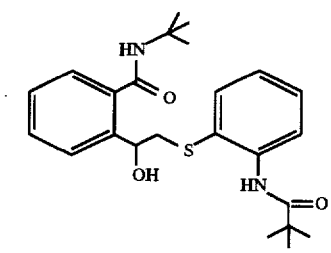
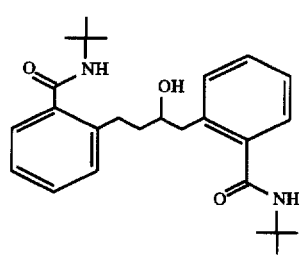
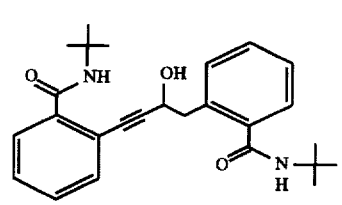
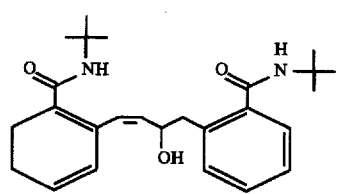
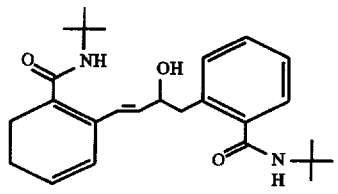
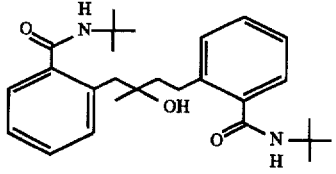
-continued
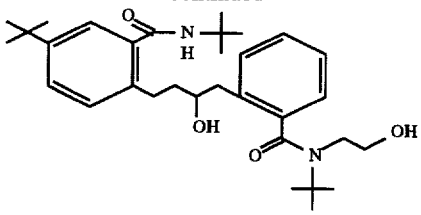
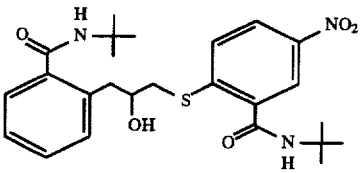
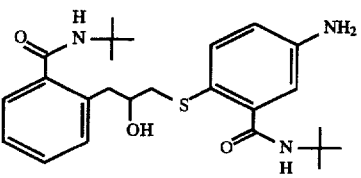
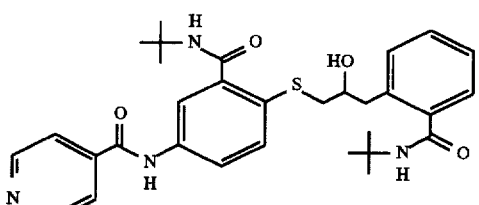
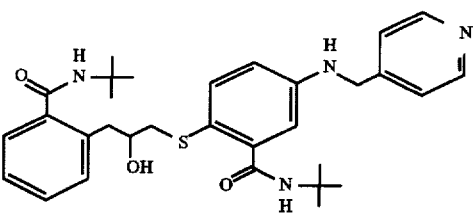
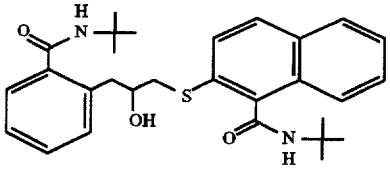
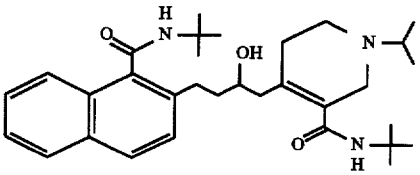
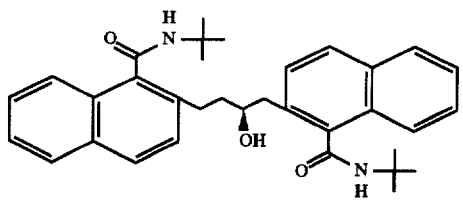

-continued

-continued

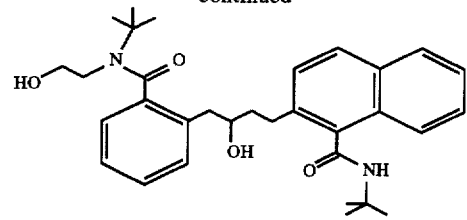
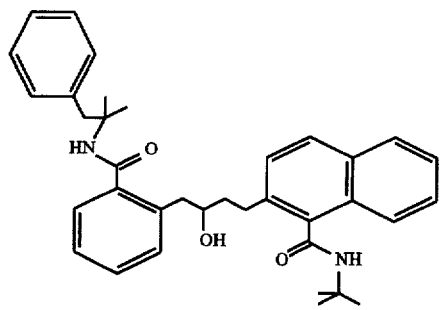
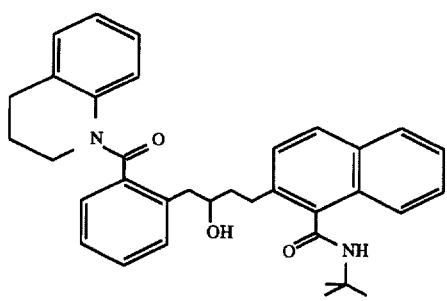
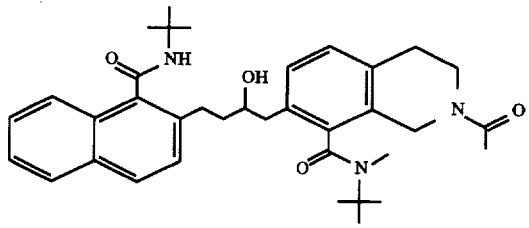
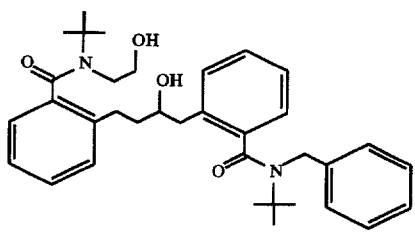

or a pharmaceutically acceptable salt thereof.

The compounds of this invention, as indicated hereinabove, are effective in inhibiting the activity of the HIV protease, which halts the proliferation of the HIV virus. A compound according to the invention may be active per se, or it may be a precursor which is converted in vivo to an active compound. Moreover, many of the compounds of the invention contain functional groups that are capable of forming salts. It is intended that the invention also include such pharmaceutically acceptable salts, e.g. carboxylic acid salts or quaternary salts.

The invention also includes compositions useful for inhibiting HIV protease which comprises (1) a compound selected from

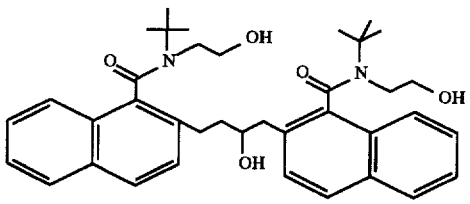
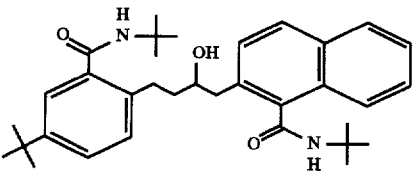
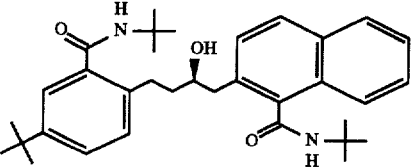
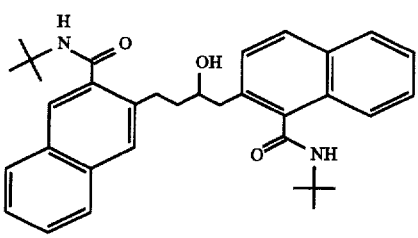
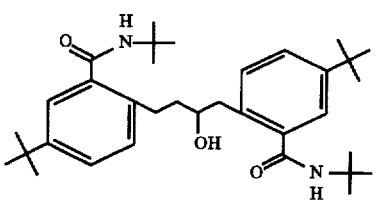
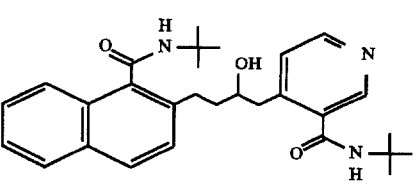
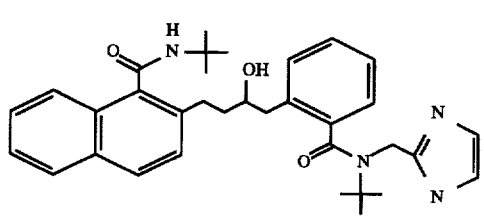
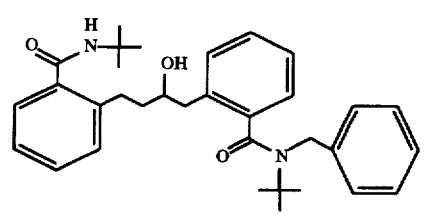

-continued
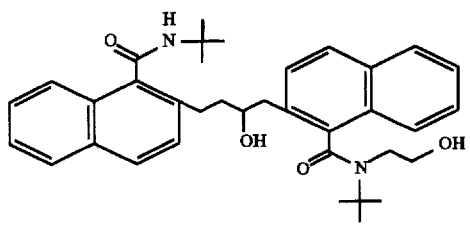
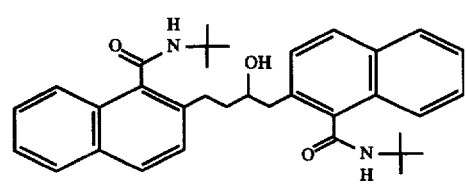
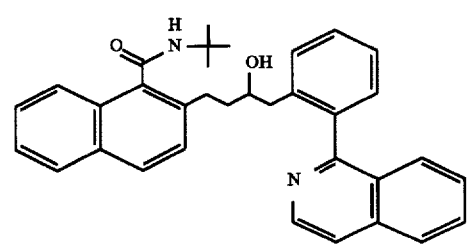
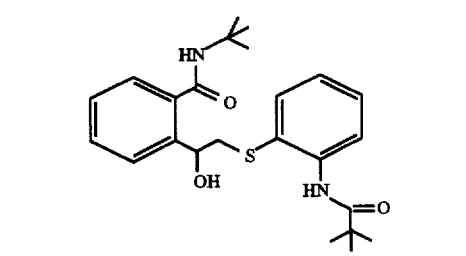
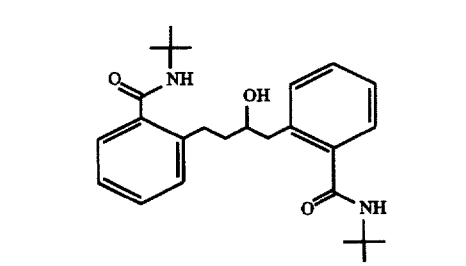
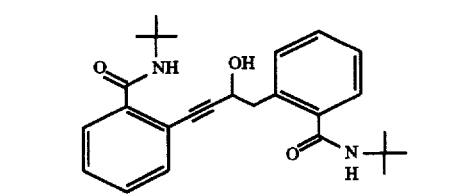
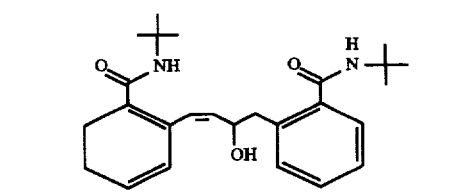
-continued
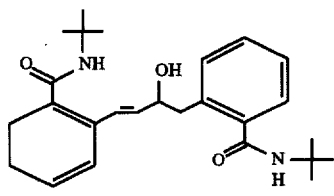
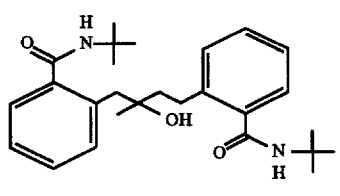
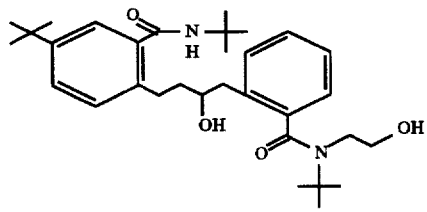
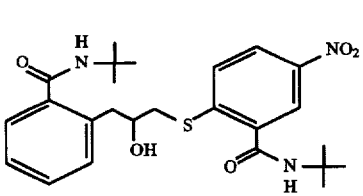
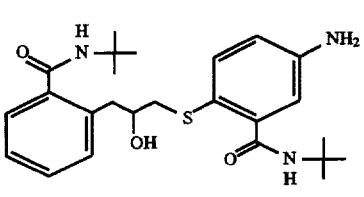
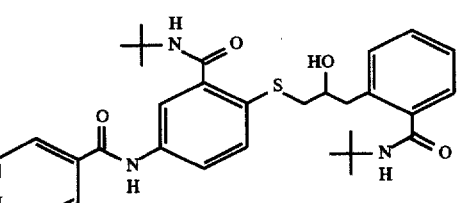
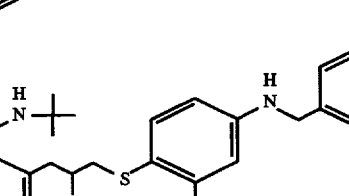
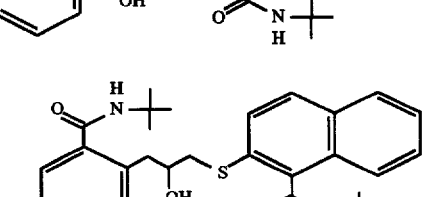
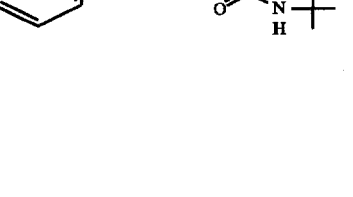

17
-continued
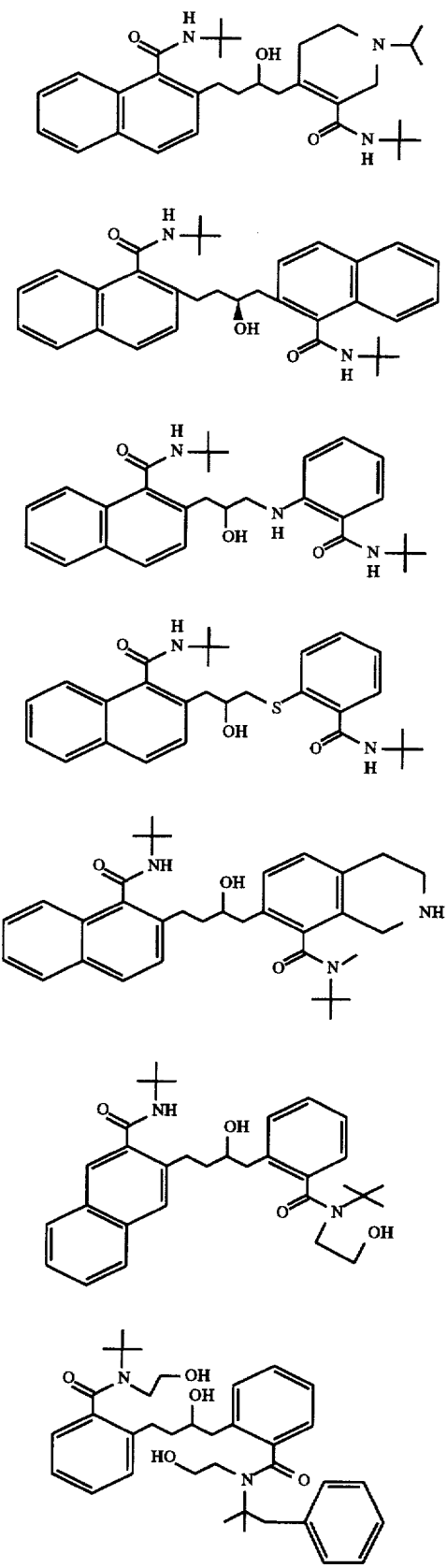
18
-continued
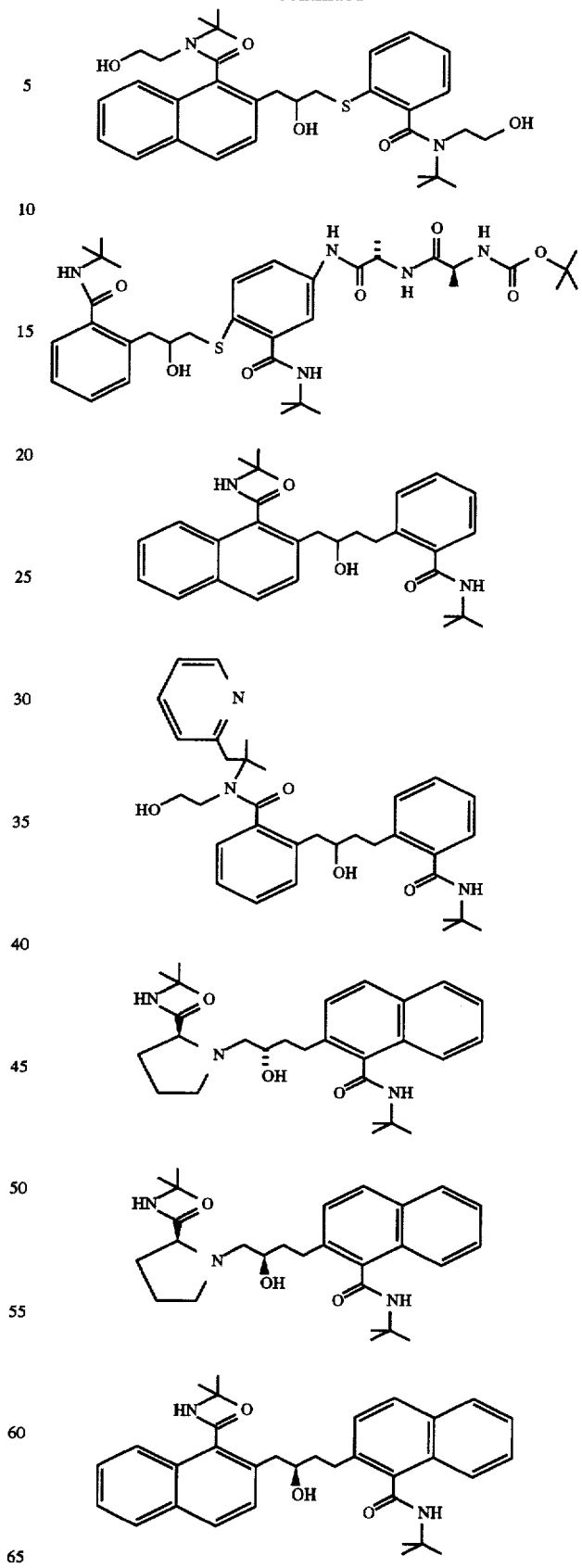

-continued

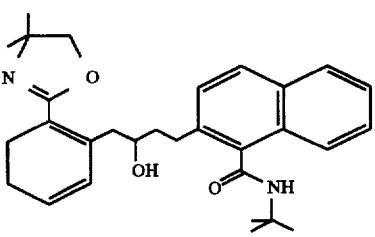
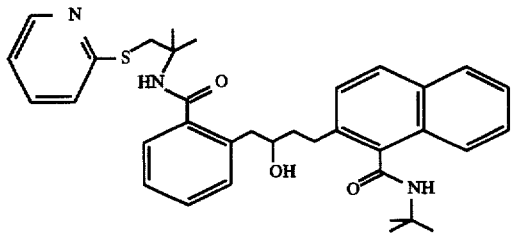
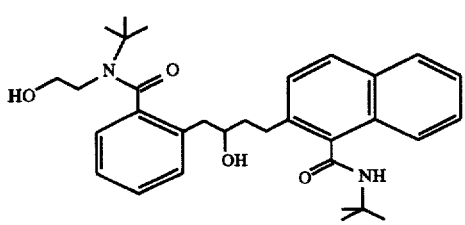
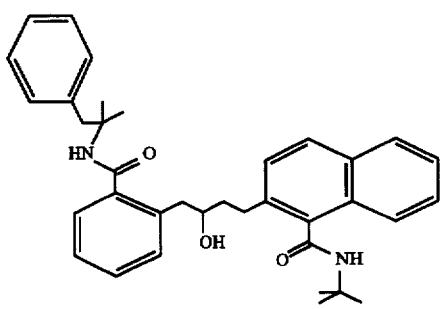
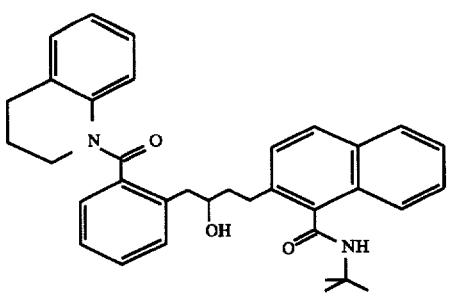
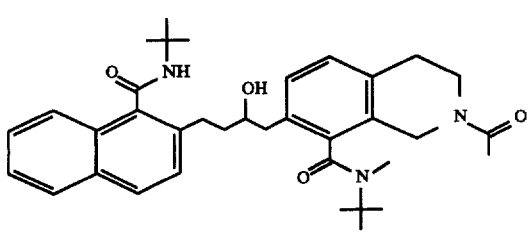

-continued

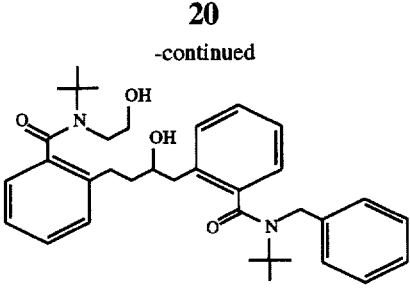

or a pharmaceutically acceptable salt thereof; and (2) a pharmaceutically acceptable carrier.

The compounds according to the invention, as well as the pharmaceutically acceptable salts thereof, can be incorporated into convenient dosage forms such as capsules, tablets, or injectable preparations. Solid or liquid pharmaceutically acceptable carriers can also be employed. Solid carriers can include starch, lactose, calcium sulphate dihydrate, terra alba, sucrose, talc, gelatin, agar, pectin, acacia, magnesium stearate and steric acid. Liquid carriers can include syrup, peanut oil, olive oil, saline solution and water.

The carrier or diluent can include prolonged release material, such as glyceryl monostearate or glyceryl distearate, alone or with wax. When a liquid carrier is used, the preparation may be in the form of a syrup, elixir, emulsion, soft gelatin capsule, sterile injectable liquid (e.g. solution) or a nonaqueous or aqueous liquid suspension.

The pharmaceutical preparations can be prepared following conventional techniques of the pharmaceutical chemist involving steps such as mixing, granulating, and compressing when necessary for tablet forms, or mixing, filling and dissolving the ingredient as appropriate to give the desired products for oral, parenteral, topical, intravaginal, intranasal, intrabronchial, intraocular, intraaural and rectal administration or by injection.

The compositions of the invention may further comprise one or more other compounds which are either HIV inhibitors, such as azidothymidine, or which perform a different pharmaceutically desirable function, such as, for example antibacterial, antifungal, antiparasitic, antiviral, antipsoriatic or anticoccicidal agents. Exemplary antibacterial agents include, for example, sulfonamides such as sulfamethoxazole, sulfadiazine, sulfameter or sulfadoxine.

The invention also covers the process for inhibiting the action of HIV virus which comprises administering to a host in recognized need of such treatment an effective amount of a compound selected from

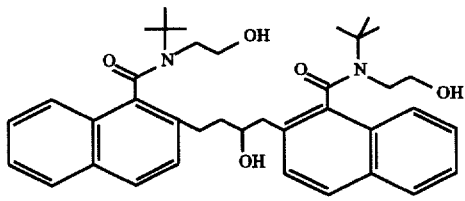
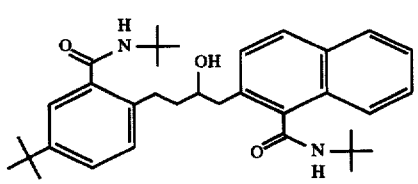

21
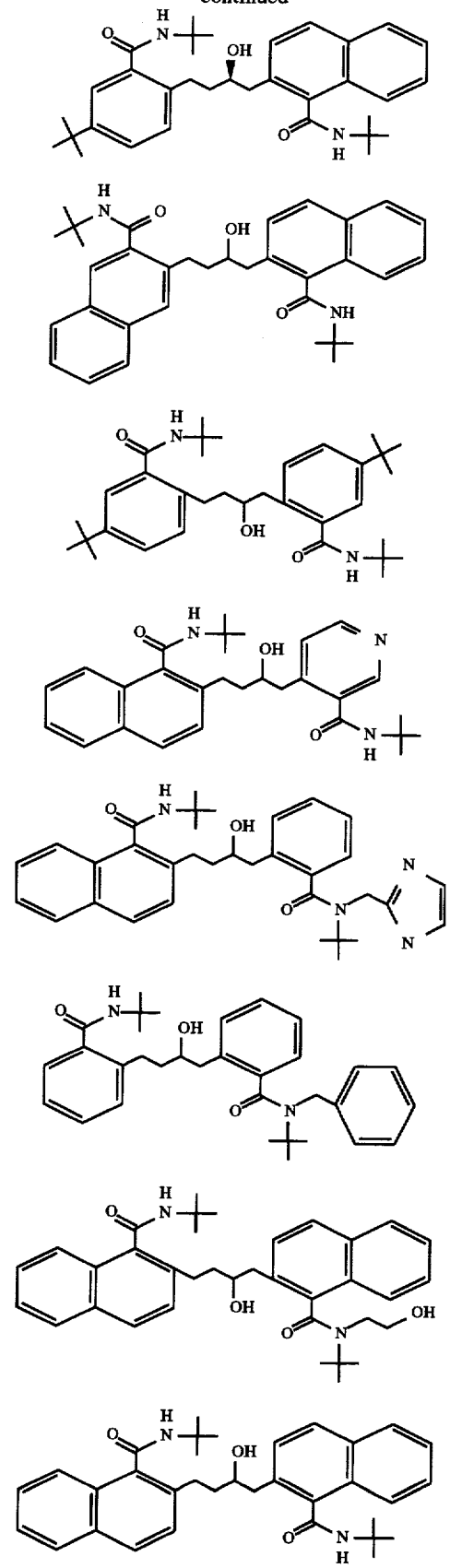
-continued
22
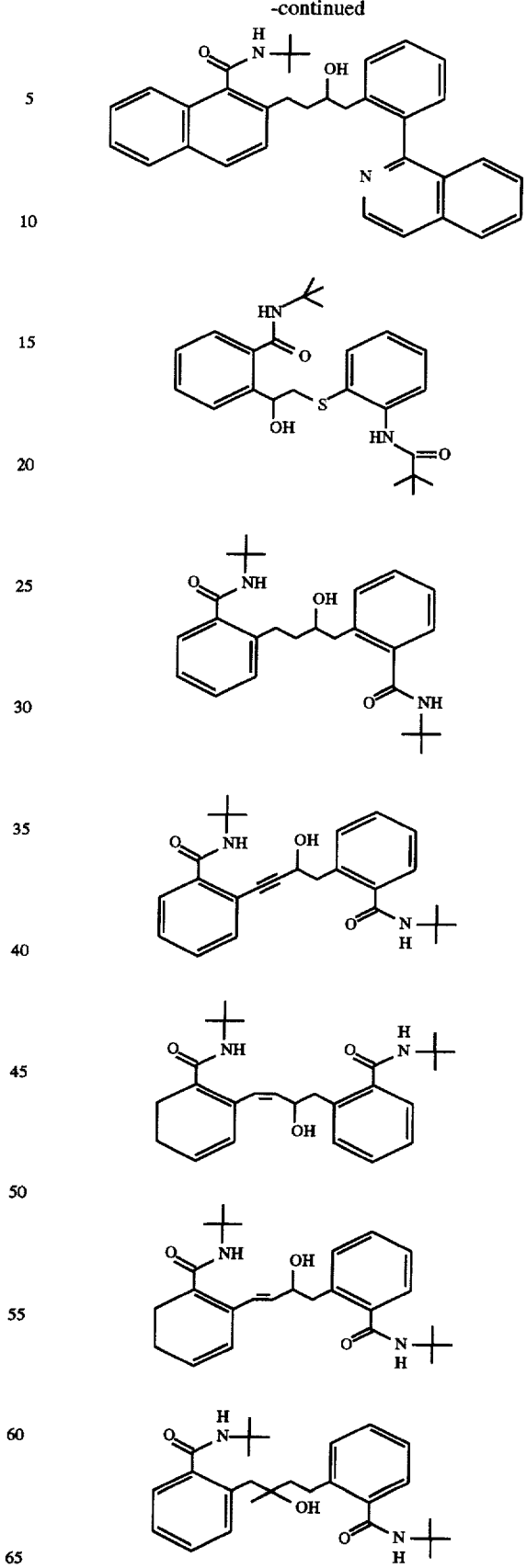
-continued

-continued
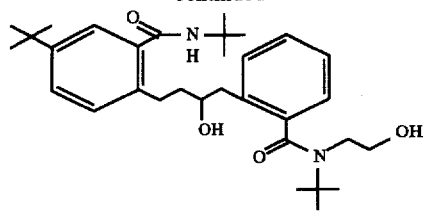
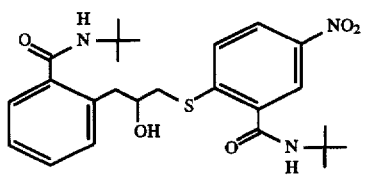
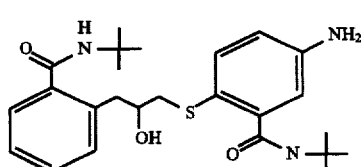
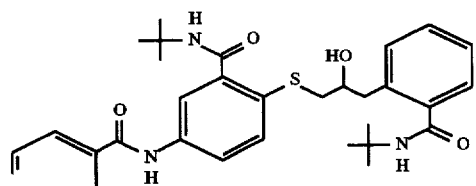
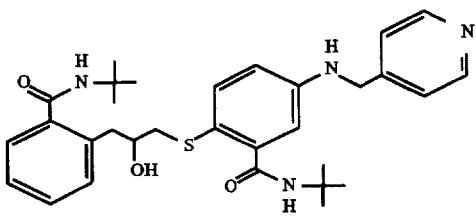
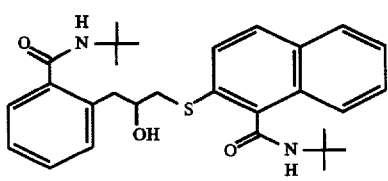
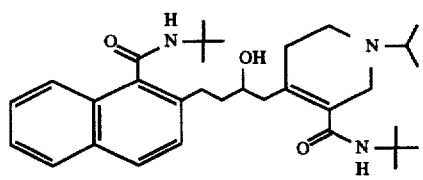
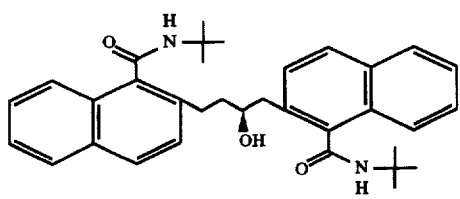
-continued
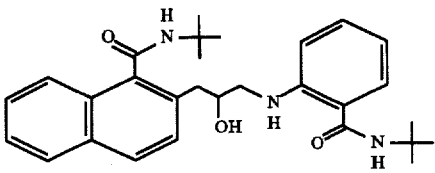
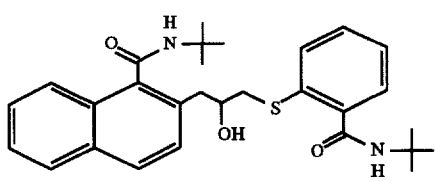
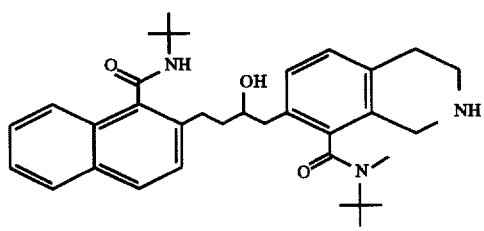
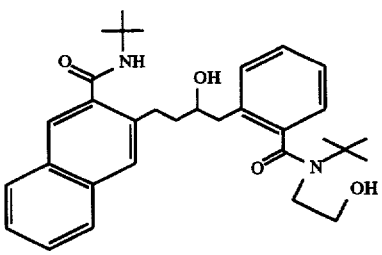
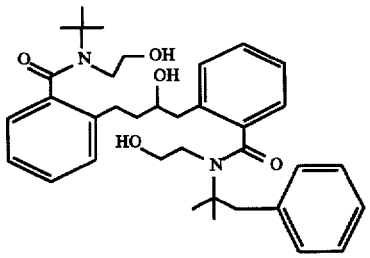
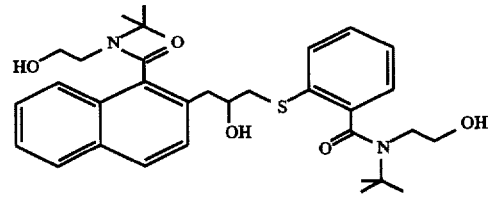
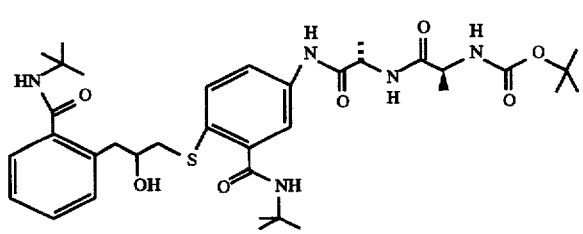

-continued

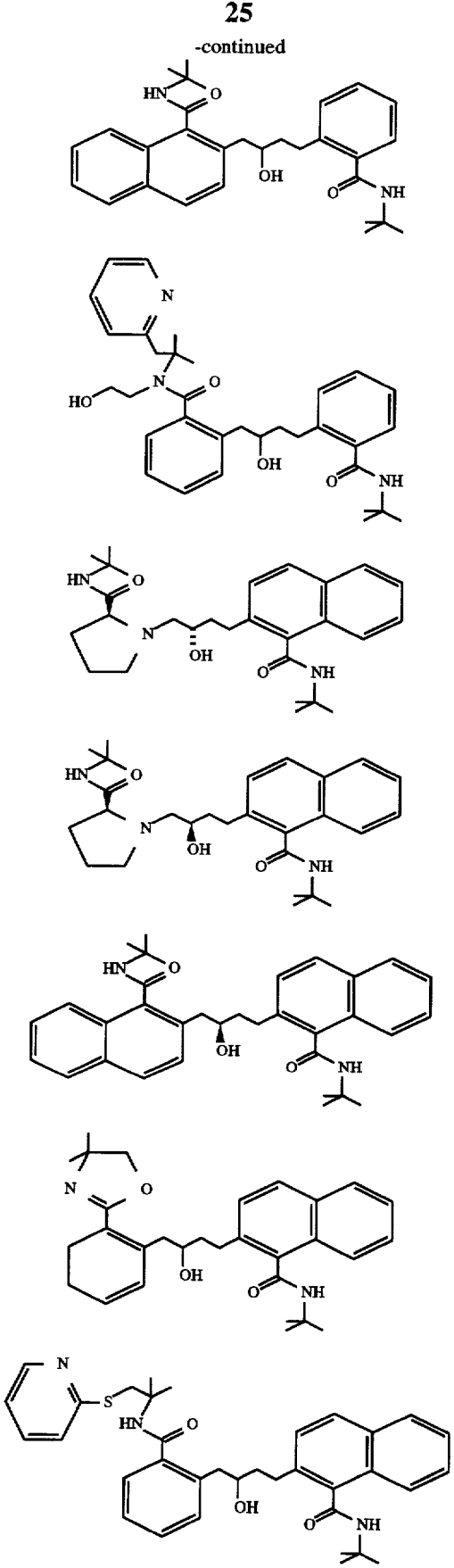

-continued

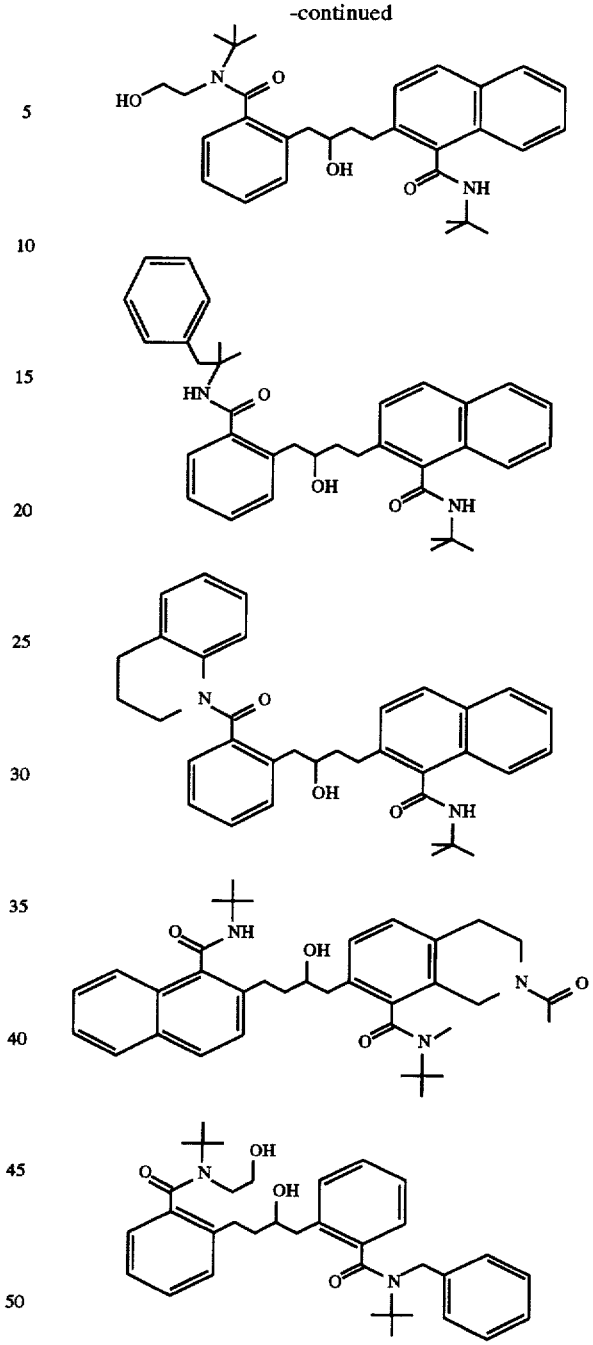

or a pharmaceutically acceptable salt thereof.

An exemplary daily dosage unit comprises an amount up to about one gram of active compound per kilogram of the host, preferably one half gram, more preferably 100 milligrams, and most preferably, about 50 milligrams or less per kilogram of the host weight. The selected dose may be administered to a patient in recognized need of treatment, by any known method of administrating the dose including topically as, for example, an ointment or cream; orally; rectally, for example, as a suppository; parenterally by injection; or continuously by intravaginal, intranasal, intrabronchial, intraaural or intraocular infusion.

Details and specific embodiments of these syntheses will be presented in the example hereinbelow. In these examples, the structures of all new compounds were confirmed by proton magnetic resonance spectroscopy, infrared spectroscopy, and either elemental microanalysis (C, H, and N to within 0.4%) or by high resolution mass spectrometry. Proton magnetic resonance spectra were determined using a General Electric QE-300 spectrometer operating at a field stength of 300 mHz.

Most of the examples consist of a sequence of syntheses proceeding from commercially available compounds through a series of intermediates to a final product corresponding to one of the specific compounds set forth above. Each of these steps has actually been carried out and each such intermediate has actually been prepared. However, it must be understood that when a step in a sequence refers to a compound from an earlier step, the physical specimen of that compound that was employed in that step may not be the same physical specimen of that compound that was actually prepared in the cited earlier step. For example, in step 7b of Example 7, the reaction of compound 7a with compound 4e is described. It is believed that although the compound actually reacted with compound 7a was identical in chemical structure to the compound 4e, it is possible that the compound actually reacted with compound 7a was not the same physical specimen of compound 4e as was prepared in Example 4. If the compound actually reacted with compound 7a was not the same physical specimen as compound 4e, it is believed that the compound actually reacted was prepared in the same way as the compound 4e.

EXAMPLE 1

Preparation of

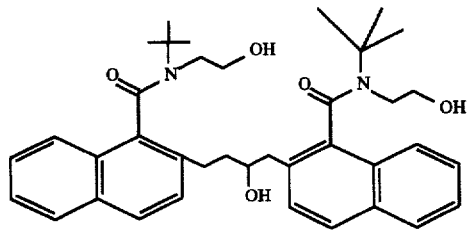

Step 1a

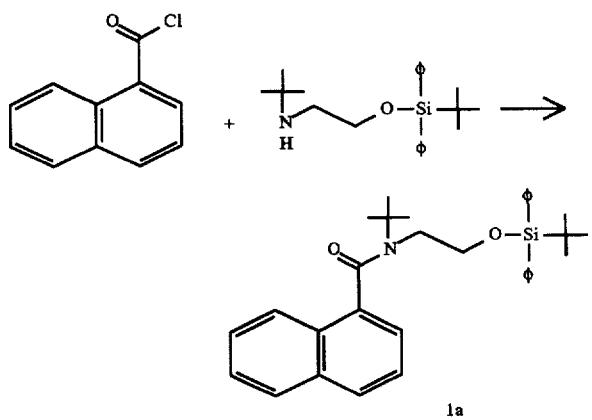

To a solution of 3.2 gm (31.5 mmol) of triethylamine and 11.2 gm (31.5 mmol) of N-(t-butyl)-N-hydroxyethyl (diphenyl, t-butyl-silyl) amine in 100 ml of THF at 0° C. was added 6.0 gm (31.5 mmol) of naphthoyl chloride. Within 5 minutes a white precipitate formed and settled out. The solution was allowed to warm to room temperature and was stirred for one hour. Monitoring by TLC indicated no residual amine was present. The reaction mix was poured into water and extracted with diethyl ether. The organic extracts were washed with brine and dried over $MgSO_4$.

The organic extract was filtered and solvent was removed under vacuum, yielding 17.15 gm of crude product. The crude product was purified by flash chromatography using 3 to 1 hexane/diethyl ether. 'HNMR confirmed the structure.

Step 1b

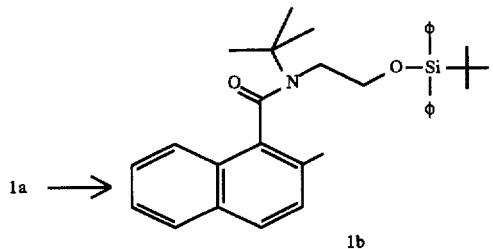

A solution of 4.5 gm (8.83 mmol) of compound 1a and 1.13 gm of TMEDA in 100 ml of THF was cooled to −78° C. in a dry/ice acetone bath. After 15 minutes 8.8 ml of a 1.1M solution of s-butyl lithium in cyclohexane was added dropwise. The clear solution became a light orange in color and was stirred at −78° C. for 1.5 hours. At this time 3.45 gm (24.3 mmol) of methyl iodide (filtered through basic alumina) was added rapidly to the solution. The reaction mass became a lighter orange in color and a white solid appeared. After 1 hour at −78° C., TLC indicated that some residual starting material remained. The reaction mixture was allowed to warm to room temperature and after 1 hour, was monitored again by TLC. At this point, no residual starting material remained. The reaction mixture was poured into diethyl ether, washed with water and then with brine, dried over $MgSO_4$ and filtered. The solvent was removed in vacuum yielding 17.15 gm of a light yellow oil. The oil was purified by flash chromatography using 2:1 hexane/ether. Fractions 14–25 were collected cleanly and the solvent was removed under vacuum. The structure of the product was confirmed by 'HNMR.

Step 1c

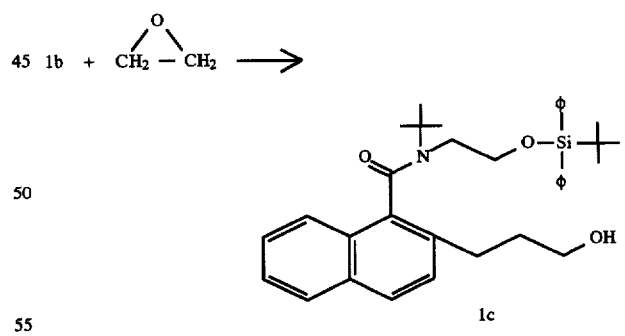

A solution of 2.36 gm (4.51 mmol) of compound 1b, 0.07 gm of diisopropylamine and 40 ml of THF was cooled to −78° C. and 4.72 ml of a 1.1M solution of s-butyl lithium in cyclohexane was slowly added. The resulting blood red solution was stirred for 1.5 hours at −78° C. at which time 0.6 gm (13.53 mmol) of ethylene oxide was added rapidly to the solution. After 15 minutes no color change was observed. The reaction was allowed to warm to 0° C. As the reaction warmed the solution became dark green and was stirred for 30 minutes at which time monitoring by TLC indicated that no residual starting material was present. The mass was poured into water, extracted with diethylether, washed with brine, dried over MgSO₄ and filtered. Solvent was removed under vacuum and the product purified by column chromatography using a 3:1 mixture of diethylether and hexane. Fractions 21–40 were collected cleanly and solvent was removed under vacuum. Yield was 3.43 gm. The structure of the product was confirmed by 'HNMR.

Step 1d

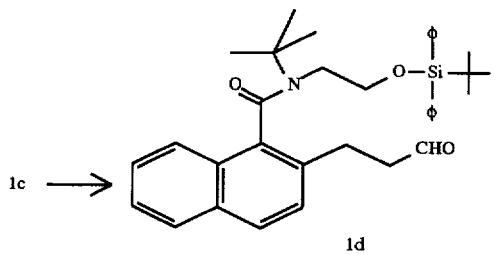

To a solution of 1.9 gm of pyridine in 30 ml of methylene chloride was added 1.2 gm of chromium trioxide at room temperature. The reddish solid partially dissolved into an orange solution with a brown solid residue. After 10 minutes a solution of 1.14 gm (2.0 mmol) of compound 1c in 6 ml of methylene chloride was added, dropwise. After 15 minutes a small amount was syringed into 1N HCL extracted with diethylether and monitored by TLC which indicated that no starting material remained. The mixture was poured into diethylether, washed twice with NaOH, then with 1N HCL, then with saturated NaHCO₃, and finally with brine. The crude product was filtered and the solvent was removed under vacuum. This crude product (1.5 gm) was purified by flash chromatography using a 2:1 ether/hexane solution as eluant. Fractions 36–45 were collected and solvent was removed under vacuum. The structure was proven by 'HNMR.

Step 1e

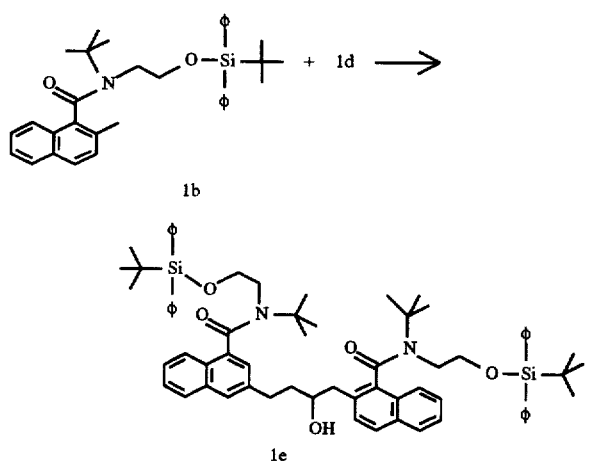

A solution of 0.176 gm (0.34 mmol) of compound 1b, 0.0052 gm of diisopropylamine and 4 ml of THF was cooled to −78° C. and 355.5 microliters of a 1.1M solution of s-butyl lithium in cyclohexane was added, dropwise. A blood red solution was produced and was allowed to stir for one hour at −78° C. At the end of this hour a solution of 0.192 gm (0.34 mmol) of compound in 1 ml of THF was added in a single addition. The blood red color turned into a light yellow. After 15 minutes, TLC indicated that most of the starting materials had been consumed. The reaction mass was poured into ether, washed with Water and brine and then dried over MgSO₄. The dried mixture was filtered and solvent was removed under vacuum, yielding a clear oil. This oil was subjected to column chromatography using a 1:1 ether/hexane solution.

Fractions 23–35 were a mixture of the compound 1d and product. These were resubmitted to chromatography and purified, yielding 0.041 gm of compound 1e. Structure was confirmed by NMR.

Step 1f

1e ⟶

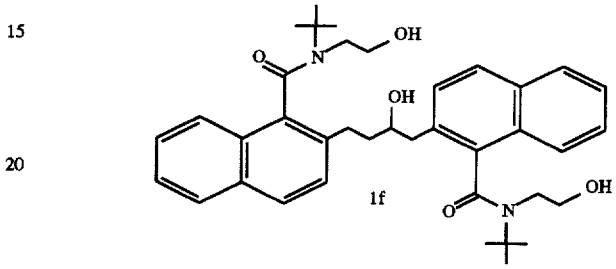

A solution of 0.15 gm (0.15 mmol) of compound 1e in 1 ml of THF was charged to a 5 ml round bottom flask and 304 microliters of a 1.0M solution of tetrabutyl ammonium fluoride was added, dropwise. The clear solution became light yellow. After 30 minutes, TLC indicated no residual starting material remained. The mixture was poured into ether, washed with water and brine and dried over MgSO₄. The organic phase was then filtered and the solvent was removed under vacuum, yielding a clear oil which was purified by flash chromatography. 'HNMR confirmed the structure.

EXAMPLE 2

Preparation of

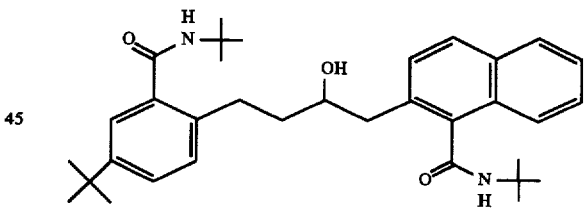

Step 2a

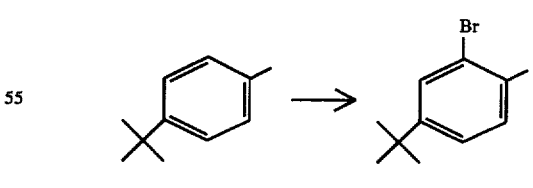

To a solution (reddish purple) of 5 gm (33.73 mmol) of p-t-butyl toluene and a catalytic amount of iodine was added 5.66 gm (35.41 mmol) of bromine. The reaction mixture turned bright red within 5 minutes, generating white smoke. The reaction was stirred for 2 hours at room temperature at which time water and ether were carefully added to the mixture. The mixture was poured into a separatory funnel with additional water and ether. The organic layer was separated, washed three times with saturated NaHCO₃ and once with brine, then dried over MgSO₄ and filtered. The solvent was removed under vacuum. The product was evaporated twice with benzene and subjected to high vacuum to remove all residual solvents. 'HNMR confirmed the product structure.

Step 2b

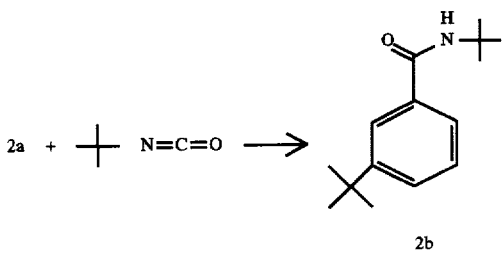

Compound 2a was brought to a gentle reflux in 25 ml of ether containing 0.2 gm of lithium wire. After 4 hours the original clear solution was murky and light yellow. The heating bath was removed and the mixture allowed to cool to room temperature whereupon 1.21 gm (14.52 mmol) of t-butyl isocyanate was added. The solution became orange and finally light yellow and refluxed slightly during the addition. After 30 minutes the reaction was monitored by TLC and no residual starting material was present. The mixture was poured into water, extracted with ether and then the organic layers were washed with brine and dried over MgSO₄. The extracts were filtered and the solvent was removed under vacuum. A white solid was recovered which was triturated with hexane and collected by vacuum filtration. Yield was 1.1 gm. The entire procedure was repeated with the filtrate and an additional 0.44 gm was recovered. The structure was confirmed by NMR.

Step 2c

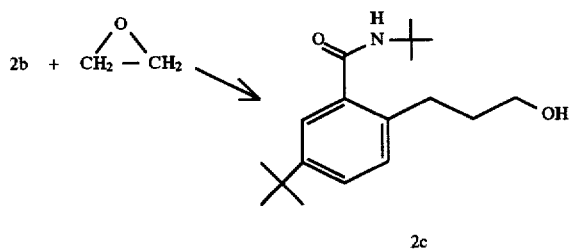

A solution of 1.45 gm (5.86 mmol) of compound 2b and 1.4 gm of TMEDA was cooled to −78° C. and 7.1 ml of a 1.69M solution of n-butyl lithium in hexane was added dropwise. A light orange color formed and disappeared into a clear solution during the addition. This color then developed into a neon orange by the time all of the n-butyl lithium had been added. The mixture was stirred at −78° C. for 1 hour. At this time 0.29 gm (6.5 mmol) of ethylene oxide was added rapidly in a single addition. No color change was observed. After 5 minutes at −78° C. the reaction mass was allowed to warm to 0° C. As the mass began to warm the color changed to bright yellow, slightly murky. Monitoring by TLC indicated that no residual starting material was present. The reaction mass was then poured into water and extracted with diethylether. The organic phases were washed with brine and dried over MgSO₄. The mixture was then filtered and the solvent removed under vacuum. A white solid was recovered which was triturated with hexane and collected by vacuum filtration. The structure was confirmed by 'HNMR.

Step 2d

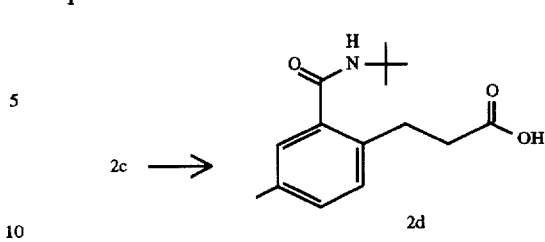

A solution of 1.21 gm (4.15 mmol) of compound 2c and 7.81 gm of pyridinium dichromate in 16 ml of DMF. was stirred at room temperature overnight. After overnight stirring the mixture was poured into water and extracted twice with ethyl acetate. The organic phases were collected, dried over MgSO₄ and filtered. The solvent was removed under vacuum, producing a brown oil. TLC indicated DMF was still present so the oil was dissolved in ether,washed with water and brine, and dried over MgSO₄ and filtered. The solvent was removed under vacuum. A white solid product was recovered, triturated with hexane and collected by vacuum filtration. The structure was confirmed by 'HNMR.

step 2e

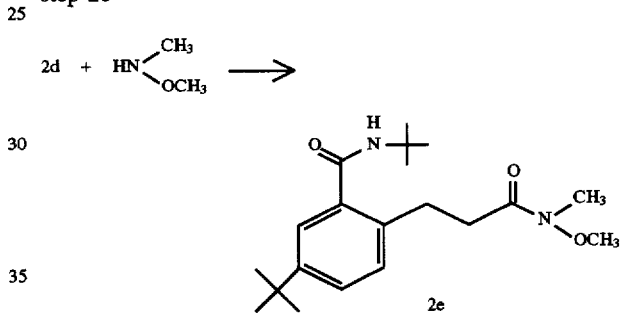

A solution of 0.305 gm (1 mmole) of compound 2d and 0.098 gm (1 mmole) of N,O-dimethyl hydroxylamine hydrochloride in 2 ml of DMF was cooled to 0° C. To this clear solution 0.135 gm of 1-hydroxy benzotriazole, 0.192 gm of 1-(3-dimethylaminopropyl)-3-ethylcarbodiimide (EDC) and 0.304 gm of triethylamine were added, producing a turbid solution. After sitting 5 minutes the reaction mass was allowed to warm to room temperature and stirred for three hours. After 2 additional hours TLC analysis indicated that no residual starting material was present. The mixture was then poured into ethyl acetate, washed with water, 10% citric acid, saturated sodium bicarbonate and brine and dried over MgSO₄. The mixture was then filtered and the solvent was removed under vacuum, producing a clear oil. This oil was purified by column chromatography using a 4:1 ether/hexane mixture. Fractions 13–31 were collected and structure was confirmed by NMR. The yield was 52%.

Step 2f

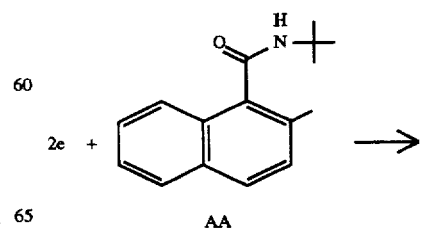

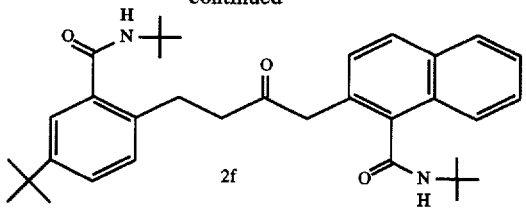

Compound AA was prepared in the following manner. heterogeneous mixture of 2 gm (10.75 mmol) of 2-methyl naphthoic acid in toluene was cooled to 0° C. and oxalyl chloride was added, dropwise, followed by dropwise addition of 0.236 gm of dimethylformamide (DMF). As the DMF was added, gas was vigorously evolved and the solid 2-methyl naphthoic acid began to go into solution. After 5 minutes, the reaction mixture was allowed to warm to room temperature. The solution was clear and golden with a small amount of white precipitate. After 20 minutes the precipitate had dissolved into the solution and the reaction was monitored by infrared analysis. The reaction mass was concentrated under vacuum. As the oxalyl chloride evaporated, a large amount of a white solid settled out. The solution could not be further concentrated due to the presence of the solid. The mixture was cooled to 0° C. and 1.65 gm of t-butylamine was added. A fine white precipitate settled out. The bath was then removed and after 15 minutes at room temperature the reaction mass was poured into water and extracted with ethyl acetate. The organic phases were collected, washed with brine, and dried over MgSO$_4$. The solvent was removed under vacuum. The solid was purified by column chromatography using a 2-1 hexane to ether solution as the eluant. Following chromatography the product was recrystallized from an ether/hexane mixture. Structure was confirmed by NMR. Yield was 83%.

Then, a solution of 0.28 gm (1.15 mmol) of compound AA and 0.272 gm of TMEDA in 10 ml of THF was cooled to –78° C. in a dry ice/acetone bath. After 15 minutes at –78° C., 1.4 ml of a 1.69N solution of n-butyl lithium in hexane was added dropwise. A faint purple color changed to turquoise and eventually to purple during the addition of the n-butyl lithium. The deep purple solution was stirred for one hour at –78° C. After 1 hour of stirring, a solution of 0.18 gm (0.52 mmol) of compound 2e in 4 ml of THF was added. After 20 more minutes at –78° C., TLC monitoring indicated that no residual starting material was present. The mixture was poured into water, extracted with ether, washed with brine and dried over MgSO$_4$. Solvent was removed under vacuum and the residue was purified by column chromatography using a 2:1 mixture of ether and hexane. Fractions 25–45 were collected. 'HNMR confirmed the structure. The yield was 81%.

Step 2g

2f →

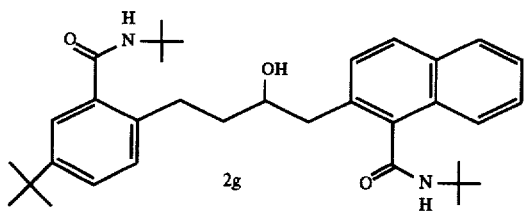

A solution of 0.1 gm (0.28 mmol) of compound 2f in 1 ml of ETOH was cooled to 0° C. and 0.011 gm of sodium borohydrate granules was added to the clear solution. After 30 minutes, TLC monitoring indicated that starting material was still present. The reaction was allowed to warm to room temperature and 0.015 gm of additional sodium borohydride was added. After 30 more minutes at room temperature, there appeared to be no more residual starting material present. The reaction mass was poured into saturated sodium bicarbonate, extracted with ether, washed with brine, dried over MgSO$_4$ and filtered. Solvent was removed under vacuum and the white amorphous solid which was recovered was purified by column chromatography using a 2:1 ether/hexane solution. Fractions 5–13 were collected and the structure was confirmed by NMR. Yield was 85.3%.

EXAMPLE 3

Preparation of

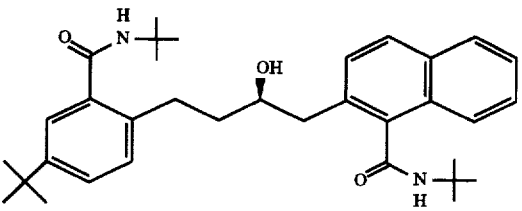

Step 3a

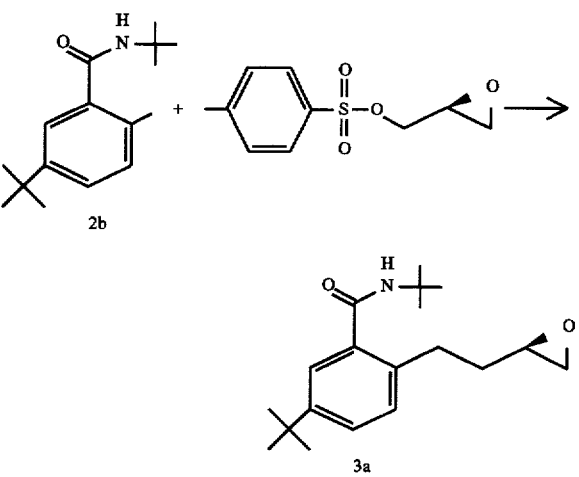

A solution of 0.5 gm of compound 2b and 0.47 gm of TMEDA in 10 ml of toluene was cooled to –78° C. in a dry ice/acetone bath. The mixture was allowed to sit for 15 minutes at –78° C. and 2.38 ml of a 1.7M solution of n-butyl lithium in hexane was added dropwise. The color of the reaction mixture changed from light orange to clear and then to a bright orange color during the addition of the n-butyl lithium. The mass was stirred at –78° C. for 1 hour and a solution of 0.461 gm (2.02 mmol) of S-glycidyl tosylate in 5 ml of THF was added. The color changed immediately to a light yellow. After an additional 15 minutes at –78° C., TLC indicated only a small amount of starting material remained. The reaction was poured into water and extracted with ether, washed with brine, and dried over MgSO$_4$. The mixture was then filtered and the solvent was removed under vacuum. The yellow oil thus recovered was purified by flash chromatography using a 2:1 solution of hexane and ether. Fractions 45–75 were collected. NMR confirmed the structure of the product. The yield was 52%.

Step 3b

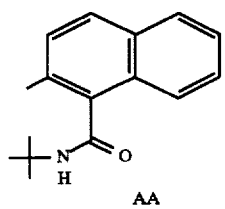

AA

Compound AA was prepared in the following manner. A heterogeneous mixture of 2 gm (10.75 mmol) of 2-methyl naphthoic acid in toluene was cooled to 0° C. and oxalyl chloride was added, dropwise, followed by dropwise addition of 0.236 gm of dimethylformamide (DMF). As the DMF was added, gas was vigorously evolved and the solid 2-methyl naphthoic acid began to go into solution. After 5 minutes, the reaction mixture was allowed to warm to room temperature. The solution was clear and golden with a small amount of white precipitate. After 20 minutes the precipitate had dissolved into the solution and the reaction was monitored by infrared analysis. The reaction mass was concentrated under vacuum. As the oxalyl chloride evaporated, a large amount of a white solid settled out. The solution could not be further concentrated due to the presence of the solid. The mixture was cooled to 0° C. and 1.65 gm of t-butylamine was added. A fine white precipitate settled out. The bath was then removed and after 15 minutes at room temperature the reaction mass was poured into water and extracted with ethyl acetate. The organic phases were collected, washed with brine, and dried over MgSO$_4$. The solvent was removed under vacuum. The solid was purified by column chromatography using a 2-1 hexane to ether solution as the eluant. Following chromatography the product was recrystallized from an ether/hexane mixture. Structure was confirmed by NMR. Yield was 83%.

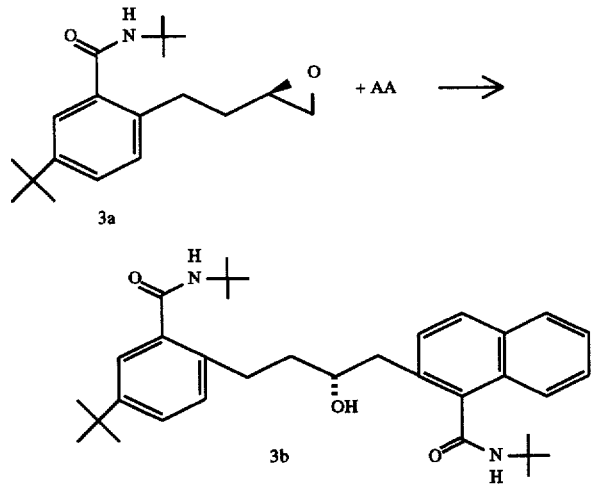

Then, a solution of 0.3 gm (1.32 mmol) of compound AA and 0.31 gm of TMEDA in 5 ml of THF was cooled to 0° C. After the solution had stirred at 0° C. for 15 minutes, 2.6 ml of a 1.0N solution of s-butyl lithium in cyclohexane was slowly added to it. As the butyl lithium was added, the original orange color changed to clear and then to an orange color which bright red/orange. After 1 more hour at 0° C. a solution of 0.2 gm (0.66 mmol) of compound 3a in 1.5 ml of THF was slowly added. No color change was observed. After 15 minutes, TLC indicated no residual starting material. The solution was then poured into ether, washed with water, then brine and dried over MgSO$_4$. The product was then filtered and the solvent was removed under vacuum, yielding a clear oil. This oil was purified by flash chromatography using a 2-1 ether to hexane mixture as the eluant. Fractions 20–30 were collected and the solvent was removed under vacuum. NMR confirmed the structure. Yield was 50%.

EXAMPLE 4

Preparation of

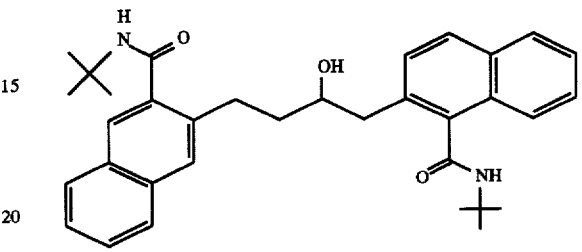

Step 4a

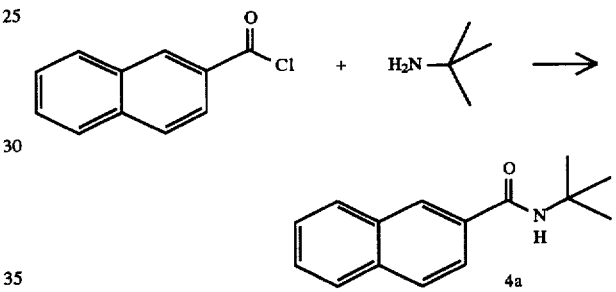

A solution of 7.96 gm of triethylamine and 5.76 gm (78.7 mmol) of t-butylamine in 140 ml of THF was cooled to 0° C. and a solution of 15 gm (78.7 mmol) of 2-naphthoyl chloride in 10 ml of THF was added. A white precipitate formed immediately. After 10 minutes the reaction mass was allowed to warm and was stirred at room temperature for two hours. TLC indicated at this point that no residual starting material was present. The mixture was poured into water, extracted with ether, washed with 10% citrate acid, saturated NaHCO$_3$, then with brine, and finally was dried over MgSO$_4$. The mixture was then filtered and the solvent was removed under vacuum. A white solid precipitated out as the solvent evaporated and 9.8 gm of product were collected by vacuum filtration.

The above procedure was repeated with the filtrate and an additional 2.2 gm of product were collected. NMR confirmed the structure. Yield was 67%.

Step 4b

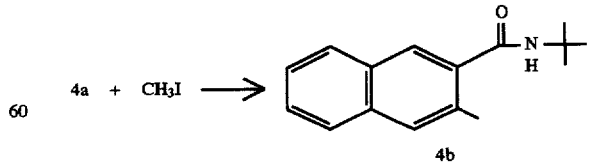

A solution of 3.5 gm (15.41 mmol) of compound 4a and 3.94 gm of TMEDA in 90 ml of THF was cooled to −78° C. in a dry ice/acetone bath. After 15 minutes at −78° C., 34 ml of a 1.0N solution of s-butyl lithium in cyclohexane was slowly added. The solution immediately turned yellow and, as the butyl lithium addition continued, turned to bright orange and finally to an opaque butterscotch color. The mixture was then stirred for 1 hour at −78° C., at which time 2.4 gm (16.94 mmol) of iodomethane was added. The solution immediately turned to a light yellow green color with a white precipitate floating in it. The reaction mass was stirred at −78° C. for another hour. Although TLC indicated that there was residual starting material still present, the mixture was poured into ether, washed with water and brine, then dried over MgSO₄. The mixture was filtered and solvent was removed under vacuum. The product was purified by flash chromatography using a 3:1 hexane/ether solution. Fractions 13–19 were collected and solvent was removed under vacuum yielding 1.35 gm of a white solid material. The procedure was repeated and an additional 0.65 gm was recovered from the second procedure. Structure of the product was confirmed by ¹HNMR.

Step 4c

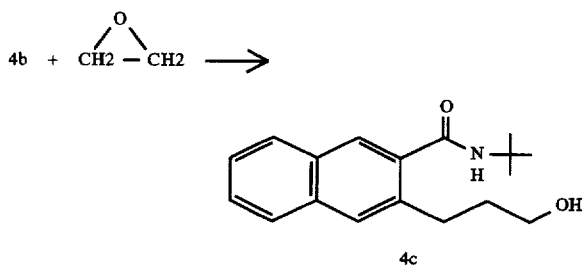

A solution of 2.21 gm (9.16 mmol) of compound 4b and 2.19 gm of TMEDA in 80 ml of THF was cooled to −78° C in a dry ice/acetone bath. After the solution had cooled for 15 minutes, 11.1 ml of a 1.69M solution of n-butyl lithium in hexane was added dropwise. The original bright purple color disappeared and then reappeared as the butyl lithium addition progressed. The reaction was stirred for another hour at −78° C. at which time 0.81 gm (18.32 mmol) of ethylene oxide was added. No color change was observed. After 10 more minutes at −78° C. the reaction mass was allowed to warm to 0° C. As it warmed, its color changed to a light orange. TLC analysis indicated that almost no residual starting material was present. The solution was then poured into water, extracted with ether, and washed with brine. The organic portion was dried over MgSO₄. The mixture was then filtered and solvent was removed under vacuum. Structure was confirmed by NMR.

Step 4d

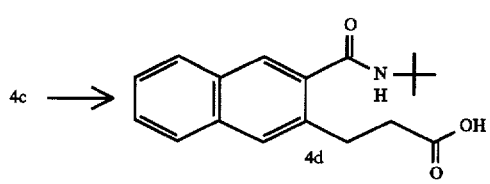

A solution of compound 4c (about 9.16 mmol) and 17.23 gm of pyridinium dichromate in 35 ml of methylene chloride was stirred at room temperature for 4 hours. TLC indicated that a small amount of aldehyde was present, so the reaction was then allowed to continue with stirring for another 16 hours. At that time, TLC analysis indicated that no aldehyde was present. The mixture was poured into 350 ml of water and extracted twice with 300 ml of ether. The organic layers were combined, washed with water, dried over MgSO₄, and filtered. The solvent was then removed under vacuum and a white solid material precipitated out. This was triturated with benzene and 12.08 gm of product was recovered by vacuum filtration. The structure was confirmed by NMR. Yield was about 40% over two steps.

Step 4e

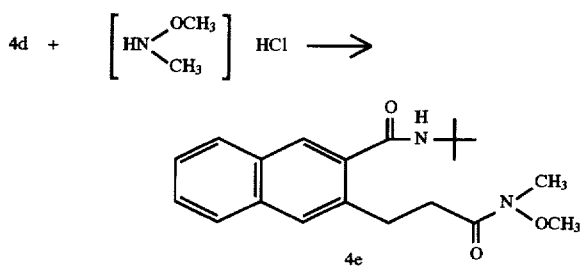

A solution was prepared consisting of 0.4 gm (1.34 mmol) of compound 4d, 0.131 gm (1.34 mmol) of N,O-dimethylhydroxylamine hydrochloride, 0.405 gm of triethyl amine and 0.6 gm of BOP reagent. The solution was stirred at room temperature for 2 hours at which time TLC indicated that no residual starting material remained. The reaction was poured into ether, washed with water and 10% citric acid, saturated NaHCO₃ and brine, then dried over MgSO₄. The mixture was filtered and solvent was removed under vacuum, yielding a white oily product. This white oil was purified by flash chromatography using a 3:1 ether/hexane solution. Fractions 34–69 were collected. NMR confirmed the structure of the product. The yield was 78%.

Step 4f

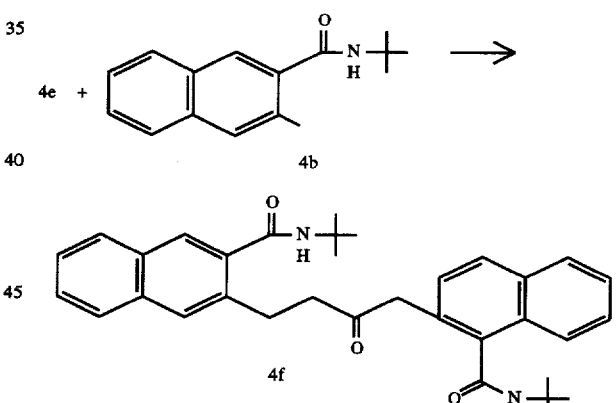

A solution of 0.148 gm (0.613 mmol) of compound 4b and 0.143 gm of TMEDA in 5 ml of THF was cooled to −78° C. in a dry ice/acetone bath. After the solution had cooled at −78° C. for 15 minutes, 0.725 ml of a 1.7M solution of n-butyl lithium in hexane was added. The resulting purple solution was stirred at −78° C. for 1 hour at which time 0.1 gm (0.292 mmol) of compound 4e in 1 ml of THF was added in a single portion. No color change was observed. The reaction mass was stirred for an additional 15 minutes at −78° C. at which time TLC analysis indicated no residual starting material was present. The mixture was then poured into ether, washed sequentially with water and brine, dried over MgSO₄, and filtered. Solvent was removed under vacuum. ¹H NMR confirmed the structure. Material was not purified further.

Step 4g

4f →

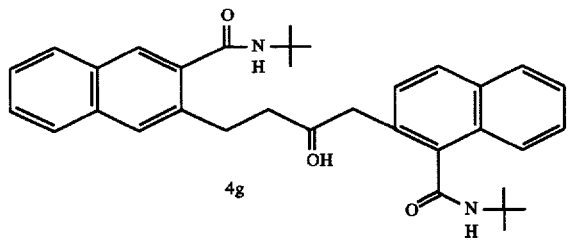

4g

A solution was prepared of product 4f in 5 ml of ethanol and 0.017 gm (0.44 mmol) of sodium borohydride granules was added to the clear solution. After 30 minutes, TLC indicated no residual starting material remained. The reaction mixture was poured into ether, washed sequentially with saturated $NaHCO_3$ and brine, then dried over $MgSO_4$. The dried extracts was filtered and the solvent was removed under vacuum. A yellow oil/solid material was recovered and purified by flash chromatography using a 3 to 2 ether/hexane solution. Fractions 50-90 were collected. NMR confirmed structure of the product.

EXAMPLE 5

Preparation of

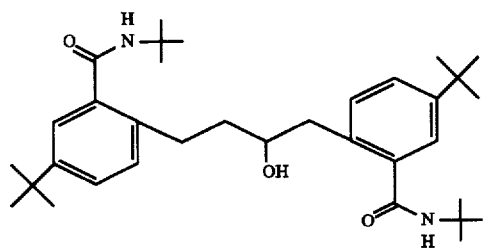

Step 5a

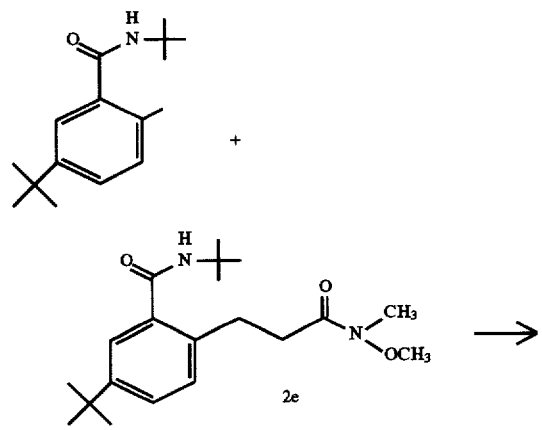

-continued

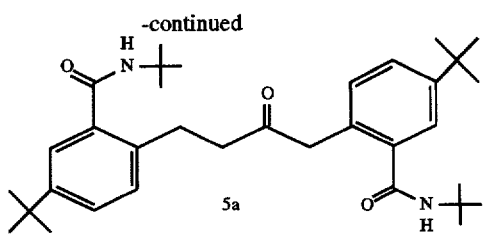

5a

A solution of 0.151 gm (0.61 mmol) of compound 2b and 0.142 gm of TMEDA in 5 ml of THF was cooled to −78° C. in a dry ice/acetone bath. After the solution had cooled for 15 minutes at −78° C., 0.47 ml of a 2.6M solution of n-butyl lithium in hexane was added slowly. An orange solution resulted which was stirred at −78° C. for 1 hour. At the end of this hour 0.1 gm (0.29 mmol) of compound 2e in 1 ml of THF was added. The solution became light yellow at the end of the addition and was stirred for an additional 15 minutes at −78° C. At this time, TLC indicated no residual starting material was present. The mixture was poured into ether, washed sequentially with water and brine, dried over $MgSO_4$.

Step 5b

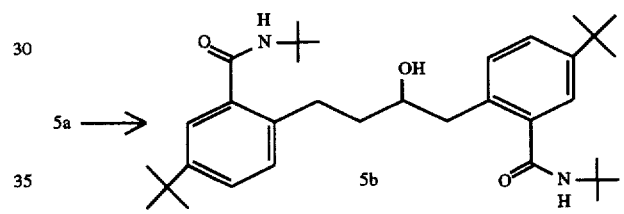

5a → 5b

The crude product from Step 5a (approximately 0.29 mmol) was dissolved in 5 ml of ethanol and 0.017 gm of sodium borohydride granules was added to the clear solution. After 30 minutes, TLC indicated no residual starting material was present. The reaction was poured into ether, washed sequentially with saturated $NaHCO_3$ and brine, then dried over $MgSO_4$. The extracts were filtered, the solvent was removed under vacuum and the residual product was purified by flash chromatography using a 1:1 ether hexane solution as the eluent. Fractions 46-72 were collected and the solvent was removed under vacuum. Yield was 55% over steps a and b and NMR confirmed the structure.

EXAMPLE 6

Preparation of

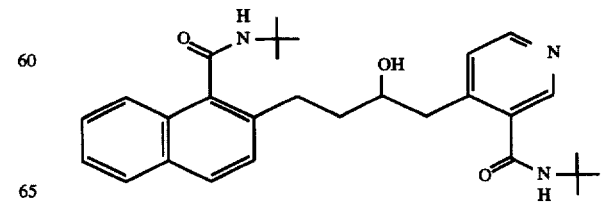

Step 6a

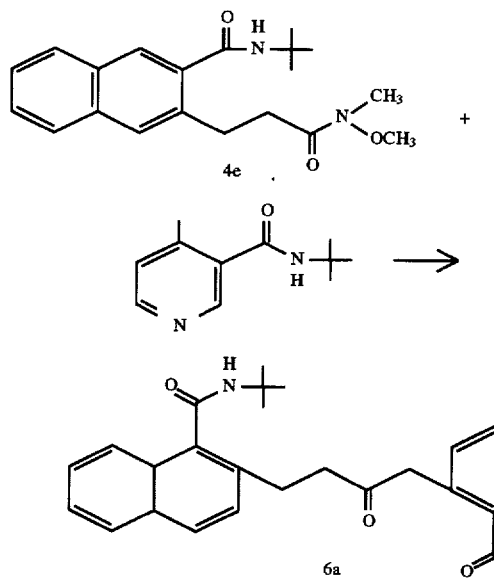

A solution of 0.12 gm (0.61 mmol) of 4-methyl-3-(t-butyl) carbamoyl-pyridine and 0.142 gm of TMEDA in 5 ml of THF was cooled to −78° C. in a dry ice/acetone bath. After the solution had cooled for 15 minutes at −78° C., 0.47 ml of a 2.6M solution of n-butyl lithium in hexane was slowly added. The solution changed to a light yellow color and was allowed to stir at −78° C. for an additional hour. At this time a solution of 0.1 gm (0.29 mmol) of compound 4e in 1 ml of THF was rapidly added. After 30 minutes and again at 1 hour, TLC analysis indicated that not all of compound 4e had been consumed. The reaction mass was then poured into ether, washed sequentially with water and brine and dried over MgSO$_4$. The mixture was filtered and the solvent was removed under vacuum, yielding an oil. The oil was purified by column chromatography and fractions 68–78 were collected cleanly. NMR confirmed the structure of these materials.

Step 6b

6a $\longrightarrow$

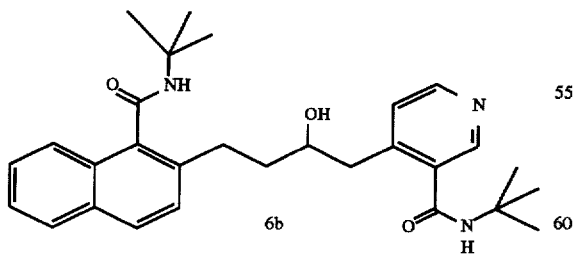

Compound 6a was reduced with sodium borohydride in the manner described in previous examples. NMR confirmed the structure.

EXAMPLE 7

Preparation of

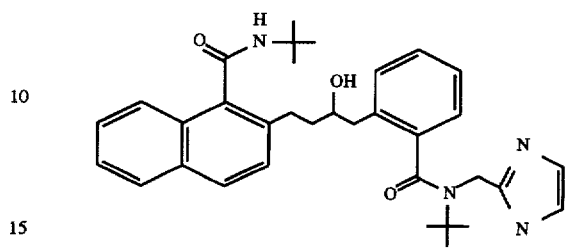

Step 7a

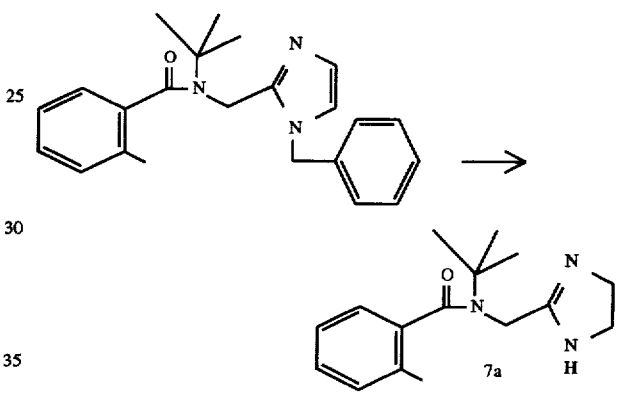

A solution of 0.21 gm (0.58 mmol) of N-(N-benzyl)-imidazole, N-t-butyl-toluamide was prepared in 2 ml of ethanol. To this solution was added 0.062 gm of palladium black followed by 0.36 gm of ammonium formate. Within 5 minutes, the black solution began to bubble. After 1 hour, TLC indicated that no reaction had taken place as yet. The reaction mixture was warmed to 70° C. and, after 1 hour at that temperature, TLC indicated that no residual starting material was present. An additional 0.36 gm of ammonium formate was added and the reaction left at 70° C. overnight. The mass was filtered over Celite™ and washed with ethyl acetate and methanol. Solvent was removed under vacuum, producing a white solid. The structure was confirmed by NMR. Yield was 95%.

Step 7b

7a +

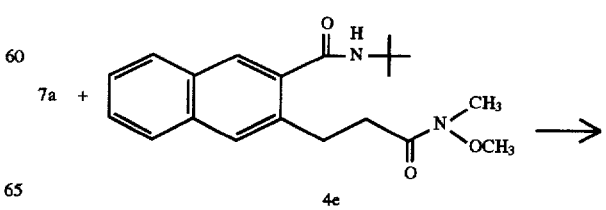

-continued

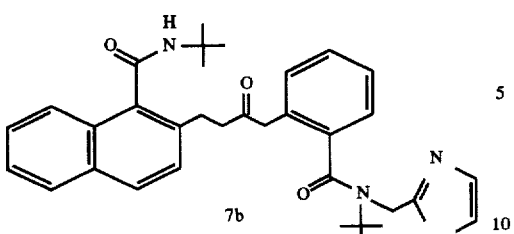

7b

A solution of 0.15 gm (0.55 mmol) of compound 7a and 0.03 gm (0.33 mmol) of diisopropylamine in 5 ml of THF was cooled to −78° C. in a dry ice acetone bath. After the solution had sat at −78° C. for 15 minutes, 1.57 ml of a 0.91M solution of s-butyl lithium in cyclohexane was slowly added. A bright blood red color developed and the solution was stirred for 20 additional minutes at −78° C.. At this point, a solution of 0.095 gm (0.275 mmol) of compound 4e in 1 ml of THF was quickly added. The color faded to a burgundy red color. TLC indicated almost no residual starting material to be present. The reaction mass was quenched with 1 ml of water, poured into additional water and extracted with 15 ml of ether. The organic phase was washed with 15 ml of brine, dried over $MgSO_4$ and filtered. The solvent was removed under vacuum. The residue was purified by flash chromatography using a 3 to 1 solution of ethyl acetate and hexane as the eluent. Fractions 21–49 were collected and solvent was removed under vacuum. NMR confirmed the structure. Further workup was not carried out at this point.

Step 7c

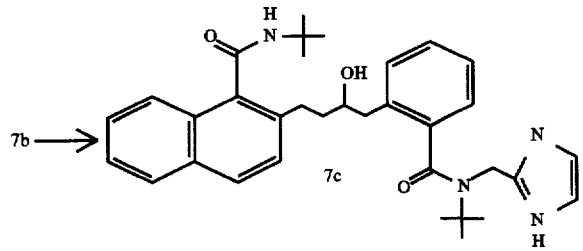

7b →    7c

A solution of 0.11 gm (0.2 mmol) of crude compound 7b in ethanol was prepared and 0.012 gm of sodium borohydrate granules was added to the clear solution. After 30 minutes, TLC indicated that no residual starting material was present. The reaction mixture was quenched with 10 drops of saturated $NaHCO_3$ and the mixture was poured into 10 ml of saturated $NaHCO_3$ and extracted with 15 ml of ethyl acetate. The organic layers were washed with brine and dried over $MgSO_4$. The mixture was filtered and the solvent was removed under vacuum. The residue was purified by flash chromatography using ether as the eluent until the first spot came off and then using ethyl acetate. Fractions 81–102 were collected cleanly. NMR confirmed the structure.

EXAMPLE 8

Preparation of

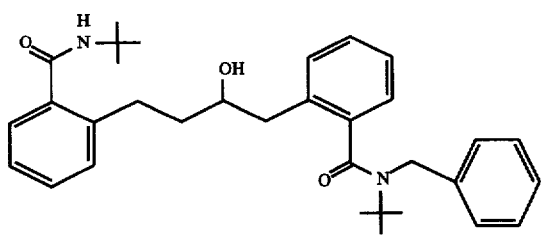

Step 8a

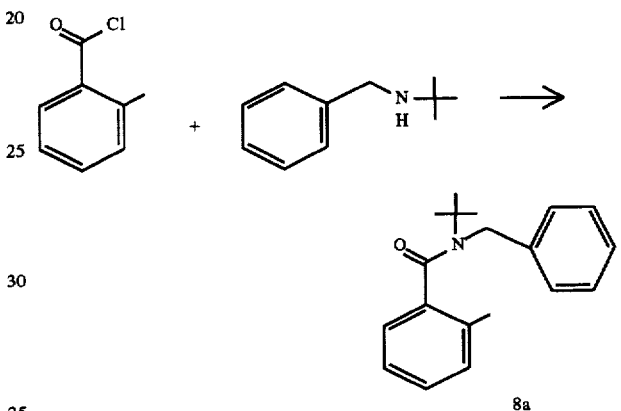

8a

To a solution of 3.27 gm of triethylamine and 5.28 gm of N-(t-butyl) benzylamine in 40 ml THF at 0° C. was added 5.0 gm (33.34 mmol) of O-toluoyl chloride, dropwise, at 0° C. Within 5 minutes, a white precipitate came out of the solution and after an additional 15 minutes the cooling bath was removed and the reaction mixture was stirred for 2 hours. At this time, TLC indicated that no residual starting material was present. The mixture was poured into water and extracted with ether. The organic phase was washed sequentially with saturated $NaHCO_3$, 10% citric acid and brine, and dried over $MgSO_4$. The mixture was filtered and the solvent was removed under vacuum yielding a yellow oil. This oil was purified by flash chromatography. The material was collected and the solvent was removed under vacuum. The clear oil crystallized into a white solid when hexane was added and was collected by filtration. NMR confirms the structure. Yield was 73.5%.

Step 8b

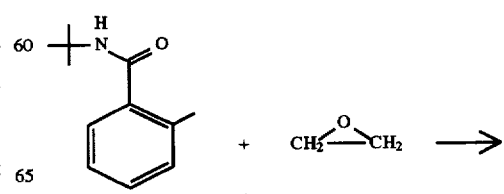

-continued

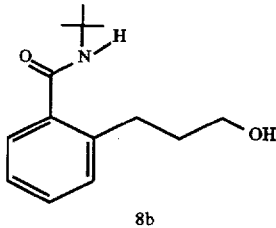

8b

N-(t-butyl)-toluamide (7.58 gm, 39.6 mmol) was dissolved in 400 ml of THF and 9.96 gm (81.2mmol) of TMEDA was added. The mixture was cooled to -78° C. and 31.2 ml of 2.6M n-butyl lithium in hexane was added dropwise. After 1 hour, a solution of 1.92 gm (43.6 mmol ) of ethylene oxide was added as a 10% solution in THF. After 15 minutes the solution was warmed to 0° C. A precipitate formed and the reaction mixture turned murky orange. After another 30 minutes, TLC indicated presence of product plus starting material. Recrystallization from ether/hexane yielded 3.49 gm of pure product. Flash chromatography of the remainder with 2:1 ether/hexane, yielded another 2.96 gm of pure product. Total yield was 6.45 gm (69%).
Step 8c

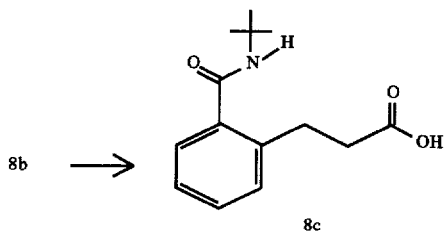

A solution of 3.49 gm (14.8 mmol) of compound 8b in 60 ml of DMF was prepared and 27.9 gm of pyridinium dichromate was added. The solution turned a dark brown/orange color and was stirred overnight at room temperature. The mixture was poured into H₂O and extracted once with 150 ml of ether and once with 50 ml of ether, then dried over MgSO₄. Solvent was removed under vacuum, yielding a clear, colorless oil, which turned solid after standing. Recrystallization in pure ether yielded white crystals. The product was filtered and washed with hexane. Two crops yielded 1.48 gm (40%) of white powder.
Step 8d

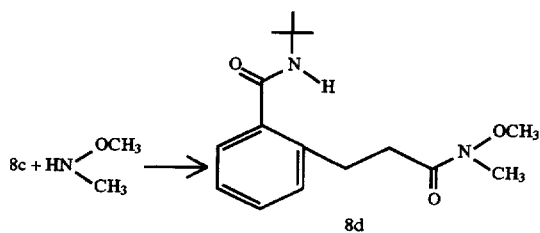

A solution of 0.8 gm (3.21 mmol) of compound 8c in 40 ml of methylene chloride was prepared. To this solution was added 0.313 gm (3.21 mmol) of N,O-dimethylhydroxyl amine hydrochloride and 1.34 ml of triethylamine. When the amine hydrochloride was completely dissolved, 1.42 gm of BOP benzotriazol-1-yloxy-tris(dimethyl-amino) phosphonium hexafluorophosphate reagent was added and the clear solution was stirred for 2 hours at room temperature. TLC indicated that no starting material remained. The reaction mixture was poured into ether and washed with 10% citric acid solution, H₂O, saturated NaHCO₃ and brine, then dried over MgSO₄. Flash chromatography in 2:1:1 methylene chloride/ethyl acetate/hexane yielded 0.539 (57%) of white powder.
Step 8e

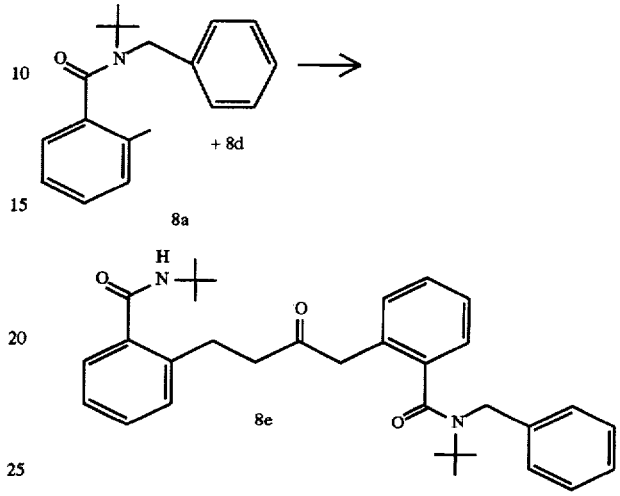

A solution of 0.2 gm (0.7 mmol) of compound 8a and 0.02 gm of diisopropylamine in 5 ml of THF was cooled to -78° C. in a dry ice/acetone bath. After the solution had cooled at -78° C. for 15 minutes, 1 ml of 0.92M s-butyl lithium was slowly added, producing a bright purple color. A solution of 0.1 gm (0.342 mmol) of compound 8d in 1 ml of THF was added within 10 seconds following the addition of the butyl lithium solution and before the color changed. The addition caused the solution to turn a slight peach color. After 5 minutes, TLC indicated that residual starting materials were still present but the color had all disappeared. The reaction was quenched with 1 ml of water, then poured into 20 ml of water and extracted with ether. The organic extract was washed with 20 ml of brine, dried over MgSO₄ and filtered. The solvent was removed under vacuum and the clear residue (280 mg) was purified by column chromatography using a 2 to 1 ether/hexane solution. The product was collected cleanly and NMR confirmed the structure. Yield was about 29%.
Step 8f

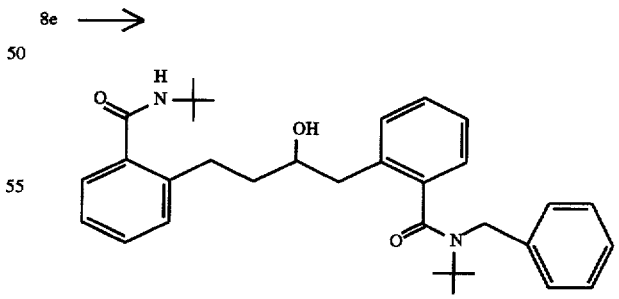

A solution of 0.05 gm (0.10 mmol) of compound 8e in 3 ml of ethanol was prepared and 0.0057 gm of NaBH₄ granules was added to the clear solution. After Stirring for 30 minutes, TLC indicated that some residual starting material was still present. Another equivalent of NaBH₄ was added and the reaction was stirred for an additional 45 minutes. No residual starting material was found at this point. The reaction was quenched with 10 drops of saturated NaHCO₃, poured into 10 ml of saturated NaHCO₃ and extracted with 15 ml of ether. The extracts were washed with brine, dried over MgSO₄ and filtered. Solvent was removed under vacuum and the residue was purified by column chromatography using a 3 to 1 ether/hexane solution. Fractions 21–45 were collected cleanly. NMR confirmed the structure. Yield was about 90%.

EXAMPLE 9

Preparation of

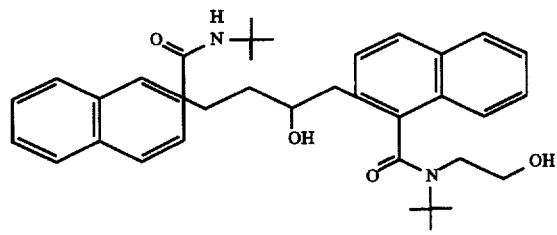

Step 9a

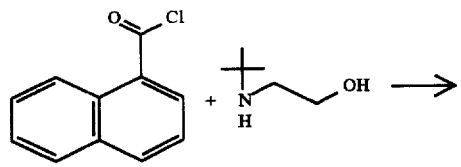

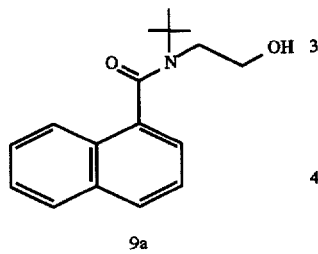

9a

A solution of 3.07 gm (26.23 mmol) of N-t-butyl amine and 7.96 gm of triethylamine in 60 ml of methylene chloride was cooled to 0° C. and 10 gm (52.46 mmol) of naphthoyl chloride was slowly added. The reaction mixture was allowed to warm slowly to room temperature. After 1 hour at room temperature, TLC indicated that residual starting N-t-butyl ethanol amine was still present so the reaction was allowed to sit overnight. The mixture was then poured into ether, washed sequentially with water, 10% citric acid, saturated NaHCO₃ and brine. The organic layers were dried over MgSO₄ and filtered. The solvent was removed under vacuum yielding a yellow oil. The yellow oil was dissolved in a 9 to 1 methanol/water solution and 5 ml of a 45% KOH solution was added. The solution immediately became turbid with a white solid, which settled to yield a clear solution. After 5 minutes, TLC indicated that no residual starting material was present. The reaction was poured into water and extracted twice with ether. The organic extract was dried over MgSO₄ and filtered. The solvent was evaporated under vacuum. The yellow oil solidified upon standing, was triturated with hexanes and collected by filtration. NMR confirmed the structure. The yield was 64%.

Step 9b

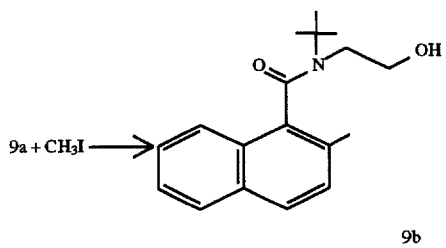

9b

A solution of 2.5 gm (9.2 mmol) of compound 9a and 2.36 gm of TMEDA in 50 ml of THF was cooled to –78° C. in a dry ice/acetone bath. After the mixture had stirred for 15 minutes at –78° C., 20.27 ml of a 1.0M solution of s-butyl lithium in cyclohexane was added, dropwise. The color changed to yellow and then to green and then to a dark green during this addition. The solution was stirred at –78° C. for 1 hour after which 1.3 gm (9.2 mmol) of iodomethane was added in one portion. The reaction mix became yellow with a white precipitate. After 15 minutes TLC indicated that almost no residual starting material was present. The mixture was poured into an ether and water mixture. The organic phase was washed sequentially with water and brine and then dried over MgSO₄. The mixture was then filtered and solvent was removed under vacuum, yielding an orange oil. This oil was purified by flash chromatography using a 2 to 1 ether/hexane solution. Fractions 28–46 were collected cleanly. Structure was confirmed by NMR. Yield was approximately 45%.

Step 9c

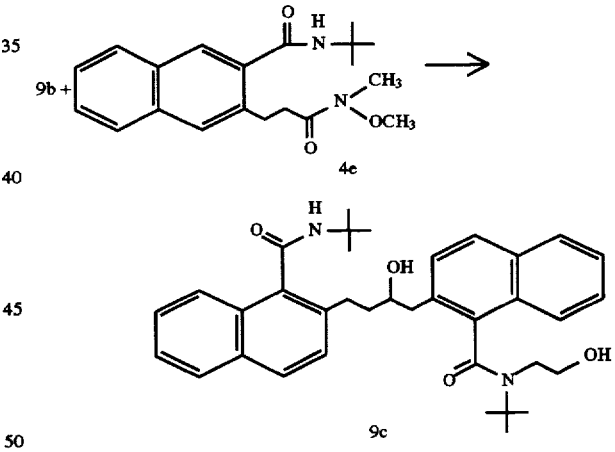

A solution of 0.17 gm (0.595 mmol) of compound 9b and 0.0176 gm of diisopropylamine in 5 ml of THF was cooled to –78° C. After the mixture had cooled for 15 minutes at –78° C., 1.33 ml of a 1.0M solution of s-butyl lithium in cyclohexane was slowly added. No color change was apparent at this point, so another 0.4 ml of the solution was added and a blood red color was noted. When the entire amount of the s-butyl lithium had been added the reaction mixture was stirred for an additional 15 minutes at –78° C. At this point, a solution of 0.10 gm (0.29 mmol) of compound 4e in 1 ml of THF was added quickly. No color change was observed. After 15 minutes TLC indicated that no residual starting material was present and 1 ml of water was added to quench the reaction. The mixture was poured into ether and the organic layers were washed sequentially with water and brine, then dried over MgSO₄. The mix was then filtered and the solvent was removed under vacuum. The residue was dissolved in 5 ml of ethanol and 0.017 gm of NaBH₄ crystals were added. A white precipitate formed in the solution and slowly dissolved, yielding again a clear solution. This solution was poured into saturated NaHCO₃ and extracted with ether. The organic extract was washed in brine then dried over MgSO₄ and filtered. The solvent was then removed under vacuum. The clear oil was purified by column chromatography. The structure was confirmed by ¹HNMR.

EXAMPLE 10

Preparation of

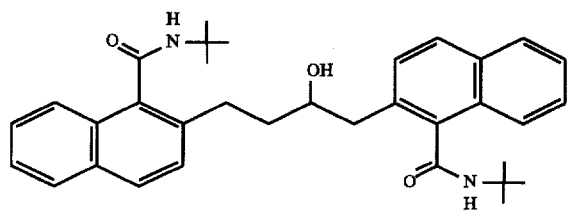

Step 10a

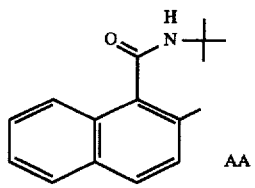

Compound AA was prepared in the following manner. A heterogeneous mixture of 2 gm (10.75 mmol) of 2-methyl naphthoic acid in toluene was cooled to 0° C. and oxalyl chloride was added, dropwise, followed by dropwise addition of 0.236 gm of dimethylformamide (DMF). As the DMF was added, gas was vigorously evolved and the solid 2-methyl naphthoic acid began to go into solution. After 5 minutes, the reaction mixture was allowed to warm to room temperature. The solution was clear and golden with a small amount of white precipitate. After 20 minutes the precipitate had dissolved into the solution and the reaction was monitored by infrared analysis. The reaction mass was concentrated under vacuum. As the oxalyl chloride evaporated, a large amount of a white solid settled out. The solution could not be further concentrated due to the presence of the solid. The mixture was cooled to 0° C. and 1.65 gm of t-butylamine was added. A fine white precipitate settled out. The bath was then removed and after 15 minutes at room temperature the reaction mass was poured into water and extracted with ethyl acetate. The organic phases were collected, washed with brine, and dried over MgSO₄. The solvent was removed under vacuum. The solid was purified by column chromatography using a 2-1 hexane to ether solution as the eluant. Following chromatography the product was recrystallized from an ether/hexane mixture. Structure was confirmed by NMR. Yield was 83%.

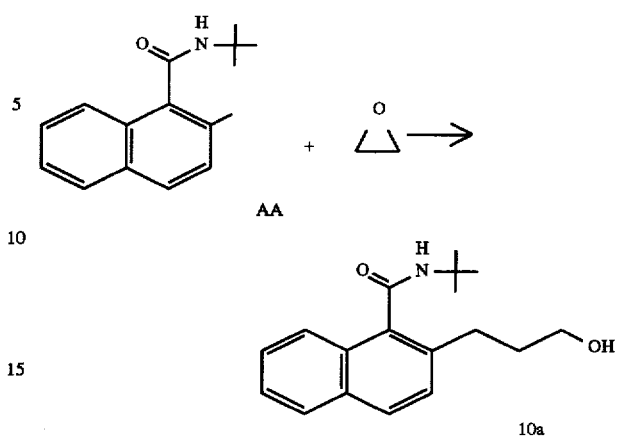

Then, a solution of 0.8 gm (3.317 mmol) of compound AA and 0.79 gm of TMEDA and 27 ml of THF was cooled to −78° C. in a dry ice/acetone bath. After the solution had cooled for 15 minutes at −78° C., 4.02 ml of a 1.69M solution of n-butyl lithium in hexane was added dropwise to the solution. A deep purple color resulted. The solution was then stirred at −78° C. for 1.5 hours. At this point, a solution of 0.292 gm (6.64 mmol) of ethylene oxide in THF (10% in THF) was added. After 15 minutes, TLC indicated that there was residual starting material. Accordingly, another equivalent of ethylene oxide was added. The reaction was monitored again and starting material was still seen so yet another 5 equivalents of ethylene oxide was added. The reaction was then allowed to warm to 0° C. and the purple color changed to a light green. The reaction mixture was poured into water, extracted with ether, washed with brine, dried over MgSO₄ and filtered. Solvent was removed under vacuum, yielding a yellow oil. The yellow oil was purified by flash chromatography using a 2 to 1 ether/hexane solution. Fractions 6–11 were collected cleanly and the solvent was removed under vacuum. Structure was confirmed by NMR. Yield was 42%.

Step 10b

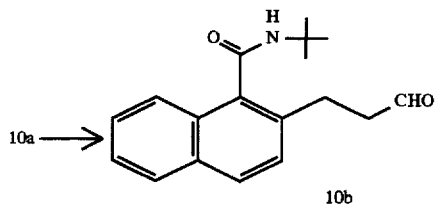

To a solution of 0.83 gm of pyridine and 15 ml of methylene chloride there was added 0.526 gm of chromium trioxide. The solid partially dissolved into an orange solution with a brown solid settling out. After 60 minutes, a solution of 0.25 gm of compound 10a in 4 ml of methylene chloride was added, dropwise. After 15 minutes, TLC indicated that no residual starting material was present. The mixture was poured into ether, washed twice with 1N NaOH, then sequentially with 1N HCl, saturated NaHCO₃ and brine, then dried over MgSO₄. The mixture was filtered and the solvent was removed in vacuum yielding a solid product which was then recrystallized from ether and hexane. The structure was confirmed by NMR. Yield was 72.5%.

Step 10c

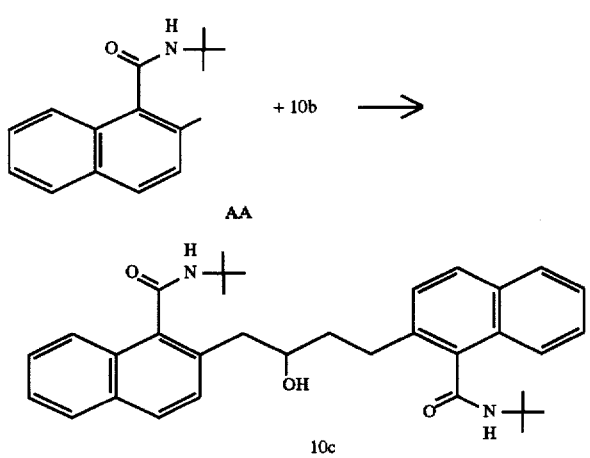

A solution of 0.136 gm (0.565 mmol) of compound AA and 0.132 gm of TMEDA in 10 ml THF was cooled to −78° C. in a dry ice/acetone bath. After the solution had stirred for 15 minutes at −78° C., 0.34 ml of a 1.69M solution of n-butyl lithium in hexane was added. A purple color developed and the solution stirred at −78° C. for 45 minutes. At this time, a solution of 0.08 gms (0.283 mmol) of compound 10b in 2 ml of THF was added. The solution was stirred for an additional 15 minutes at which time some residual starting aldehyde persisted. The reaction was allowed to warm to 0° C. and TLC did not indicate whether residual aldehyde still remained. The reaction mixture was allowed to warm to room temperature. After 10 minutes it was poured into water and extracted with ether. The extracts were washed with brine and dried over MgSO$_4$. The mixture was then filtered and the solvent was removed under vacuum and a yellow oil was recovered. This oil was purified by flash chromatography and the desired material was confirmed by NMR.

EXAMPLE 11

Preparation of

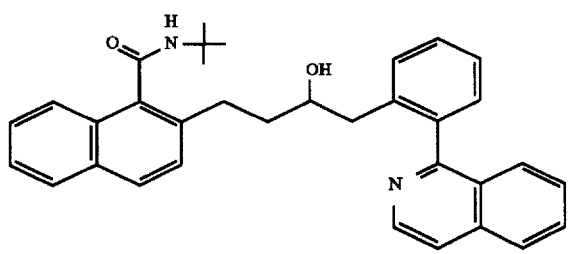

Step 11a

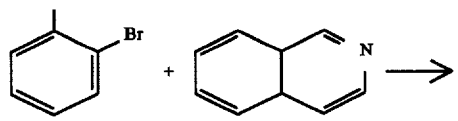

A solution was prepared of 21.37 gm (0.125 mol) of O-bromotoluene in 100 ml of ether. The solution was stirred and 1.75 gm of lithium wire was added. The mixture was allowed to stir at room temperature. As the lithium dissolved, the solution began to reflux spontaneously. After 1 hour the mixture was murky and brown with a white precipitate. She reaction was then allowed to stir for an additional 3 hours at which time 32.25 gm (0.25 mmol) of isoquinoline and 100 ml of toluene were added through the condenser. As the isoquinoline addition proceeded the solution turned blood red with a yellow precipitate and refluxed spontaneously. The mixture was no longer exothermic after about one-half of the isoquinoline had been added. When the addition was completed the condenser was replaced with a short path distillation apparatus, the reaction mass was concentrated down to 115 ml and reflux was continued for about 2.5 hours. At this time, TLC indicated that no bromotoluene material remained. The reaction was quenched with water and poured into additional water. Organic materials were extracted with ethyl acetate and washed with saturated NaHCO$_3$ and brine. A brown oil (49.01 gm) was collected, dried over MgSO$_4$ and purified by fractional distillation. The desired product distilled at 115°–120° C. Yield was 13.5 gm.

Step 11b

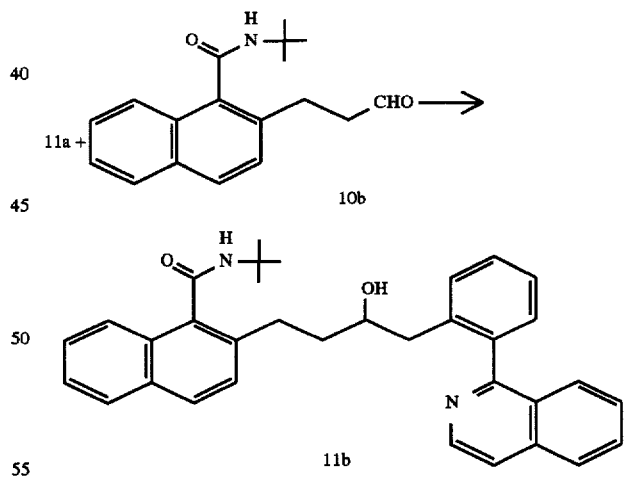

A solution of 0.465 gm of TMEDA in 20 ml of THF was cooled to −78° C. After 10 minutes 2.35 ml of a 1.7M solution of n-butyl lithium in hexane was added. The clear solution which resulted was stirred at −78° C. for 30 minutes at which time a solution of 0.85 gm (3.87 mmol) of compound 11a and 5 ml THF was added, dropwise. The solution gradually turned dark green and was allowed to warm to about −30° C. and stirred at that temperature for about an hour.

At the end of this one hour period, a solution of 0.30 gm (1.29 mmol) of compound 10b in 3 ml of THF was rapidly added. The solution immediately turned black and stirring was continued at −30° C. for another hour. The mixture was warmed to room temperature and stirring was continued for another hour. TLC indicated the presence of residual starting material so the mass was allowed to stir overnight at room temperature.

The reaction mass was poured into ether, washed sequentially with water and brine, then extracted with 1N HCl. The organic layer was separated, and the aqueous layer made basic (pH8) with saturated NaHCO$_3$ and extracted with ether. The second organic layer was dried over MgSO$_4$ and filtered. The solvent was removed under vacuum. The organic layer was purified by flash chromatography using 5:1 ether/hexane eluent. The more polar material was collected (0.05 g) and the desired material confirmed by NMR.

EXAMPLE 12

Preparation of

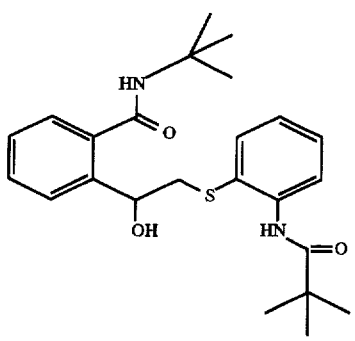

Step 12a

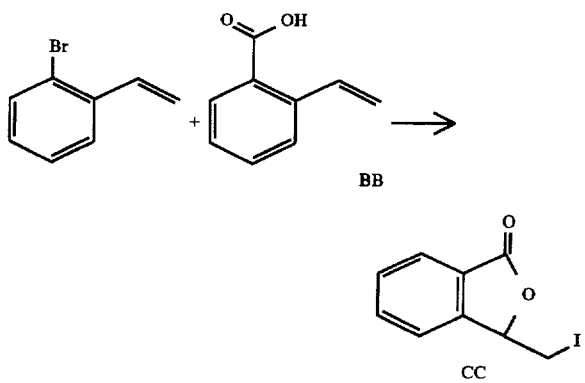

Compound CC was prepared in the following manner. Mg turnings (1.75 g, 0.072 g atom) were placed in an oven dried 250 ml 3 neck flask with condenser and addition funnel (all assembled hot). The entire apparatus was evacuated and filled with argon. The flask was charged with 10 ml of anhydrous THF and the addition funnel was charged with 8.0 gm (43.7 mmol) of 1-bromostyrene in 50 ml of anhydrous THF. Five (5) ml of the 1-bromostyrene solution was added to the Mg turnings and the mixture was heated to 65°–70° C. and the remainder of the solution was added over 1 hour. The mixture was heated an additional 30 min., then cooled to room temperature over 1 hour, then poured over crushed dry ice and the dry ice was allowed to evaporate. The mixture was made strongly acidic with 150 ml of 10% HCl solution. The organic phase was separated and the aqueous phase was extracted three times with ether. The combined organic phase was poured into 150 ml of 20% KOH solution, the solution was separated and the basic phase was filtered to remove polymer. The basic phase was then acidified with 10% HCl solution and extracted three times with 100 ml portions of ether. The extracts were combined, washed with 100 ml of brine and dried over Na$_2$SO$_4$. The solution was filtered and concentrated to a white solid which was recrystallized from chloroform/hexane solution to yield 6.44 g (66%) of 1-vinylbenzoic acid in two crops.

Then, iodine (4.12 g, 16.22 mmol) was added in a single portion to a degassed solution of 1.20 gm (8.11 mmol) of compound BB in 12 ml of acetonitrile. The solution was stirred for 1 hour, then poured into 50 ml of saturated sodium thiosulfate solution. The solution was extracted three times with 50 ml portions of ethyl acetate. The combined organic phases were washed sequentially with 40 ml portions H$_2$O, saturated NaHCO$_3$ solution and saturated sodium thiosulfate solution then dried over MgSO$_4$. The solution was filtered and concentrated to a yellow solid (1.87 g, 84% yield) which was recrystallized from ethanol.

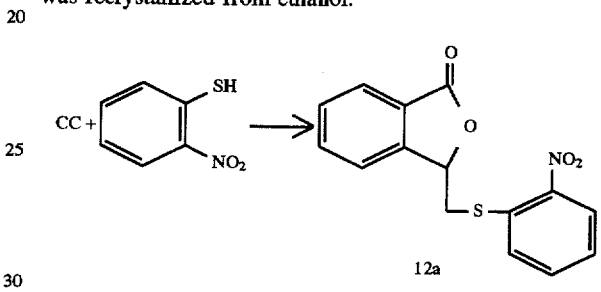

Then, to a degassed solution of 0.65 g, (4.22 mmol) of 1-mercaptonitrobenzene in 15 ml of ethanol was added, dropwise, 0.28 g (4.2 mmol) of KOH in 1.5 ml H$_2$O. The resultant brown solution was stirred for 10–15 minutes at room temperature. The solution was cooled to 0° C. and 1.10 g (4.02 mmol) of compound CC in 10 ml of THF was added, dropwise. The mixture was stirred at room temperature for 21 hours, then poured into 70 ml of H$_2$O and the solution was extracted three times with 50 ml portions CH$_2$Cl$_2$. The combined organic phases were washed with 50 ml of H$_2$O and brine and dried over MgSO$_4$. The solution was then filtered and concentrated under vacuum. The residue was purified by flash chromatography (125 g silica gel; 1% ethyl acetate/chloroform) to yield 0.58 g (48% yield) of yellow solid.

Step 12b

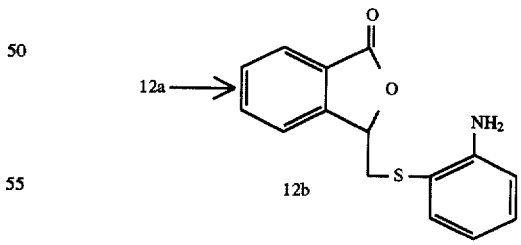

A mixture of 200 mg, (0.67 mmol) of compound 12a and 368 mg (0.73 mmol) of Fe$_3$(CO)$_{12}$ in 40 ml of benzene and 0.15 ml of MeOH was heated to reflux for 5.5 hours. The reaction mixture was then cooled and filtered through Celite and the filter pad was washed with 50 ml of benzene/MeOH. The solution was concentrated under vacuum and the orange residue was purified by flash chromatography (40 g silica: 0.25–0.5% ethyl acetate/CH$_2$Cl$_2$). The product (149 mg, 81% yield) was isolated as a colorless, viscous oil.

Step 12c

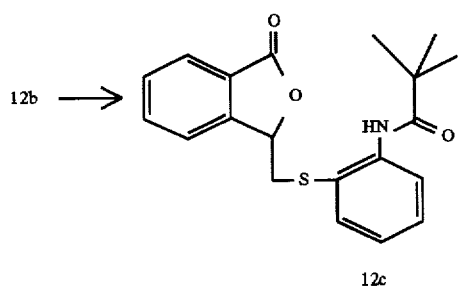

To a solution of 149 mg (0.55 mmol) of aniline 12b in 5 ml $CH_2Cl_2$ cooled to 0° C., was added 74 µl, (0.61 mmol) of pivaloyl chloride, followed by 98 µl (1.21 mmol) of pyridine. The reaction was stirred for 20 hours at room temperature and then poured into 20 ml of $H_2O$. The mixture was separated and the aqueous phase was extracted once with a 20 ml portion of $CH_2Cl_2$. The combined organic phases were washed with 20 ml portions of 5% $KHSO_4$ and saturated $NaHCO_3$ solution and dried over $MgSO_4$. The solution was then filtered and concentrated to a slightly yellow oil which was purified by flash chromatography (30 g silica; 20% ethyl acetate/hexane) to yield 174 mg (89% yield) of product as a colorless viscous oil.

Step 12d

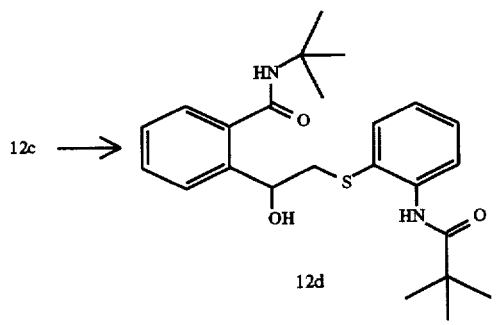

To a solution of 96 µl (0.92 mmol) of t-butylamine in 2 ml of dichloroethane, cooled to 0° C., was added 0.46 ml of a 2.0M solution of trimethyl aluminum (0.92 mmol) in toluene, dropwise, over 5 minutes and the solution was then stirred for 45 minutes at room temperature. A solution of 65 mg (0.18 mmol) of compound 12c in 2 ml of dichloroethane was added, dropwise, and the mixture was heated to 65° C. for 18 hours. The reaction mixture was then cooled and quenched with 10 ml of saturated $NH_4$ Cl solution. The mixture was extracted with three 10 ml portions of ethyl acetate and the combined organic phases were dried over $MgSO_4$. The solution was filtered and concentrated and the residue purified by flash chromatography (15g silica; 1.5–3% ethyl acetate/$CH_2Cl_2$) to yield 40 mg (51% yield) of the product as a white solid.

EXAMPLE 13

Preparation of

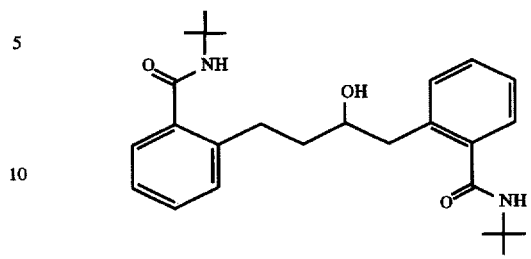

Step 13a

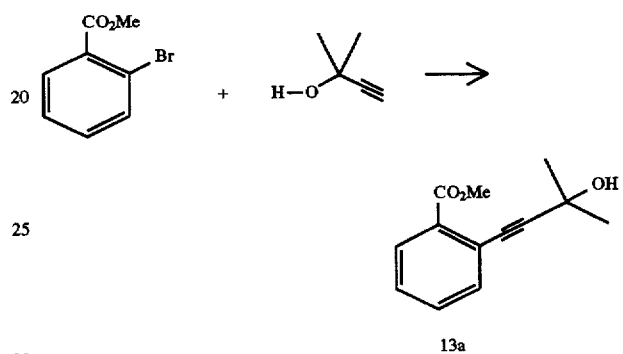

A mixture of 4.0 g (18.61 mmol) of 1-bromomethylbenzoate, 2.2 ml (22.34 mmol) of 2-methyl-3-butyne-2-ol, palladium catalyst (6.1 mg), cuprous iodide (6.2 mg), and triphenylphosphine (12.3 mg) in 19 ml of triethyl amine was heated to reflux for 5 hours during which time the reaction mixture went from a yellow solution to brown with a thick precipitate. The mixture was cooled and filtered and the solid was washed with 50 ml of ether. The filtrate was concentrated under vacuum to an orange oil which was purified by flash chromatography (200 g silica, 25–35% ethyl acetate/hexane) to yield 2.97 g (73%) of product as a yellow viscous liquid.

Step 13b

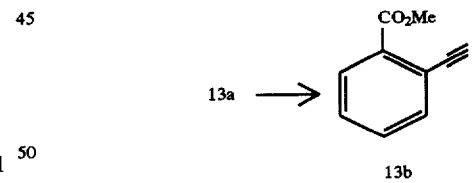

To a solution of 2.97 gm (13.62 mmol) of compound 13a in 25 ml of toluene, was added 0.033 gm (1.10 mol) of an 80% dispersion of sodium hydride in mineral oil. The mixture was heated to reflux during which time the toluene was allowed to distill off. The reaction was cooled when the still head temperature reached 105° C. The solution was filtered and the solid washed with 20 ml of toluene. The filtrate was concentrated under vacuum, and the residue was dissolved in 100 ml of $CH_2Cl_2$. The organic solution was washed with 50 ml portions of dilute $NaHCO_3$ solution and $H_2O$. The organic phase was dried over $MgSO_4$, filtered and concentrated to a brown oil. The product was isolated by kugelrohr distillation (80°–85° C., 0.5 torr) to yield 1.10 g (50%) of product as a yellow-orange liquid.

Step 13c

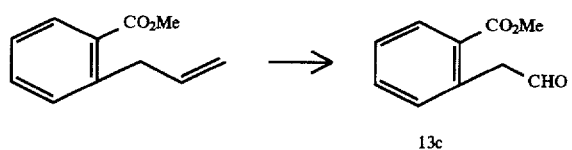

To a solution of 2.50 g (14.19 mmol) of 2-propenyl-methylbenzoate in 50 ml of dioxane and 16 ml H$_2$O was added 1.44 ml of a 2.5% solution of osmium tetraoxide in t-butyl alcohol. The mixture was stirred for 15 minutes during which time it turned from colorless to brown. NaIO$_4$ (6.07 g, 28.38 mmol) was added in small portions over 30 minutes and the mixture was stirred at room temperature for 2.5 hours during which time a thick white precipitate formed. The reaction mixture was poured into 75 ml of H$_2$O, extracted with three 60 ml portions of ethyl ether, and the combined organic phase was washed with 100 ml of H$_2$O and brine and dried over MgSO$_4$. The solution was filtered and concentrated under vacuum to a tan oil which was purified by flash chromatography (100 g silica, 30% ethyl ether/hexane) to yield 1.25 g (50%) of product as a light yellow liquid.

Step 13d

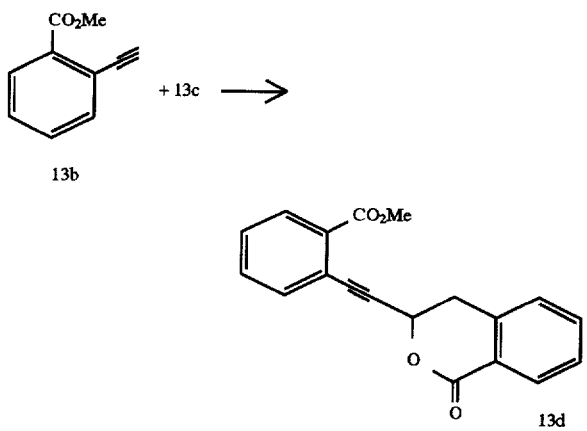

To a solution of 146 microliters of diisopropyl amine (1.04 mmol) in 9 ml of anhydrous THF cooled to –78° C. was added 0.59 ml of a 1.6M solution of n-butyl lithium, dropwise. The mixture was warmed to 0° C. for 20 minutes then cooled back to –78° C. A solution of 151 mg (0.94 mmol) of compound 13b in 1 ml of THF was added dropwise over 5 minutes, producing a yellow solution. The mixture was stirred at –78° C. for 45 minutes and a solution of 140 mg (0.79 mmol) of compound 13c in 1 ml of THF was added dropwise over. 5 minutes. The mixture was stirred for 1.5 hours at –78° C., warmed to room temperature for 1.5 hours and then quenched with 10 ml of dilute NH$_4$Cl solution.

The mixture was diluted with 20 ml of H$_2$O and extracted with three 25 ml portions of ether. The organic phase was washed with 25 ml portions of 10% citric acid, H$_2$O, and brine and dried over MgSO$_4$. The solution was filtered and concentrated under vacuum to a brown oil. The residue was purified by flash chromatography (50 g silica, 20–30% ethyl acetate/hexane) to yield 52 mg (22%) of product as a yellow white solid. A sample was recrystallized from ether/hexane.

Step 13e

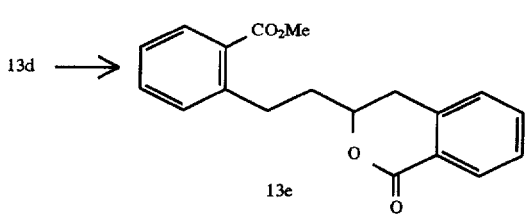

A suspension of 120 mg (0.39 mmol) of compound 13d and 5% palladium on carbon (96 mg) in 12 ml of ethyl acetate was stirred under an atmosphere of H$_2$ for 1.5 hours. The mixture was filtered through a pad of Celite which was washed with 25 ml of ethyl acetate and the solution was concentrated to a yellow viscous oil. The material was purified by flash chromatography (50 g of silica, 25–35% ethyl ether/hexane) to yield 109 mg (89%) of product as a colorless viscous oil.

Step 13f

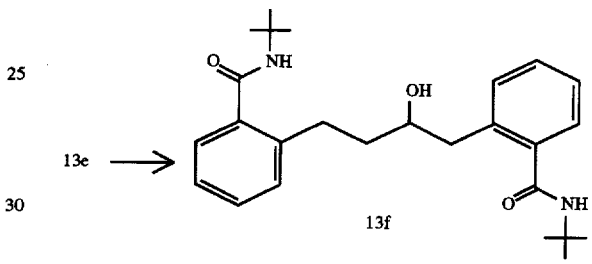

To a solution of 0.27 ml (2.58 mmol) of t-butyl amine in 6 ml of toluene at 0° C. was added 1.28 ml of a 2M solution of trimethylaluminum in toluene, dropwise over 5 minutes. The mixture was stirred for 45 minutes at room temperature and a solution of 85 mg (0.26 mmol) of compound 13e in 0.5 ml toluene was added dropwise. The solution was heated to 100° C. for 5 hours, cooled and quenched with saturated NH$_4$Cl solution. The aqueous phase was extracted three times with 20 ml portions of ethyl acetate. The combined organic phase was dried over MgSO$_4$, filtered and concentrated to a viscous yellow oil. The residue was purified by flash chromatography (40 g silica, 20–40% ethyl acetate/hexane) to yield 91 mg (83%) of product as a colorless viscous oil.

EXAMPLE 14

Preparation of

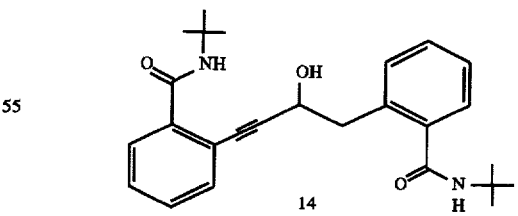

To a solution of 0.24 ml (2.3 mmol) of t-butyl amine (0.24 ml, 2.3 mmol) in 4 ml toluene at 0° C. was added 1.4 ml of a 2.0M solution of trimethylaluminum in toluene, dropwise over 5 minutes. The mixture was stirred for 45 minutes at room temperature and a solution of 70 mg (0.23 mmol) of compound 13d in 2 ml toluene was added, dropwise. The solution was heated to 70° C. for 24 hours, cooled and quenched with saturated NH₄Cl solution. The aqueous phase was extracted three times with 20 ml portions of ethyl acetate. The combined organic phase was dried over MgSO₄, filtered and concentrated to a viscous orange oil. The residue was purified by flash chromatography (20 g silica, 20–40% ethyl acetate/hexane) to yield 31 mg (32%) of product 14 as a colorless glass.

EXAMPLE 15

Preparation of

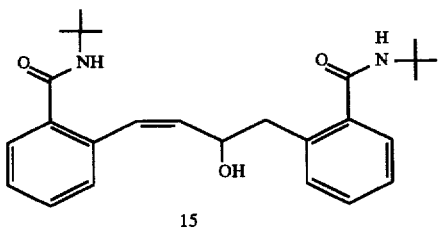

15

A suspension of 20 mg (0.0489 mmol) of compound 14, 20 μl of quinoline and Lindlar catalyst (6.0 mg) in 3 ml of ethyl acetate was stirred under an atmosphere of H₂ for 4 hours. The mixture was then filtered through Celite and the filter pad washed with 20 ml ethyl acetate. The solution was concentrated under vacuum and purified by flash chromatography (15 g silica, 25–40% ethyl acetate/hexane) to yield 17 mg (84%) of the cis isomer of the product 15 as a white solid.

EXAMPLE 16

Preparation of

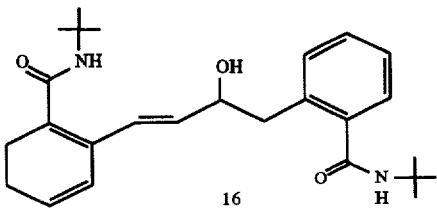

16

Step 16a

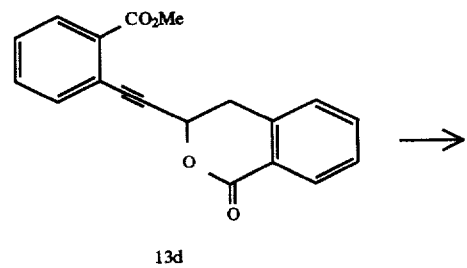

13d

-continued

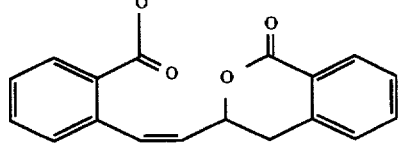

16a

A suspension of 236 mg (0.77 mmol) of compound 13d, quinoline (60 μl), and Lindlar catalyst (55 mg) in 15 ml of ethyl acetate was stirred under an atmosphere of H₂ for 1 hour. The mixture was filtered through Celite and the filter pad washed with 50 ml ethyl acetate. The solution was concentrated to a yellow oil which was purified by flash chromatography (75 g of silica gel, 15–30% ethyl acetate/hexane) to yield a white solid which was triturated with ethyl ether/hexane (to remove traces of quinoline) to yield 208 mg (87%) of product 16a as a white solid.

Step 16b

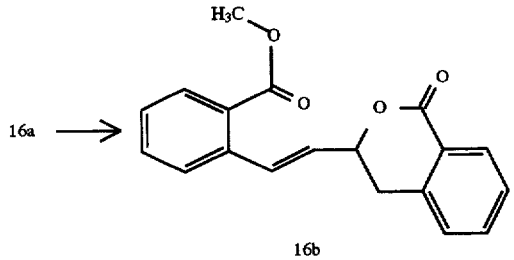

16a →

16b

A solution of 150 mg (0.49 mmol) of compound 16a, 6.5 mg of AIBN, and 80 microliters of thiophenol in 12 ml of benzene was heated to reflux for 4 hours. After 2.5 hours, another portion of AIBN (6 mg) was added. The solution was cooled and concentrated. The residue was purified by flash chromatography (80 g silica, 10–30% ethyl acetate/hexane) to yield 112 mg (77%) of product as a white solid.

Step 16c

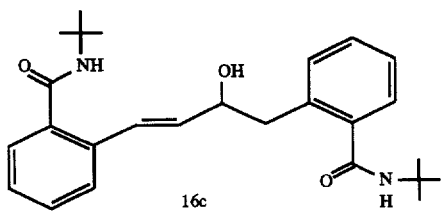

16b →

16c

To a solution of 0.17 ml (1.6 mmol) of t-butyl amine in 3 ml of toluene at 0° C. was added 0.81 ml of a 2.0M solution of trimethylaluminum (1.6 mmol), dropwise over 5 minutes. The mixture was stirred for 45 minutes at room temperature and 50 mg (0.16 mmol) of compound 16b in 1 ml of toluene was added dropwise. The solution was heated to 70° C. for 5 hours, cooled and quenched with saturated NH₄Cl solution. The aqueous phase was extracted three times with 20 ml portions of ethyl acetate. The combined organic phase was dried over MgSO₄, filtered and concentrated to a viscous orange oil. The residue was purified by flash chromatography (15 g of silica, 20–45% ethyl acetate/hexane) to yield 33 mg (48%) of product as a white solid.

EXAMPLE 17

(Comparative: not part of the invention)

Preparation of

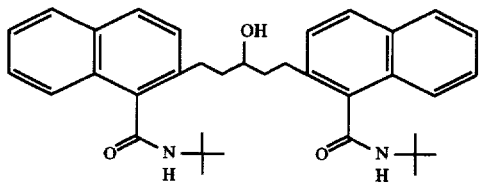

Step 17a

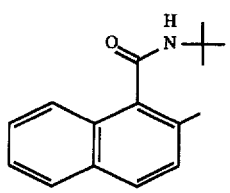

AA

Compound AA was prepared in the following manner. A heterogeneous mixture of 2 gm (10.75 mmol) of 2-methyl naphthoic acid in toluene was cooled to 0° C. and oxalyl chloride was added, dropwise, followed by dropwise addition of 0.236 gm of dimethylformamide (DMF). As the DMF was added, gas was vigorously evolved and the solid 2-methyl naphthoic acid began to go into solution. After 5 minutes, the reaction mixture was allowed to warm to room temperature. The solution was clear and golden with a small amount of white precipitate. After 20 minutes the precipitate had dissolved into the solution and the reaction was monitored by infrared analysis. The reaction mass was concentrated under vacuum. As the oxalyl chloride evaporated, a large amount of a white solid settled out. The solution could not be further concentrated due to the presence of the solid. The mixture was cooled to 0° C. and 1.65 gm of t-butylamine was added. A fine white precipitate settled out. The bath was then removed and after 15 minutes at room temperature the reaction mass was poured into water and extracted with ethyl acetate. The organic phases were collected, washed with brine, and dried over MgSO$_4$. The solvent was removed under vacuum. The solid was purified by column chromatography using a 2-1 hexane to ether solution as the eluant. Following chromatography the product was recrystallized from an ether/hexane mixture. Structure was confirmed by NMR. Yield was 83%.

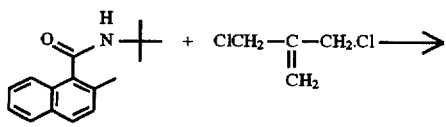

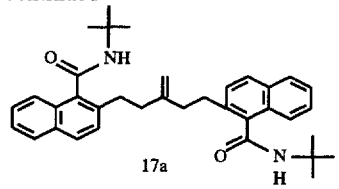

Then, to a solution of 600 mg (2.49 mmol) of compound AA and 0.75 ml of tetramethylethylenediamine in 15 ml of anhydrous THF, cooled to −78° C., was added 3.11 ml of a 1.6M solution of n-BuLi in hexane, dropwise, over 10 minutes. The solution was stirred at −78° C. for 45 minutes and 0.14 ml (1.25 mmol ) of 1,3-dichloroisobutene was added, dropwise. The mixture was allowed to warm to −30° C., then poured into 30 ml of dilute NH$_4$Cl solution. The aqueous phase was extracted with three 25 ml portions of ethyl acetate. The combined organic phase was washed with 30 ml portions of 10% citric acid solution, H$_2$O, and brine, then dried over MgSO$_4$. The solution was filtered and concentrated to a yellowish white solid which was purified by flash chromatography (100 g of silica, 1.5–10% ethyl acetate/CH$_2$Cl$_2$) to yield 370 mg (56%) of product as a white solid.

Step 17b

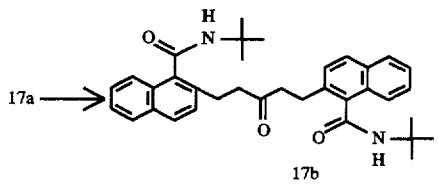

To a solution of 60 mg (0.11 mmol) of compound 17a in 2 ml dioxane and 0.5 ml H$_2$O, was added one drop of 2.5% OsO$_4$ solution in t-butyl alcohol. The mixture was stirred for 15 minutes and 48 mg (0.22 mmol) of NaIO$_4$ was added in one portion. The mixture was stirred at room temperature for 20 hours, then poured into 15 ml of H$_2$O and the aqueous mixture was extracted with three 15 ml portions of ether. The combined organic phase was washed with 10 ml portions of H$_2$O and brine, then dried over MgSO$_4$. The solution was filtered and concentrated to a viscous yellow oil which was purified by flash chromatography (10 g silica, 30–40% ethyl acetate/hexane) to yield 40 mg (67%) of product as a white solid.

Step 17c

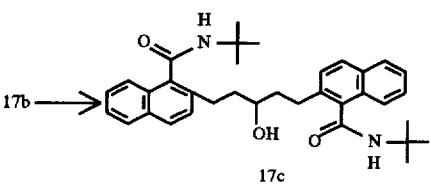

To a solution of 35 mg (0.065 mmol) of compound 17b in 2 ml of MeOH was added 3 mg (0.078 mmol) of NaBH$_4$ in one portion. The reaction was stirred for 15 minutes at room temperature, then poured into 10 ml of saturated NaHCO$_3$ solution. The aqueous phase was extracted with two 15 ml portions of ethyl acetate, the combined organic phase was washed with 10 ml of H$_2$O and dried over MgSO$_4$. The organic phase was then filtered and concentrated to a white foam which was purified by flash chromatography (10 g of silica, 30–40% ethyl acetate/hexane) to yield 29 mg (83%) of product as a white solid.

EXAMPLE 18

Preparation of

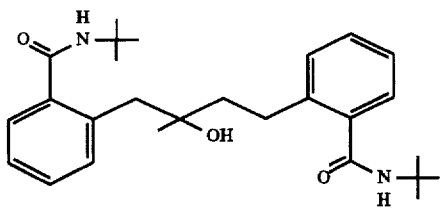

Step 18a

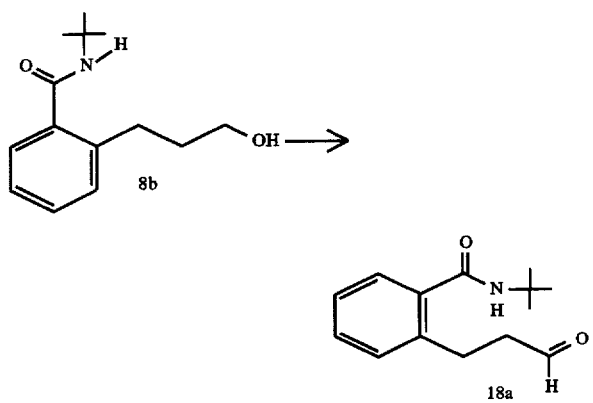

Chromium trioxide (14.4 gm, 144 mmol) was added slowly to 23.3 ml of pyridine and the mixture was diluted with 300 ml $CH_2Cl_2$. The alcohol 8b (6.16 gm, 26.2 mmol) was added to the chromium trioxide solution at 25° C. and the reaction was stirred for 2 hours. After dilution with ether, the reaction was washed twice with 150 ml of 1N HCl, 1N NaOH, saturated $NaHCO_3$, and brine. Drying over $MgSO_4$ and concentration afforded a yellow oil, which chromatographed on silica (1:1 ether/hexane), yielding 4 gm (65%) of aldehyde 18a as a white amorphous solid. The structure was confirmed by NMR.

Step 18b

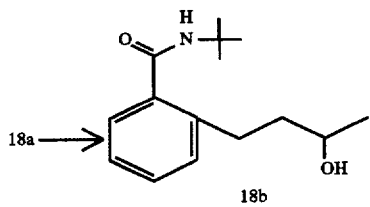

To 764 mg (6.42 mmol) of methyl magnesium bromide in 10 ml of dry ether was added 500 mg (2.14 mmol) of compound 18a in 15 ml of dry ether at 0° C. resulting in a milky white solution. The ice bath was removed and the mixture was warmed to room temperature. After 1 hour at room temperature, TLC indicated that some starting material remained. Another equivalent (119 mg) of methyl magnesium bromide was added and the solution changed from milky white to clear. The reaction was quenched with ice and 1N HCl, extracted with ethyl acetate and ether, washed with brine, then dried over $MgSO_4$. Concentration under vacuum yielded 576 mg of a clear oil which was then purified by flash chromatography ($SiO_2$:2/1 ether-hexane) yielding 358 mg (76%) of product.

The structure was confirmed by 'HNMR.

Step 18c

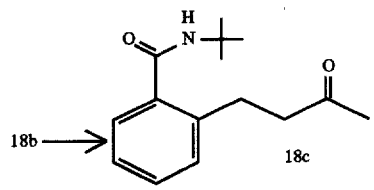

$CrO_3$ (580 mg–5.8 mmol) was added to 1 mL of pyridine and a paste formed with exotherm. Three ml of $CH_2Cl_2$ were added and the mixture was stirred for 10 minutes more. An additional 12 ml of $CH_2Cl_2$ were added (total=15 ml) and (360 mg, 1.4 mmol) of compound 18b in 3 ml of $CH_2Cl_2$ was added, dropwise. The solution turned dark. After 1 hour, TLC indicated that about 20% of the starting material remained. An additional 2 equivalents of the $CrO_3$/pyridine reagent in 3 mL of $CH_2Cl_2$ was added. The reaction was essentially complete after 3 more hours. The reaction mixture was diluted with ether and $CH_2Cl_2$ and filtered through $SiO_2$ and concentrated under vacuum to yield 309 mg of a white solid, which was purified by flash chromatography ($SiO_2$, 1:1 ether/hexane) yielding 228 mg (66%) of the product as a white solid.

Step 18d

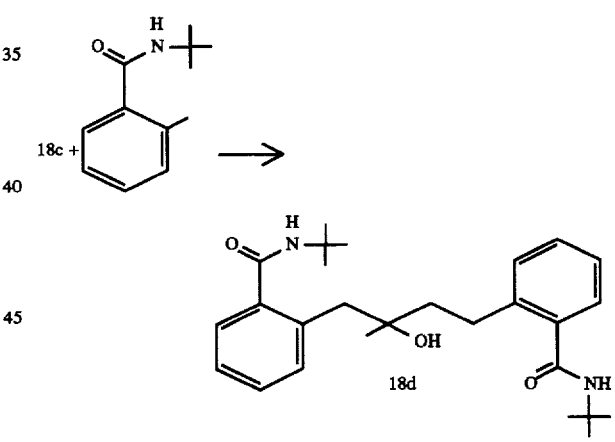

To 281 mg (1.47 mmol) of N-t-butyl toluamide, which had been pumped down on highvac equipment, was added 341 mg (2.93 mmol) of TMEDA and 8 ml of THF. The mixture was cooled to –78° C. using a dry ice/acetone bath, and s-butyl lithium (2.7 ml, 2.93 mmol) was added dropwise. The color turned to deep orange. The mixture was stirred at –78° C. for 45 minutes, at which time 165 mg (0.667 mmol) of compound 18c in 5 ml of THF was added via cannula. The color changed to light orange. The temperature was allowed to rise to –30° C. at which point the color disappeared. The reaction was quenched with 1N HCl, washed with brine, extracted with $CH_2Cl_2$ and dried over $MgSO_4$. Concentration under vacuum yielded 550 mg of clear oil. The oil was purified by flash chromatography using initially 1:1 ether/hexane, changing to 2:1 ether/hexane solvent, yielding 41 mg of product (14% yield).

EXAMPLE 19

Preparation of

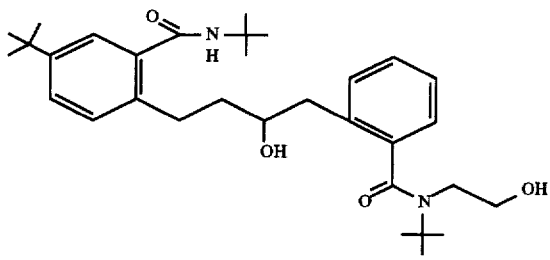

Step 19a

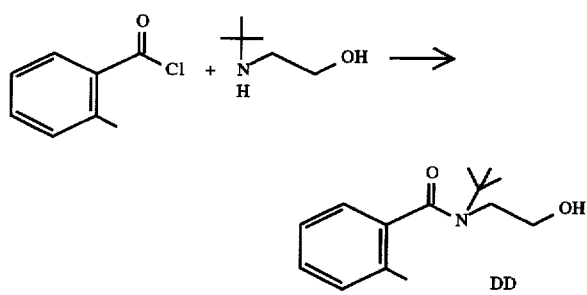

Compound DD was prepared in the following manner. To a solution of 4.97 gm (0.043 mole) of hydroxyethyl-t-butyl amine and 18 ml of trimethyl amine in 100 ml of $CH_2Cl_2$, cooled to 0° C., was added 11 ml (0.085 mole) of o-toluoyl chloride, dropwise. The reaction mixture was allowed to warm to room temperature and was stirred for 24 hours. The reaction was then quenched by pouring the reaction mixture into 100 ml of $H_2O$ and extracted once with 100 ml of $CH_2Cl_2$. The organic phase was washed with 100 ml portions of $H_2O$, 10% citric acid, $H_2O$, and saturated $NaHCO_3$, then dried over $MgSO_4$. The dried solution was filtered and concentrated under vacuum to a viscous yellow oil which was dissolved in 100 ml of 90% aqueous methanol. To this solution was added 5.5 ml of 45% KOH and the mixture was kept at room temperature for 45 minutes. It was then concentrated under vacuum, diluted with 100 ml of $H_2O$ and extracted three times with 100 ml portions of diethyl ether. The combined organic phases were dried over $MgSO_4$, then filtered and concentrated under vacuum to a light yellow oil. This oil was dissolved in a 30% ethyl acetate/hexane mixture. The product was crystallized from this solution in two crops to yield 6.5 gm (64% yield).

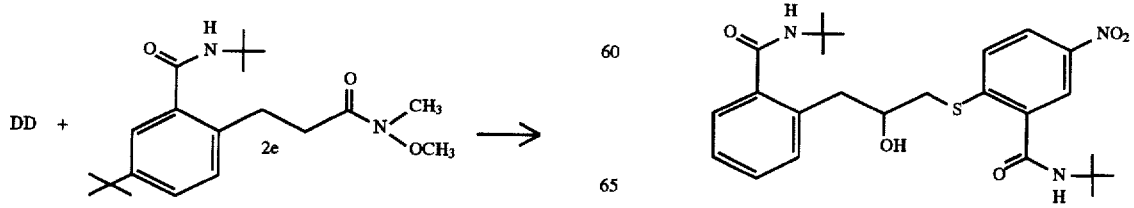

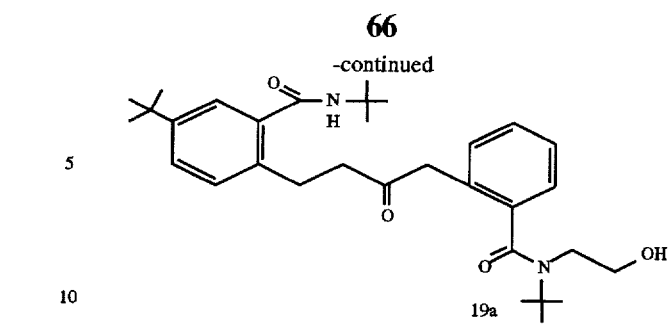

Then, s-Butyl lithium (1.34 ml, 1.34 mmol) was added to a solution of 0.158 gm (0.67 mmol) of compound DD and 28 μl of diisopropyl amine in THF at −78° C. A red color started to develop after about 70 μl of s-butyl lithium had been added. After all of the s-BuLi was added, solution became deep blue. The mixture was stirred at −78° C. for 1 hour, then 0.117 gm (0.335 mmole) of compound 2e in 1 ml of THF was added, dropwise. After about 30 minutes the solution became less colored (deep blue changed to very light blue). The reaction mixture was quenched 40 minutes later. The product was purified by flash chromatography. The chromatography was carried out twice; first with 70:30 methylene chloride/ethyl acetate, then with 80:20 methylene chloride/acetone. The yield was 87 mg (50%) of product.

Step 19b

19a ⟶

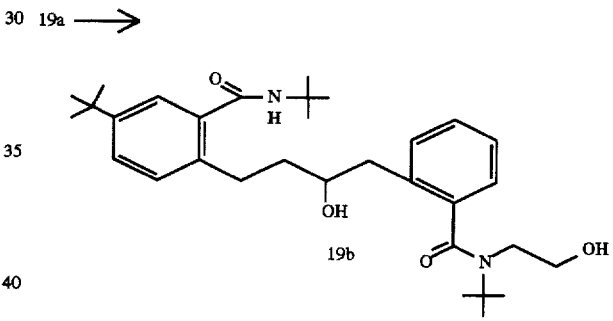

$NaBH_4$ (13.5 mg, 0.3 mmol) was added to a solution of 0.8 gm(0.15 mmol) of compound 19a in 2 ml of EtOH at room temperature and the solution was stirred for 0.5 hour. TLC analysis showed reaction was complete. The mixture was then quenched with $H_2O$ and extracted with ethyl acetate and the organic phase was dried over $MgSO_4$. Removal of solvent under vacuum yielded 0.077 g of a white solid. Purification by flash chromatography using $SiO_2$ with 70% $CH_2Cl_2$/30% ethanol solvent, yielded 44 mg (78.7%) of clean product. 'HNMR confirmed the structure.

EXAMPLE 20

Preparation of

Step 20a

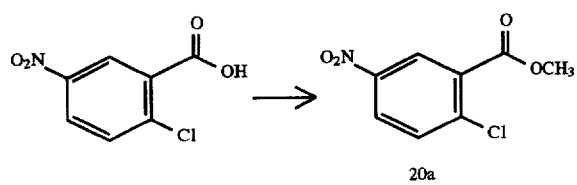

A mixture of 10 g (50 mmol) of 1 chloro-4-nitrobenzoic acid in 100 ml of 3% HCl in methanol was stirred at room temperature for 1 hour then heated to reflux for a total of 5 hours. At this time the reaction was substantially complete. It was cooled and concentrated under vacuum to a yellow white solid which was dissolved in ethyl acetate, washed sequentially with saturated NaHCO₃, water and then brine. The extract was dried over MgSO₄, concentrated under vacuum to 9.2 g (45 mmol, 85%) of a white solid. Structure of the solid was confirmed by NMR.

Step 20b

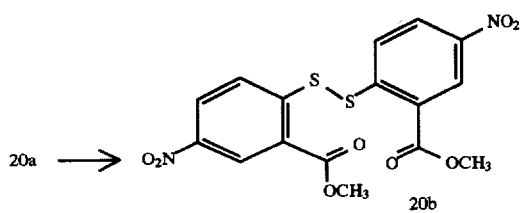

A solution of 5 g (23.2 mmol) of compound 20a in 50 ml of DMSO was reacted with NaSH at 50° C. A large quantity of solid formed. An additional 20 ml of DMSO was added and the reaction mixture was heated to 80° C. A dark brown mixture was formed and after 6 hours TLC indicated that all of the starting material had been consumed. The mixture was allowed to cool slowly and was stirred over a weekend. A brown sludge was poured slowly into water while stirring, yielding a yellow precipitate. The precipitate was filtered out, dissolved in hot ethyl acetate, reduced under vacuum to 400 ml volume, then purified by flash chromatography (10% ethyl acetate/40% hexane/methylene chloride). No separation occurred and the material was chromatographed once again using 20% hexane/methylene chloride. A yield of 1.75 g (36%) of the disulfide product was recovered. The structure was confirmed by NMR.

Step 20c

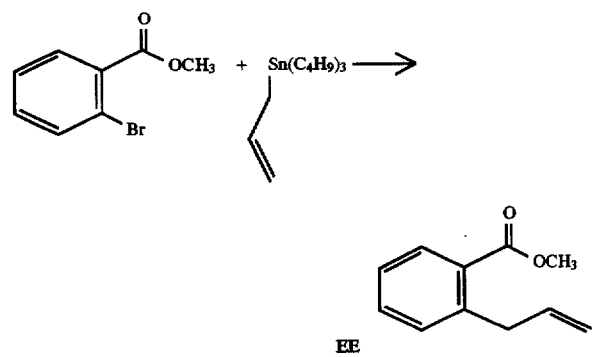

Compound EE was prepared in the following manner. A solution of 6.0 ml (41.71 mmol) of 1-bromo methylbenzoate and 16 ml (51.61 mmol) of tributylpropenyl tin in 15 ml of benzene was heated to 100° C. and allowed to sit at that temperature overnight in a sealed tube. In the morning the solution was filtered twice through a silica gel plug with hexane, then combined with an equal amount of the product of another run of the same reaction. The combined masses totaled 50.5 g. A portion of this product (10 g) was fractionally distilled at 2 mm and 4 fractions were collected. The distilled products were combined and purified by flash chromatography using a 5% ether/hexane to 10% ether/hexane gradient. Yield was 5.1 gm.

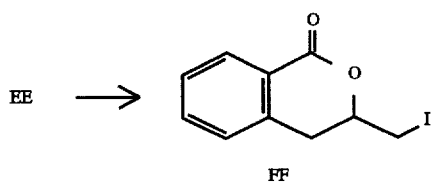

Compound FF was prepared in the following manner. To a mixture of 1.1 gm (6.28 mmol) of compound EE and 20 ml of acetonitrile at room temperature was added 3.0 g (12.13 mmol) of iodine. Reaction was completed in 45 minutes and the reaction mixture was poured into saturated sodium NaHSO₃, extracted twice with ethyl acetate, washed again with sodium NaHSO₃ and dried over MgSO₄. Concentration under vacuum yield 1.7 g of amber oil (94%). Structure was confirmed by NMR.

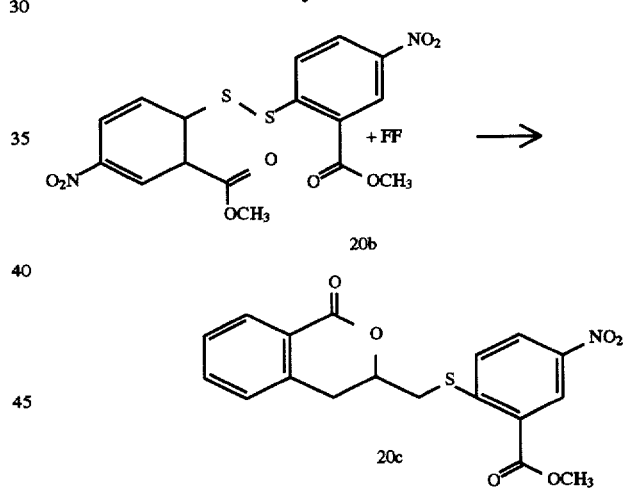

Then, a solution was prepared of 1.54 g (3.63 mmol) of compound 20b in 40 ml of DMF with heating. The solution was then cooled in an ice bath. Sodium hydroxide was added, whereupon the solution turned dark red. It was stirred for one hour at room temperature. The solution was then cooled to 0° and 2.16 g (7.5 mmol) of compound FF in 5 ml of ethanol was added and the reaction mixture was warmed to room temperature. After two hours of stirring, TLC showed all compound 20b had reacted. The mixture was poured into 1N HCL and extracted twice with ethyl acetate. The organic layers were washed sequentially with water and brine, dried over MgSO₄ and concentrated under vacuum. A crude weight of 4 g was recovered and purified by flash chromatography, in 33% yield, using methylene chloride. NMR confirmed the structure except that an ester interchange had taken place and the ester was now the ethyl ester.

Step 20d

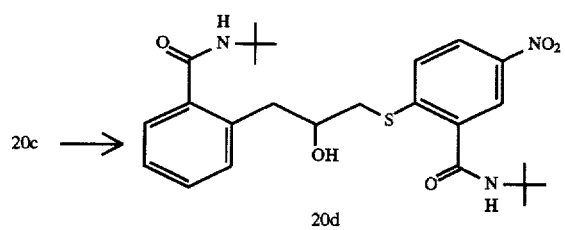

To a solution of 0.63 ml (1.26 mmol) of trimethylaluminum in 2 ml of toluene at 0° C. was added 0.13 ml (1.24 mmol) of t-butyl amine. The temperature was increased to room temperature and the mixture was stirred for 1 hour. Compound 20c (0.94 gm/0.225 mmol) in toluene was added and the mixture was heated to reflux. After 15 minutes, TLC indicated that all compound 20c had been consumed forming two products. After another 30 minutes of heating, the reaction was complete. The reaction mixture was poured into water, extracted twice with ethyl acetate, dried over $MgSO_4$ and concentrated under vacuum. Purification by flash chromatography (50% ethyl acetate/methylene chloride) yielded 0.63 gm (51%) of product. The structure was confirmed by 'HNMR.

EXAMPLE 21

Preparation of

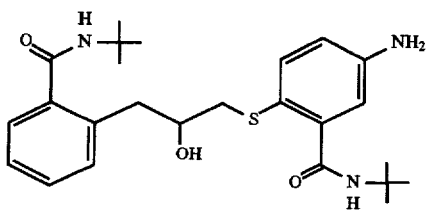

Step 21a

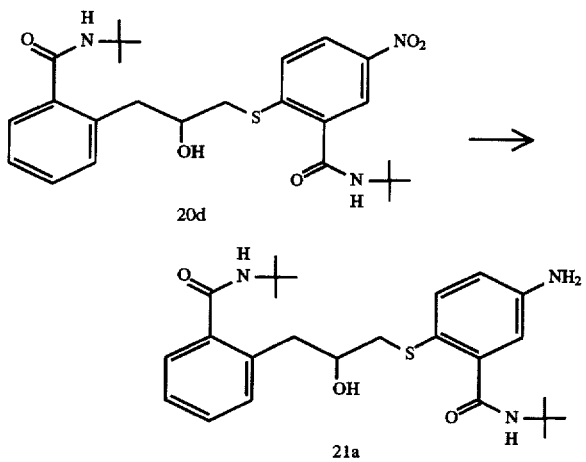

A solution of 0.03 g (0.061 mmol) of compound 20d in ml of glacial acetic acid was treated with 20 mg of metallic zinc at room temperature. No reaction was noted after one hour so an additional 20 mg of zinc was added. The reaction was complete after 1.5 additional hours. The product was filtered through Celite, concentrated under vacuum, dissolved with ethyl acetate, washed with saturated $NaHCO_3$, dried over $MgSO_4$ and concentrated by vacuum. Purification by flash chromatography, using 50% ethyl acetate/hexane, yielded 7.6 mg of product. Structure was confirmed by NMR.

EXAMPLE 22

Preparation of

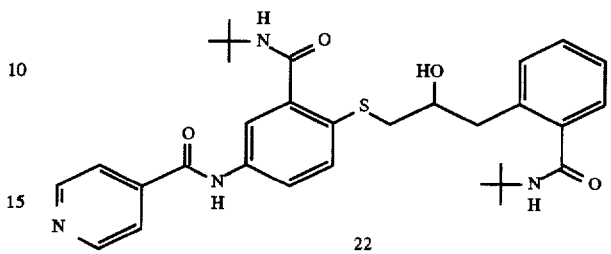

A solution of 0.37 g (0.082 mmol) of compound 21a and 17 microliters of pyridine in 0.5 ml of methylene chloride was cooled to −15° C. and reacted with 0.18 gm (0.103 mmol) of 3-pyridine carboxylic acid chloride hydrochloride salt. After 30 minutes, clean conversion to a more polar product had taken place. The reaction mixture was poured into water, extracted twice with ethyl acetate, washed with water, then brine and dried over $MgSO_4$. The extract was concentrated under vacuum to yield 30 mg of a yellow solid. The yellow solid was purified by flash chromatography (5% methanol/methylene chloride) yielding 0.27 gm (59%) of a yellow white solid. The structure was confirmed by NMR.

EXAMPLE 23

Preparation of

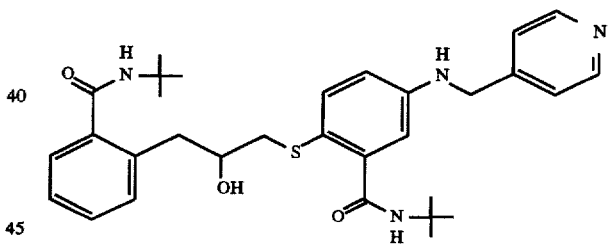

A solution of 0.5 g (0.108 mmol) of compound 21a, 10 μl of 4-pyridine-carboxaldehyde (0.105 mmol) in 1 ml of methanol and 0.5 ml of 6% hydrochloric acid in methanol was treated at room temperature with $NaCNBH_3$ and was allowed to stir overnight. By morning, a small amount of a polar compound had formed but the mixture was still mostly starting material. An additional 20 μl (2 equivalents) of the 4-pyridine-carboxaldehyde was added and the reaction was allowed to continue stirring at room temperature. After 4 additional hours, TLC indicated that all starting material had been consumed and 2 polar products had been formed. After one more hour of stirring, the reaction mixture was poured into 1N NaOH and extracted twice with ethyl acetate. The extract was dried over $Na_2SO_4$ and concentrated under vacuum. Flash chromatography using ethyl acetate yielded 29 mg of a first fraction and 14 mg of a second fraction. NMR confirmed the structure of the larger fraction to be the desired compound. This product was repurified by flash chromatography (3% methanol/methylene chloride) yielding 7 mg of the pure product. NMR confirmed the structure.

EXAMPLE 24

Preparation of

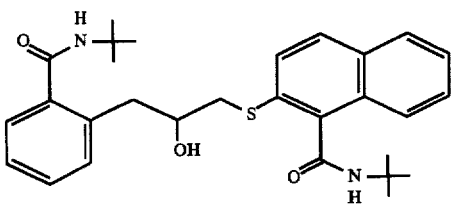

Step 24a

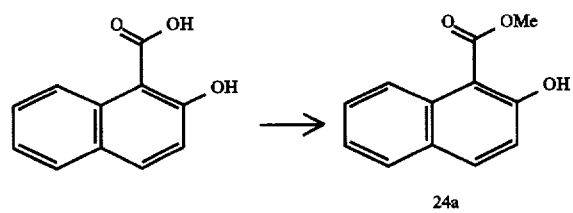

A solution of 10 g (53 mmol) of 2-hydroxy-naphthalene carboxylic acid in 200 ml of ethanol was added, dropwise, to a solution of excess diazomethane in ether at −5° C. Additional starting material (7.18 g) was added to kill the excess diazomethane. Acetic acid was added, the reaction mixture was diluted with ether and extracted with sodium hydroxide solution at a pH of about 8 to 9. The extract was washed with ether and brine, treated with charcoal and dried over MgSO₄. Concentration under vacuum yielded 18 g of crude light yellow solid. Structure of this material was confirmed by NMR. The product was then recrystallized from ether/hexane yielding a total of 14.94 g (82%).

Step 24b

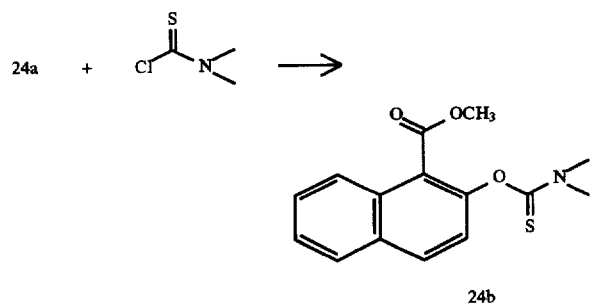

A solution of 2 g (9.915 mmol) of compound 24a in 15 ml of DMF was cooled to 0° C. and 0.40 g of sodium hydride was slowly added. Gas was evolved and the mixture was stirred for 5 minutes then warmed to room temperature. After ten minutes another 5 ml of DMF was added. The solution was then cooled to 0° C. and 1.61 gm of N,N-dimethyl-thio-carbamoyl chloride was added. The mixture was stirred 5 minutes and then warmed back to room temperature. After one hour, the reaction was indicated by TLC to be about 90% complete. The temperature was raised to 50° and the reaction was complete after one more hour. The reaction mixture was poured into ether, extracted with 1N NaOH then with brine. The aqueous layers were then extracted again. The extracts were washed with 1N HCl and dried over MgSO₄. The mass was then concentrated under vacuum to about 200 ml and 1.64 gm of a white solid was filtered off. The filtrate was also collected and concentrated under vacuum to 1.08 g of a yellow oil. The crude product was purified by flash chromatography (40% ethanol/hexane loaded on methylene chloride) yielding 0.23 g of a white solid. The 1.64 gms of white solid was also purified by flash chromatography yielding 1.55 gm. The two products were combined. NNR confirmed the structure.

Step 24c

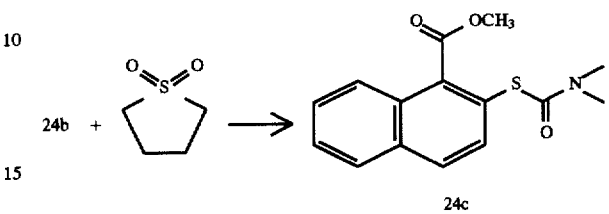

A mixture of 0.9 gm (3.11 mmol) of compound 24b in 25 ml of sulfolane was subjected to 2 freeze-pump-thaw cycles then heated to 180° C. After approximately 2 hours and 45 minutes of heating, TLC indicated that the reaction was complete and it was allowed to cool. The mixture was then poured into water, extracted twice with ether, washed twice with water, dried over MgSO₄ and concentrated under vacuum. The yield was 0.901 g which was purified by flash chromatography in a 1:1 ethyl acetate/hexane. Some impurity remained and the chromatography was repeated yielding a total of 0.46 g (51%). NMR confirmed the structure of the product.

Step 24d

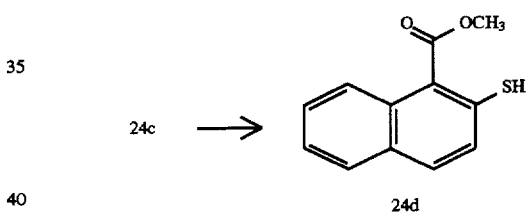

A solution of 0.206 g (0.711 mmol) of compound 24c in 8 ml of methanol was treated at room temperature with 0.35 ml of 10% aqueous sodium hydroxide. When no reaction was observed after 20 minutes, the material was warmed to 40° C. for 30 minutes and stored cold overnight. Another ml of the 10% sodium hydroxide was added and the mixture was stirred at room temperature for one hour, at which time, the temperature was increased to 40° C. for 3 additional hours. The mixture was then washed with 1N HCl and extracted with ethyl acetate. The reaction was repeated and the products from the two runs were combined and purified by flash chromatography (30% ethyl acetate/hexane) yielding 0.262 g (83%). The structure was confirmed by NMR.

Step 24e

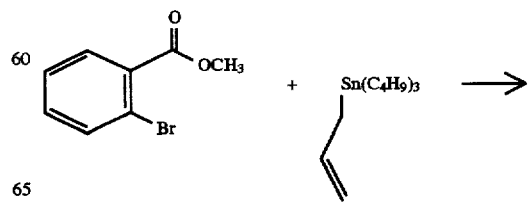

-continued

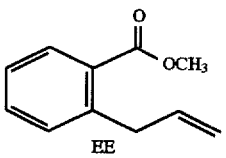
EE

Compound EE was prepared in the following manner. A solution of 6.0 ml (41.71 mmol) of 1-bromo methylbenzoate and 16 ml (51.61 mmol) of tributylpropenyl tin in 15 ml of benzene was heated to 100° C. and allowed to sit at that temperature overnight in a sealed tube. In the morning the solution was filtered twice through a silica gel plug with hexane, then combined with an equal amount of the product of another run of the same reaction. The combined masses totaled 50.5 g. A portion of this product (10 g) was fractionally distilled at 2 mm and 4 fractions were collected. The distilled products were combined and purified by flash chromatography using a 5% ether/hexane to 10% ether/hexane gradient. Yield was 5.1 gm.

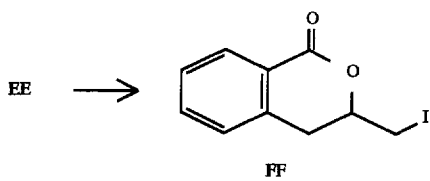
FF

Compound FF was prepared in the following manner. To a mixture of 1.1 gm (6.28 mmol) of compound EE and 20 ml of acetonitrile at room temperature was added 3.0 g (12.13 mmol) of iodine. Reaction was completed in 45 minutes and the reaction mixture was poured into saturated sodium $NaHSO_3$, extracted twice with ethyl acetate, washed again with sodium $NaHSO_3$ and dried over $MgSO_4$. Concentration under vacuum yield 1.7 g of amber oil (94%). Structure was confirmed by NMR.

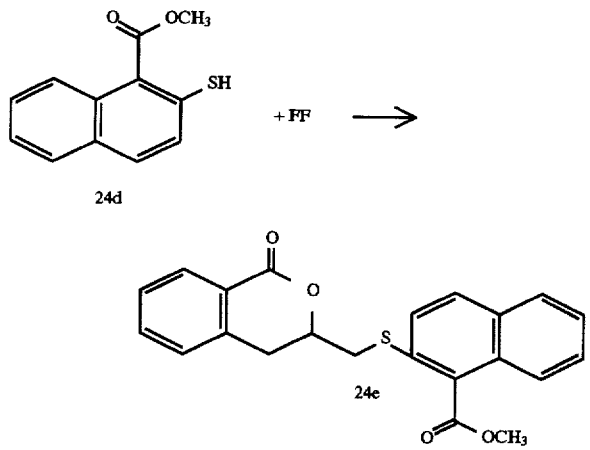

Then, a solution of 0.08 g of potassium hydroxide in a mixture of 0.8 ml of water and 4 ml of ethanol was cooled to 0° C. and a solution of 0.253 g of compound 24d in 1 ml of ethanol was added. The mixture was stirred for 20 minutes and then 0.324 g (1.125 mmol) of compound FF and 1 ml of ethanol was added. The mixture was allowed to warm overnight. The reaction mixture was then poured into water, extracted twice with ethyl acetate, then washed with brine and dried over $MgSO_4$. Concentration under vacuum yielded 0.381 g. The product was purified by flash chromatography (20% ethyl acetate/hexane) yielding 0.289 g (66%) of product. NMR confirmed the structure.

Step 24f

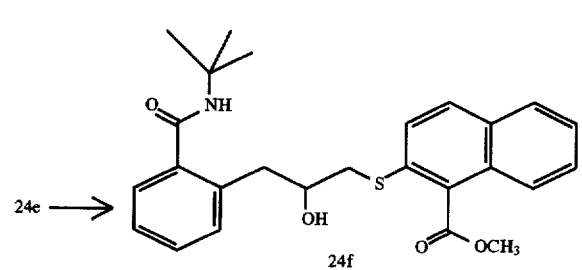

To a solution of 0.66 ml (1.32 mmol) of trimethylaluminum in toluene at 0° C. was added 0.14 ml (1.93 mmol) of t-butylamine. The mixture was warmed and stirred at room temperature for one hour, at which time a solution of 0.09 g (0.238 mmol) of compound 24e in 2 ml of toluene was added. The reaction mixture was heated to reflux for one hour, at which time, TLC showed complete conversion to a more polar product. The mass was cooled, poured into water, extracted twice with ethyl acetate and dried over $MgSO_4$, yielding a crude weight of 0.118 g. This was purified by flash chromatography (40% ethyl acetate/hexane) yielding 0.089 g (76%) of a white solid. NMR confirmed the structure.

Step 24g

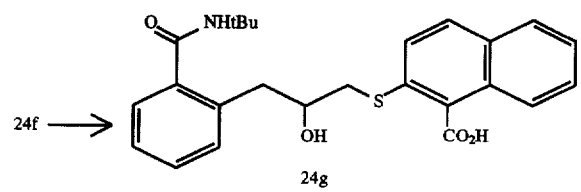

A solution of 2.35 gm (5.2 mmol) of compound 24f in a mixture 60 ml of methanol and 30 ml of 3N NaOH was heated to 60° C. and held at that temperature for about 2.5 hours. The reaction was allowed to cool and was then poured into water and extracted with ethyl acetate. The aqueous layer was acidified and extracted with ethyl acetate. The organic layers were dried over $MgSO_4$ and concentrated. The product was purified by flash chromatography using 50% methanol/methylene chloride, yielding 1.46 gm (64%) of compound 24g.

Step 24h

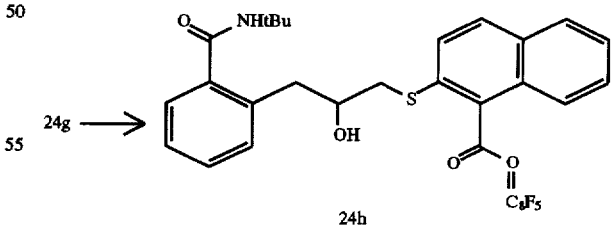

A solution of 0.0937 gm of dicyclohexyl carbodiimide (DCC) in 4 ml of ethyl acetate was cooled to 0° C. and 0.1979 gm of pentafluorophenol in 2 ml of ethyl acetate was added followed by 0.1254 gm of compound 24 g. The reaction progressed until about 80% of compound 24 g was esterified, at which time an additional 0.629 gm of the pentafluorophenol in 1 ml of ethyl acetate was added. After one hour, very little additional reaction had taken place. The mixture was filtered to remove DCC, washed 3 times with saturated Na₂HCO₃, dried over MgSO₄, concentrated under vacuum. Purification by flash chromatography using 40% ethyl acetate/hexane yielded 0.107 gm (59%) of the product as a white solid.

Step 24i

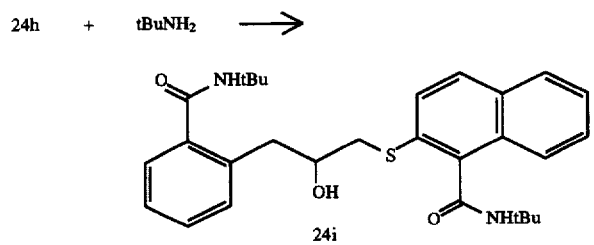

A solution of 0.10 gm (0.168 mmol) of compound 24 h in 3 ml of THF was cooled to 0° C. and 50 µl (0.476 mmol) of t-butylamine was added. After ten minutes stirring, the mixture was waned to room temperature for one hour, then heated to reflux for one hour, cooled to room temperature and stirred overnight. The mixture was reheated to reflux, 2 ml of DMF was added and stirring was continued for 24 hours. The mixture was then diluted in ethyl acetate, washed with H₂O, then with 1N HCl, then with brine, dried over MgSO₄ and concentrated under vacuum. The product was isolated by flash chromatography, yielding 8 mg (10%).

EXAMPLE 25

Preparation of

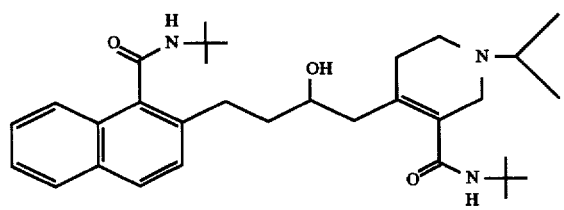

Step 25a

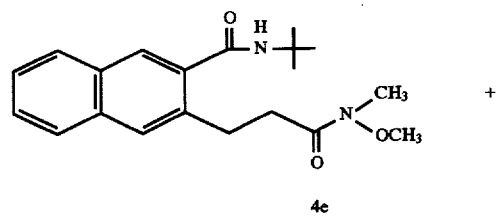

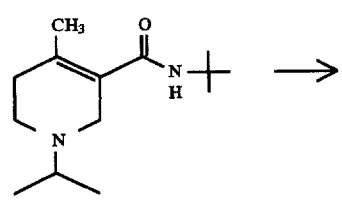

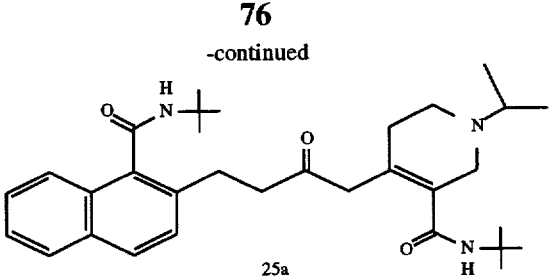

A solution of 6.31 g (1.3 mol) of the amidopyridine derivative in 5 ml of THF containing 0.3 ml of TMEDA was cooled to −78° C. and 2.6 mmol of s-butyl lithium was added. A yellow color resulted. The mixture was stirred for 1.5 hours at −78° C. At this time 0.247 gm (0.649 mmol) of compound 4e in 7 ml of THF was added. A red/brown solution resulted. This solution was stirred at −78° C. for one hour, then quenched with water, extracted with ethyl acetate and concentrated under vacuum. NMR confirmed the structure of the product contaminated with a small amount of residual amidopyridine derivative.

Step 25b

25a ⟶

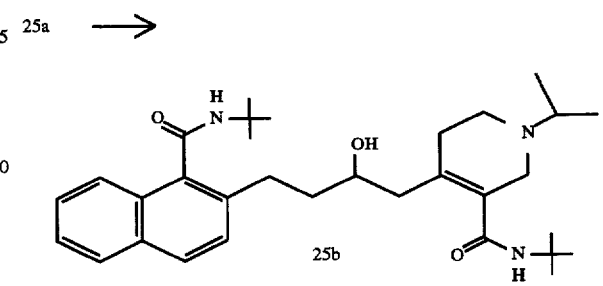

To a solution of 0.39 g (0.69 mmol) of compound 25a in 3 ml of methanol was added 30 mg of NaBH₄. The mixture was stirred at room temperature for two hours and methanol was stripped off under vacuum. The compound was dried over MgSO₄. Purification by flash chromatography (15% ethyl acetate/methylene chloride/1% methanol) followed by precipitation with ether yielded 0.02 gm of the product.

EXAMPLE 26

Preparation of

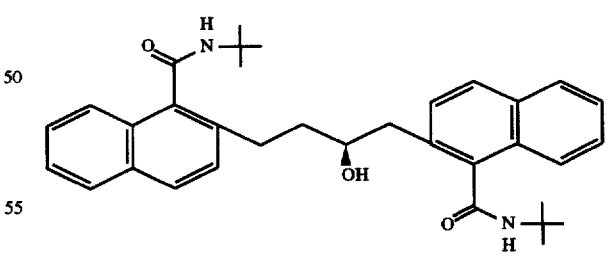

Step 26a

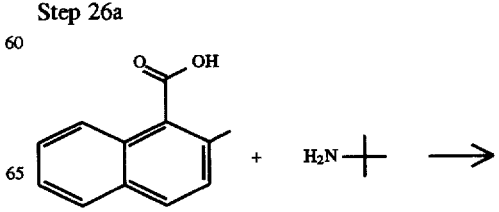

-continued

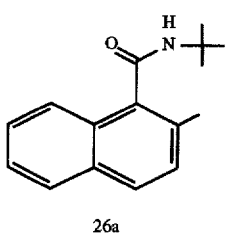

26a

About 2.2 gm (11.82 mmol) of 2-methyl-1-naphthoic acid was partially dissolved in 30 ml of benzene and the solution was cooled to 0° C. To the cold solution was added 1.34 ml (15.37 mmol) of oxalyl chloride and one drop of DMF. Vigorous bubbling resulted when the solution was warmed to room temperature. Then the temperature was raised to near reflux for a total of 1 hour. TLC indicated fair amount of residual starting material remaining so another equivalent of oxalyl chloride and DMF was added. The temperature was raised back to reflux and allowed to reflux for 20 minutes. The reaction mixture was then concentrated under vacuum to an orange solid. The material was partially redissolved in 30 ml of methylene chloride and 2.73 ml of t-butyl amine was added. Reaction then proceeded cleanly but was allowed to continue overnight. The mass was washed with water and ethyl acetate and purified by flash chromatography using a 4:1 hexane/ether mixture. Yield was 2.6 gm (92%). Structure was confirmed by NMR.

Step 26b

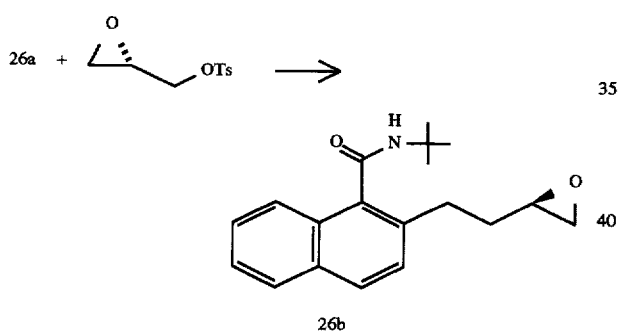

26b

A solution of 1.2 g of compound 26a and 15 ml of THF was cooled to −78° C. and 11.7 ml of s-butyl lithium was added. The solution was stirred for 1.5 hours, at which time 1.14 g (4.97 mmol) of S-glycidyl tosylate was added. The reaction mix was stirred for one half hour at −78° C., then quenched with NH₄Cl, extracted with ethyl acetate and washed with water followed by brine and dried over MgSO₄. The extract was then concentrated on 7 ml of Florisil and purified by flash chromatography (20% THF/hexane). The yield was 0.75 g of product (51%). Structure was confirmed by NMR.

Step 26c

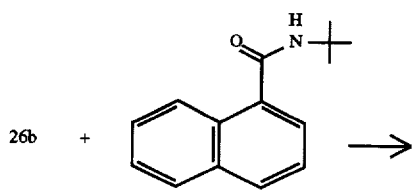

-continued

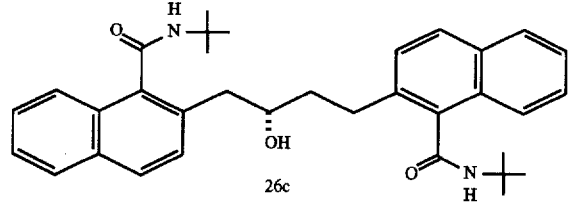

26c

To 0.459 g (2.02 mmol) of N-(t-butyl)naphthamide at −12° C. was added 4 ml of s-butyl lithium, and the mix was warmed to 0° C. and stirred for 45 minutes. A solution of 0.3 g (1.01 mmol) of compound 26b in 10 ml of THF was added. The red solution turned to a milky yellow/brown. In about 18 minutes following addition of compound 26b, 80% of the compound had been consumed. The reaction was then quenched with saturated NH₄Cl and extracted with ethyl acetate. The material was purified by flash chromatography in a 1:1 hexane/ethyl acetate. The mass was then concentrated on 7 ml of Florisil, and subjected again to flash chromatography using THF/hexane. A total of about 0.16 g of product was recovered. NMR confirmed the structure.

EXAMPLE 27

Preparation of

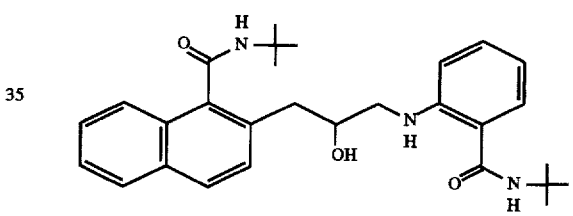

Step 27a

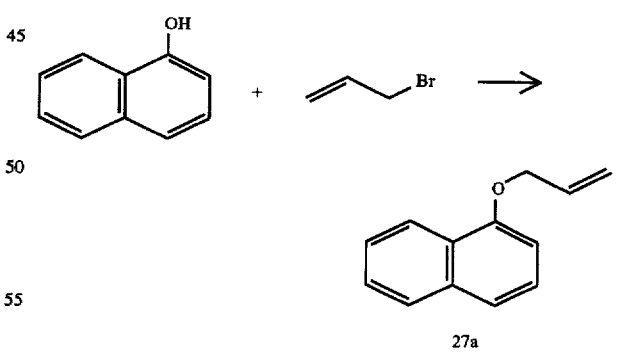

27a

To a solution of 1 naphthol in 100 ml of acetone was added 13.7 g of K₂CO₃, then 6.6 ml (76.29 mmol) of allyl bromide. The solution was heated to reflux for four hours, at which time TLC indicated the reaction to be about 80% complete. Another 3.3 ml of allyl bromide was added and the solution was refluxed mildly overnight. The reaction mass was then filtered and concentrated under vacuum, yielding 13.7 g (98%) of product. Structure was confirmed by NMR.

Step 27b

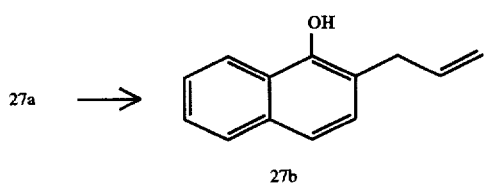

A solution of 16.32 g of compound 27a in 125 ml of N,N-dimethyl aniline was heated to reflux under an argon atmosphere. Reflux was continued for four hours, at which time TLC showed the reaction to be complete. The reaction mixture was allowed to sit overnight at room temperature, then poured into 100 ml of 3N HCl and then 200 ml of ether were added. The organic layer was separated, washed six times with 100 ml portions of 3N HCl and then four times with 200 ml of 1N HCl. The extract was then washed with four 200 ml portions of water and dried on $MgSO_4$. The dried product was distilled through a short path column at 130° C. under an atmosphere of argon. Yield was 15.58 gm of an orange oil which solidified upon standing.

Step 27c

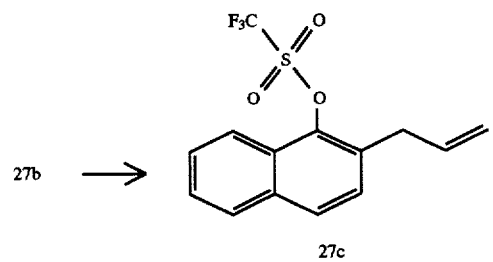

A solution of 4.1 gm (22.26 mmol) of compound 27b in 50 ml of methylene chloride was cooled to 0° C. and 1.89 ml of pyridine was added, followed by dropwise addition of 6.6 g (23.37 mmol) of triflic anhydride. The reaction mixture was stirred for 6 hours, while allowing the temperature to rise from 0° C. to room temperature. The mass was poured in 100 ml of 1N HCl and extracted with methylene chloride. The extracts were washed with saturated $NaHCO_3$, then concentrated on 20 ml of Florisil. Flash chromatography using a 20:1 hexane/ethyl acetate yielded 5.60 gm of product.

Step 27d

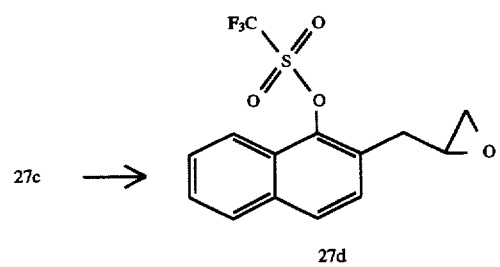

A solution of 5.6 gm (17.7 mmol) of compound 27c in 60 ml of methylene chloride was cooled to 0° C. and 6.11 g of m-chloro-perbenzoic acid (MCPBA) was added. The mixture was stirred for 30 minutes at 0° C., then at room temperature for 5 hours at which time another 1.3 g of MCPBA was added and the solution, warmed to 35° C. and allowed to stir overnight. The mixture was then poured into 0.5N NaOH, extracted with two 50 ml portions of methylene chloride, washed, dried and filtered through silica gel, then concentrated under vacuum. Flash chromatography in an 8:1 hexane ethyl acetate mixture yielded 5.4 g of product. The structure was confirmed by NMR.

Step 27e

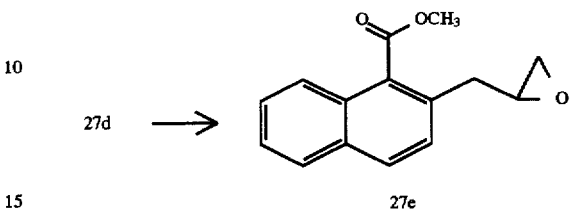

A mixture consisting of 1.41 gm (4.42 mmol) of compound 27d, 0.068 gm of palladium (II) acetate, 0.125 gm of 1,3-bis diphenylphosphino propane (DPPP), 1.4 ml of triethyl amine, 15 ml of DMSO and 10 ml of methanol was prepared and heated to 75° C. under a carbon monoxide atmosphere. Heating was continued for three hours at which time an additional 17 mg of the palladium acetate and 35 mg of DPPP was added. The mass was heated at 70° C. overnight, at which time TLC indicated that the reaction was finished. The mass was poured into 50 ml of water, then into 50 ml of saturated $NH_4Cl$ and extracted with ethyl acetate followed by washing with $NaHCO_3$ and brine. Flash chromatography in 4:1 hexane/ethyl acetate yielded 0.25 g (24.3%) of product. Structure was confirmed by NMR.

Step 27f

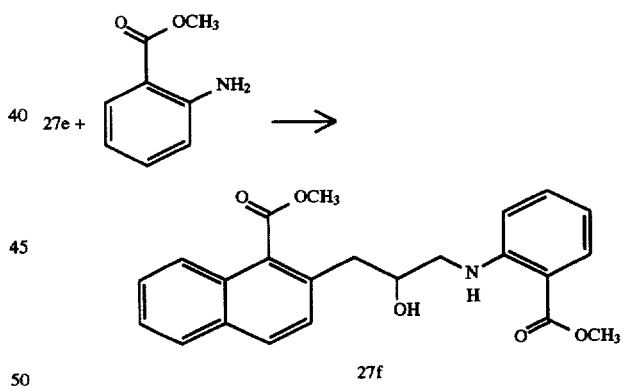

To a solution of 0.255 g (1.053 mmol) of compound 27e, 0.353 g of magnesium perchlorate in 3.5 ml of acetonitrile, was added 0.204 ml (1.58 mmol) of 2-amino methyl benzoate. The mixture was stirred overnight at room temperature, then poured into water, extracted with ethyl acetate, then concentrated in 3 ml of Florisil. Flash chromatography in 1:1 hexane/ether solution yielded 0.25 g of a white sticky foam.

Step 27g

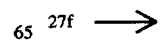

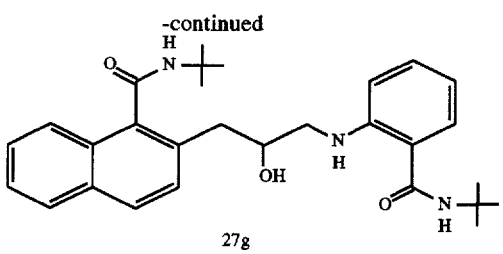

A solution of 2.34 ml of trimethyl aluminum in 4 ml of toluene was cooled to 0° C. and 0.504 ml (4 mmol) of t-butyl amine was added and the mixture was stirred for one hour at room temperature. After an hour, 0.23 g (0.0585 mmol) of compound 27f in 3 ml of toluene was added, dropwise, and the solution was heated to 95° C. for about 2.5 hours. Temperature was reduced to 65° C. and stirring was continued for 4 more hours at which point the heat was turned back up to 120° C. and continued at that temperature for a total of 22 hours. The reaction mixture was poured into 1N HCl and then extracted with ethyl acetate, washed with water and concentrated on 3 ml of Florisil. Flash chromatograph yielded 0.075 gm (80%) of product. Structure was confirmed by NMR.

EXAMPLE 28

Preparation of compound 27 by alternate route.

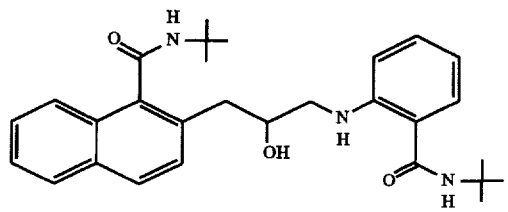

Step 28a

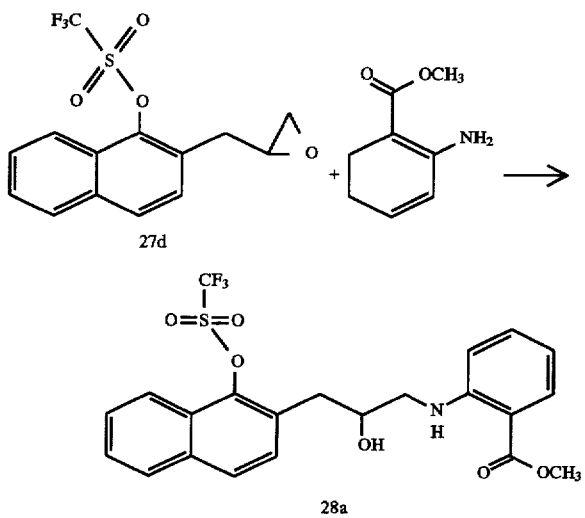

A solution of 0.068 g (0.205 mmol) of compound 27d and 0.046 g of magnesium perchlorate in 1 ml of acetonitrile was prepared. At room temperature, 26 microliters (0.205 mmol) of 2-amino-methyl benzoate was added. The mixture was stirred at room temperature for one hour at which time another 13 µl of the 2-amino-methyl benzoate was added and another 0.024 g of magnesium perchlorate. The reaction mixture was stirred overnight at room temperature, after which the solution was warmed to 45° C. and stirred for 4 more hours. The reaction mix was poured into water, extracted with ethyl acetate, then washed with brine. After concentration on 2 ml of Florisil, the mixture was purified by flash chromatography (hexane/ethyl acetate), yielding 0.068 g (68.7%) of product. NMR confirmed the structure.

Step 28b

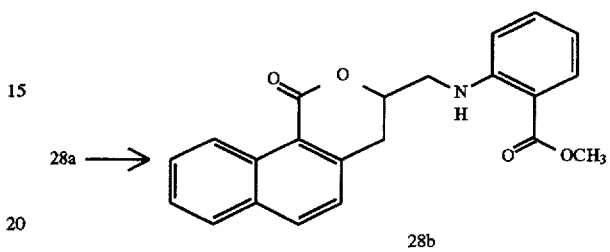

Under a carbon monoxide atmosphere, a mixture consisting of 0.068 g of compound 28a, 3 mg of palladium (II) acetate, 4 mg of DPPP, 70 µl of triethyl amine, 1 ml of DMSO, 0.6 ml of methanol and 250 µl of 1,2-dichloroethane was heated under a carbon monoxide atmosphere to about 65° C. for three hours and then for one more hour at 70° C. The reaction mixture was poured into dilute HCl and extracted with ethyl acetate, washed with NaHCO₃ and brine and dried over MgSO₄, then filtered through Celite and concentrated on 3 ml of Florisil. Flash chromatography in a 3:2 hexane/ether yielded about 0.06 g of a white solid product. NMR confirmed the structure.

Step 28c

28b ⟶

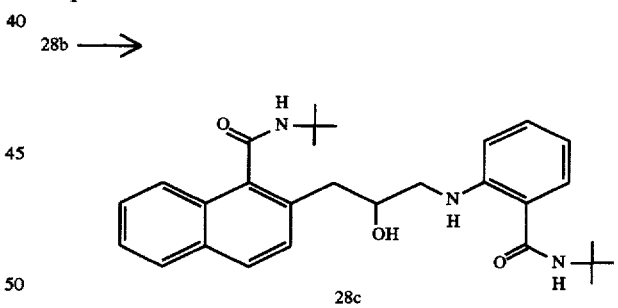

To 0.44 ml of a 2.0M solution of trimethyl aluminum in toluene at 0° C. was added 95 microliters (0.904 mol) of t-butyl amine. The mixture was stirred for one hour at room temperature, at which time a solution of 0.04 g of compound 28b in 2 ml of toluene was slowly added. The mixture was heated at 95° C. for 45 minutes, at which time TLC indicated that the reaction was essentially complete. The solution was then refluxed mildly for three hours. Following reflux, the solution was poured into dilute HCl, extracted with ethyl acetate, and washed with water and brine. Following concentration on 2 ml of Florisil, the product was purified by flash chromatography in a 3:2 ethyl hexane solution. Structure was confirmed by NMR.

EXAMPLE 29

Preparation of

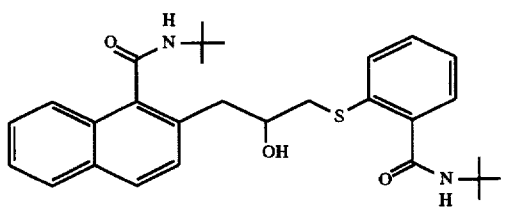

Step 29a

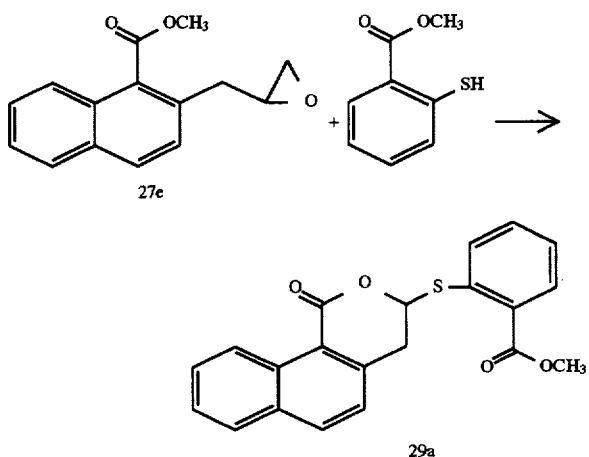

To a solution of 107 μl (0.776 mmol) of 1-mercapto methylbenzoate in 2 ml of THF was added 23 mg of sodium hydride. Bubbling occurred and the reaction mixture turned yellow and was stirred at room temperature for 45 minutes. A solution of 0.188 g (0.776 mmol) of compound 27e in 1 ml of THF was added to the mass at room temperature. After one hour at 35° C., the mixture was warmed to 55° C. In about 20 minutes, reaction was complete. The reaction mass was worked up with 1N HCl and water and was combined with another portion of the same material derived in an earlier experiment using the same procedure. Flash chromatography in 3:1 hexane/ethyl acetate eluent yielded 0.19 gm of product. Structure was confirmed by NMR.

Step 29b

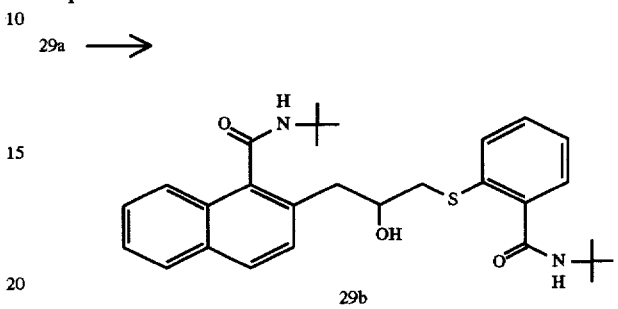

To 3 ml of a 2.0M solution of trimethyl aluminum in toluene at 0° C., was added 0.293 μl (2.78 mmol) of t-butyl amine. The mix was left stirring for one hour at room temperature, at which time 0.17 g (0.449 mmol) of compound 29a in 2 ml of toluene was added, dropwise. The mixture was heated to mild reflux (75°–80° C.) for about 15 minutes at which time reflux was increased to 100° C. The mixture was then poured into 50 ml of water, extracted with ethyl acetate, dried under vacuum on 3 ml of Florisil, then purified by flash chromatography using a 1:1 hexane ethyl acetate. Structure of the product was confirmed by NMR.

EXAMPLES 30–46

Using essentially the same chemistry and the same reaction sequences described in Examples 1 thru 29, the following compounds have also been synthesized:

| EXAMPLE # | STRUCTURE |
|---|---|
| 30 | ![structure] |
| 31 | ![structure] |

-continued
| EXAMPLE # | STRUCTURE |
|---|---|
| 32 | 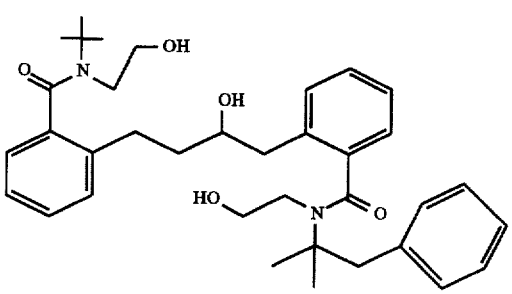 |
| 33 | 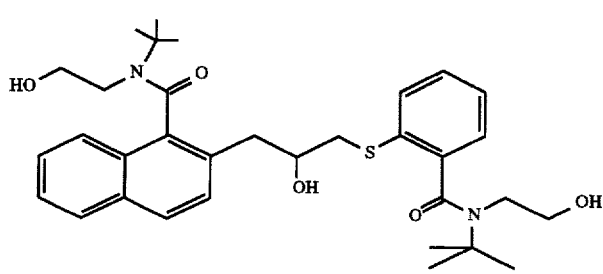 |
| 34 | 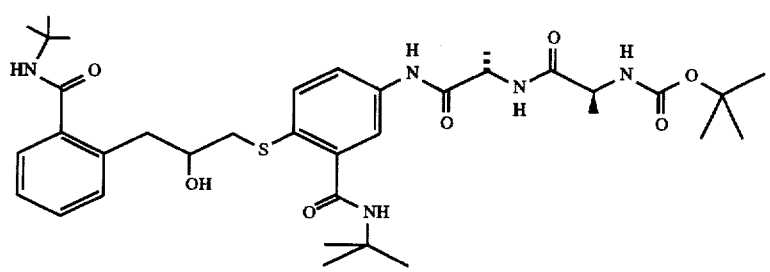 |
| 35 | 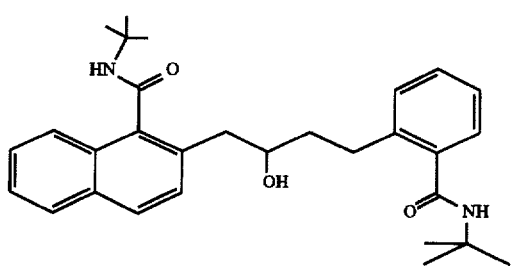 |
| 36 | 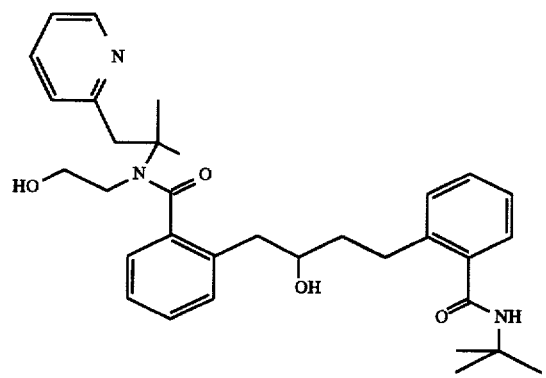 |

-continued
| EXAMPLE # | STRUCTURE |
|---|---|
| 37 | 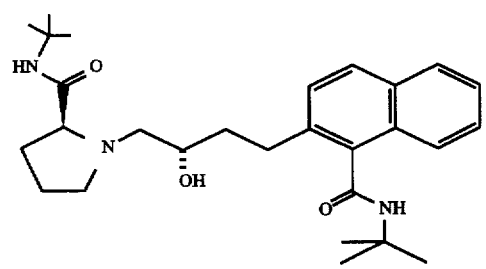 |
| 38 | 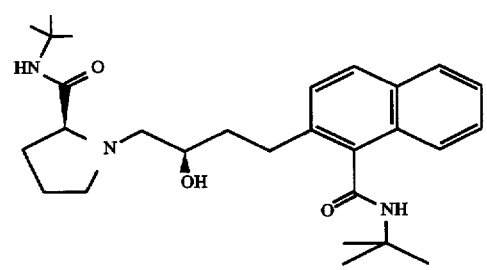 |
| 39 | 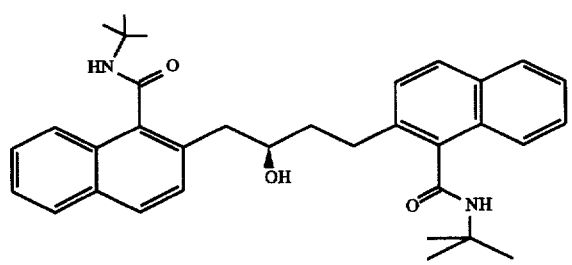 |
| 40 | 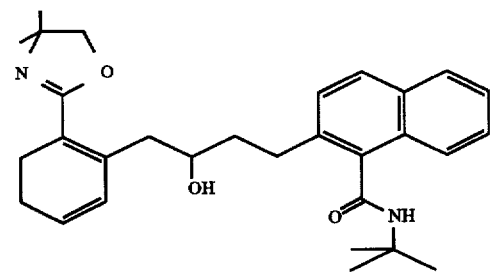 |
| 41 | 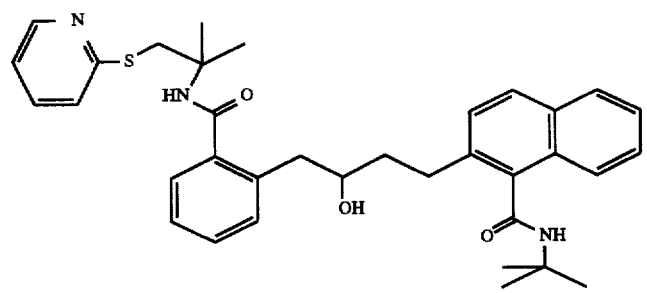 |

-continued
| EXAMPLE # | STRUCTURE |
| --- | --- |
| 42 | 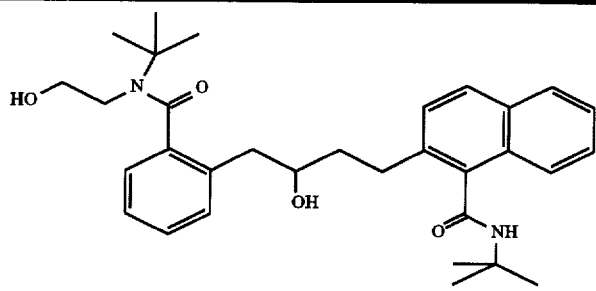 |
| 43 | 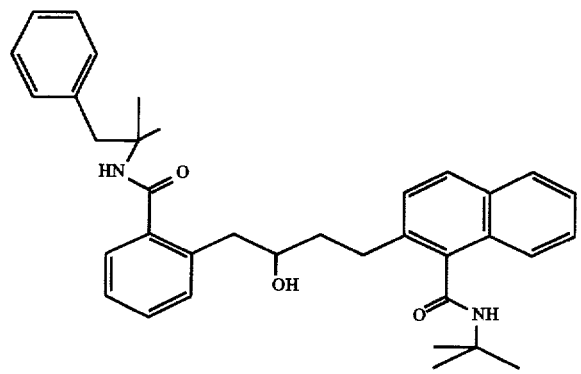 |
| 44 | 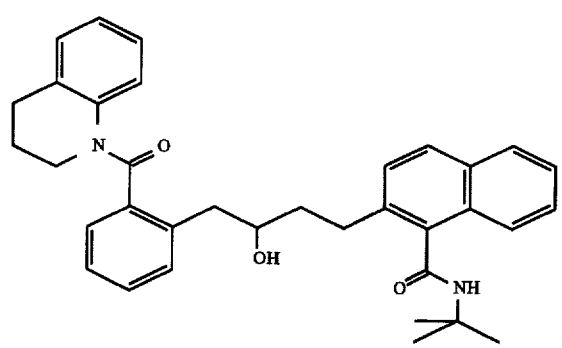 |
| 45 | 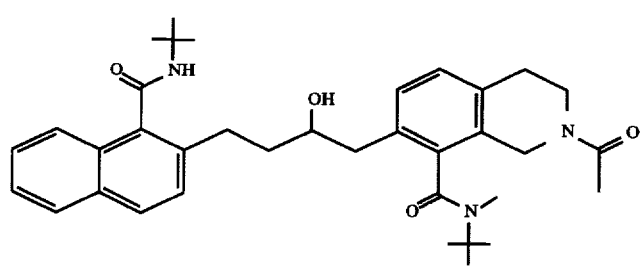 |
| 46 | 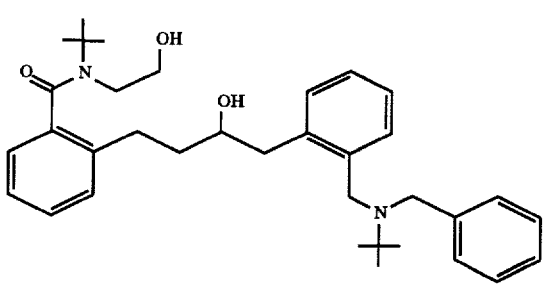 |
The terms "essentially enantiomerically pure" or "essentially disastereomerically pure" mean that such compound so described is essentially free of its enantiomer or of other diastereomers and thus has a significantly lower Ki than a compound that is not essentially free either of its enantiomer or of other disastereomers.

The HIV-protease inhibitory compounds were screened by a variety of assays to determine their biological utility. Among the tests performed were the proteolytic inhibition rates and antiviral effect on HIV-infected cell lines. The procedures for each experiment are described in detail below. the IC50 and Ki data were generated by Agouron scientists, whereas the protease activity with the cell cultures was measured by independent, outside laboratories. The results from these assays for Examples 1–46 are summarized in Table I, which is set forth following the descriptions below of the experimental procedures.

IC50 and Ki Determination of HIV Protease Inhibitors

1. Proteolytic activity of purified HIV-1 protease was routinely measured using the chromogenic assay developed by Richards et al. (J. Biol. Chem. 265:7733 (1990)). Synthetic peptide His-Lys-Ala-Arg-Val-Leu-Phe (pNO2)-Glu-Ala-Nle-Ser-NH2 (American Peptide Company) was used as the substrate.

2. The assay was carried out in 0.5M NaCl, 50 mM MES pH 5.6, 2% DMSO (dimethylsulfoxide) at 37° C. Cleavage of the scissile bond between leucine and paranitrophenylalanine (Phe(pNO2)) was assayed by spectrophotometric monitoring of the decrease in absorbance at 305 nm. Initial velocity was determined as the rate of decline of absorbance during the first 100 seconds of reaction. Under standard conditions, the Michaelis constant (Km) for this substrate is 52±16 µM.

3. For determination of inhibition rates of HIV-1 protease inhibitors, saturated concentration of substrate (200 µM) was used. Between 15–25 concentrations of inhibitor were added and velocity of reaction was measured at each of the concentrations, as described above.

4. Inhibition constants were calculated using the method of Jackson et al. (Adv. in Enzyme Regulation 22:187 (1984)). In the above described assay, Pepstatin A-a standard inhibitor of aspartic proteases has a Ki app=3.1±0.1 µM and $IC_{50}$=3.8±0.7 µM.

Primary Drug Screening of Anti-HIV Compounds at Southern Research Institute (SRI)

1. Principle of MTT Assay

SRI has an established program for the primary antiviral analysis of compounds in microtiter assays which measure the ability of a selected compound to inhibit HIV-induced cell killing. This assay involves the conversion of the tetrazolium dye MTT to a colored formazan product by mitochondrial enzymes in metabolically active cells. This assay system is presently used at SRI to screen over 30,000 compounds per year. Briefly, the assay involves the infection of CEM or MT2 cells in round bottom 96-well plates. The compound of interest is added just prior to infection. Following 6 days of incubation at 37° C. the plates are stained with MTT. The results of the assay are quantitated spectrophotometrically on a Molecular Devices Vmax plate reader. The data is analyzed by linear regression utilizing an inhouse software program to calculate antiviral activity. ($IC_{25}$, $IC_{50}$, $IC_{95}$) and toxicity ($TC_{25}$, $TC_{50}$, $TC_{95}$) as well as other values.

Primary antiviral assays are routinely performed in CEM or MT-2 cells. SRI has found that all active compounds have been identified in CEM cells while experiments performed in the MT-2 cell line miss a small proportion of the active compounds. 2. Standard Screening Assays in CEM and MT-2 Cells a. Compound dilution and delivery to the plates Drugs will be solubilized in the appropriate vehicle such as distilled water or DMSO if necessary. Latex gloves, lab coats and masks are used during all phases of the handling process to prevent exposure to potentially harmful agents. The drug is prepared at the appropriate concentration and stored at −20° C. until used by the screening laboratory. The first dilution of each compound is made in a dilution tube with medium to yield a concentration two-fold that of the highest test concentration. Sterile titer tubes are then used to make serial one half-log dilutions of each compound. Following drug dilution, the diluted compound is added to the appropriate well of a 96-well microtiter plate. Up to 12 dilutions can be assayed conveniently in triplicate on a single plate with all appropriate controls including cell control, virus control, toxicity control, drug color control, medium control and plastic (background) control. When testing includes only six dilutions, two drugs can be assayed on a single microtiter plate. The drugs are added to the plate in a final volume of 100 microliters.

b. Cells and virus

During the time the drug dilutions are prepared, cells are washed and counted. Viability is monitored by trypan blue dye exclusion and assays are not performed if the viability falls below 90%. Cells are maintained in an exponential growth phase and are split 1:2 on the day prior to assay to assure exponential growth rate.

For the primary screen, the cell lines utilized are CEM and MT-2. Unless otherwise indicated, the medium used is RPMI 1640 with 10% heat-inactivated fetal calf serum (FBS), glutamine and antibiotics.

Cells are propagated at 37° C. in an atmosphere of 5% $CO_2$ in air. The virus employed for this work is HIV-1 isolates IIIB and/or RF, which are prepared by an acute infection process.

Briefly, virus-infected cells are pelleted on a daily basis beginning at three days post-infection until the virus has killed all of the cells in the culture. Reverse transcriptase activity and p24 ELISA are used to identify pools with the greatest amount of virus.

These 24-hour harvests are pooled, filtered and frozen at −90° C. Prior to use in the assay, the infectious pool of virus is titered on all available cell lines in order to determine the amount of virus required in the antiviral assay.

In general, pools produced by the acute infection method require the addition of one microliter of infectious virus per well resulting in the screening of drugs at a multiplicity of infection of 0.01. In this manner enough virus is prepared and frozen to complete over one thousand microtiter plates, allowing the testing of up to two thousand compounds from a single stock of infectious virus. The use of a single stock of virus for a long period of testing has very favorable effects on the repeatability of the assay systems.

Virus infection of the CEM and MT-2 cells for the antiviral assay is carried out in a bulk infection process. The appropriate number of cells required to complete the assay is mixed with infectious virus in a conical centrifuge tube in a small total volume of 1–2 milliliters.

Following a 4-hour incubation the infected cells are brought to the appropriate final concentration of $5\times10^4$ cells per milliliter with fresh tissue culture medium and 100 microliters are added to the appropriate experimental and virus control wells. Uninfected cells at the same concentration are plated for the toxicity controls and for the cell controls. Assays can also be performed using an inwell infection method. In this case, drug, cells and virus are added to the well individually. In each case the MOI is adjusted to give complete cell killing in the virus control wells by Day 6.

93 c. Evaluation of CPE-inhibition

Following the addition of cells and drugs to the microtiter plate the plate is incubated for 6 days at 37° C. Experience has determined that incubation for longer periods of time (7–8 days) or the use of higher input cell numbers ($1 \times 10^4$) results in significant decreases in cell control viability and a narrowing in the differential in optical density between cell and virus controls upon staining with MTT.

The method of evaluating the antiviral assay involves the addition of 20 microliters of the tetrazolium salt MTT at 5 mg/ml to each well of the plate for 4–8 hours. After this incubation period the cells are disrupted by the addition of 50 μl of 20% SDS in 0.01N HCl.

The metabolic activity of the viable cells in the culture result in a colored reaction product which is measured spectropotometrically in a Molecular Devices Vmax plate reader at 570 nm. The optical density (O.D.) value is a function of the amount of formazan product which is proportional to the number of viable cells.

The plate reader is on-line to the screening laboratory microcomputer which evaluates the plate data and calculates plate data. The plate report provides a rundown of all pertinent information including the raw O.D. values, the calculated mean O.D.'s and the percent reduction in viral CPE as well as calculations including $TC_{50}$, $IC_{50}$ and antiviral and specificity indices. Finally, the results include a plot which visually depicts the effect of the compound on uninfected cells (toxicity) and the protective or nonprotective effect of the compound on the infected cells.

Table I

Notes about the table:

(1) If $IC_{50}$ or Ki values are not indicated, the test was not performed for the particular compound.

(2) The anti-viral data are given for 2 cell lines, representing testing done at Southern Research Institute. The first position of each line represents data obtained for the CEM cell line and the second position indicates the viral inhibition of MT-2 cells. If no data are listed, then the compound has not been tested for its anti-viral effects.

| Ex | IC50(μM) | Ki(μM) | Viral CEM/MT-2 (μq/ml) |
|---|---|---|---|
| 1 | 30 | — | —/— |
| 2 | 1.02 | 1.01 | —/— |
| 3 | ~20 | — | —/— |
| 4 | 40% at 20 | — | —/— |
| 5 | 15 | — | —/— |
| 6 | 18 | — | —/— |
| 7 | 0.82 | 0.79 | 29.5/— |
| 8 | 40% at 10 | — | —/— |
| 9 | 5.6 | 5.4 | —/— |
| 10 | 1.42 | 0.99 | 6.01/— |
| 11 | 20% at 50 | — | —/— |
| 12 | 10% at 200 | — | —/— |
| 13 | 18 | — | —/— |
| 14 | >200 | — | —/— |
| 15 | 40% at 200 | — | —/— |
| 16 | 40% at 200 | — | —/— |
| 17 | 7 | — | —/— |
| 18 | 40% at 100 | — | —/— |
| 19 | 1.19 | 0.84 | —/— |
| 20 | 20% | — | —/— |

94

-continued

| Ex | IC50(μM) | Ki(μM) | Viral CEM/MT-2 (μq/ml) |
|---|---|---|---|
| 21 | at 200 20% at 200 | — | —/— |
| 22 | 60 | — | —/— |
| 23 | 200 | — | —/— |
| 24 | 50 | — | —/— |
| 25 | 70 | — | —/— |
| 26 | 0.88 | 0.48 | —/— |
| 27 | 120 | — | —/— |
| 28 | 120 | — | —/— |
| 29 | 25 | — | —/— |
| 30 | 20% at 100 | — | —/— |
| 31 | 4.1 | 2.7 | —/— |
| 32 | 1.33 | 1.27 | —/— |
| 33 | 16 | — | —/— |
| 34 | >200 | — | —/— |
| 35 | 3 | — | —/— |
| 36 | 9 | — | 30/— |
| 37 | 10% @ 10 | — | —/— |
| 38 | 10% @ 10 | — | —/— |
| 39 | 20 | — | —/— |
| 40 | 60 | — | —/— |
| 41 | 55 | — | —/— |
| 42 | 15 | — | —/— |
| 43 | >20 | — | —/— |
| 44 | 27 | 7.9 | —/— |
| 45 | 40% @ 200 | — | —/— |
| 46 | 8.3 | 7.9 | —/— |

As the preferred synthesis of reaction sequence A described herein, there is a proviso that if $R'_1$, $R'_2$, $R'_3$ and $R'_4$ are individually selected from alkyl, cycloalkyl, aryl, and substituted alkyl, cycloalkyl or aryl, or $R'_1$ and $R'_2$ or $R'_3$ and $R'_4$ form a ring with the nitrogen atom to which they are attached, then at least one of $R'_1$, $R'_2$, $R'_3$ and $R'_4$ must be hydrogen.

We claim:

1. A compound selected from

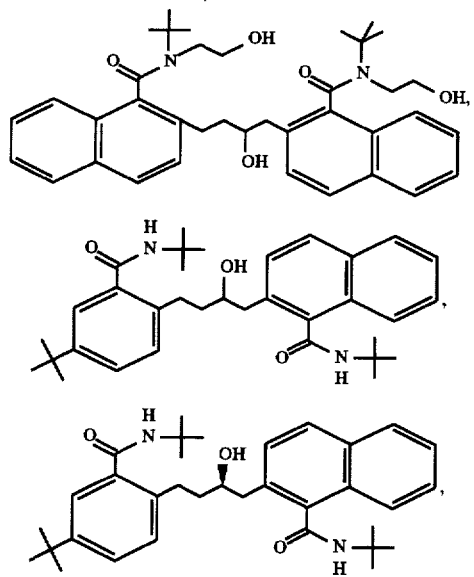

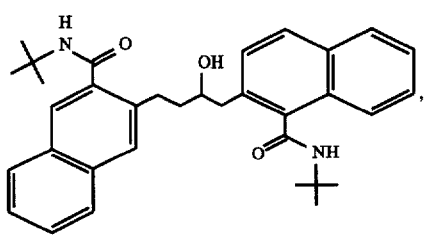
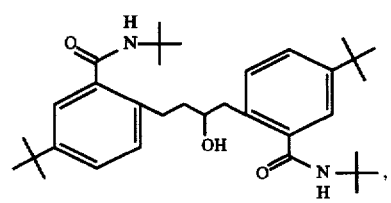
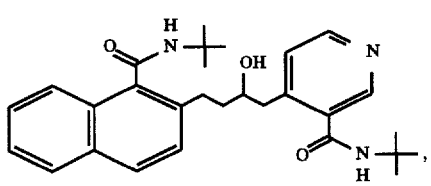
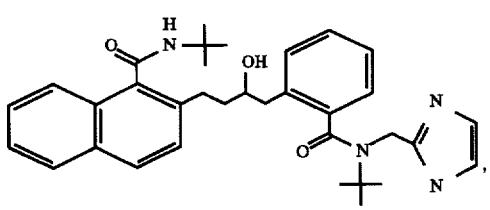
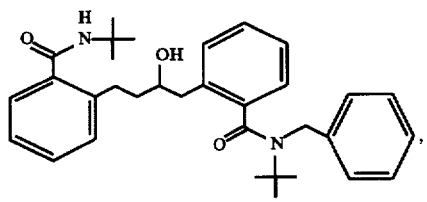
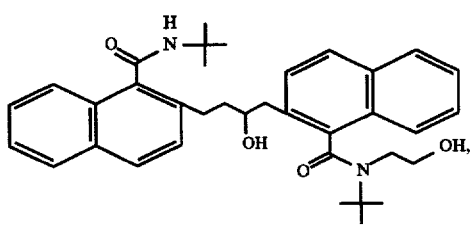
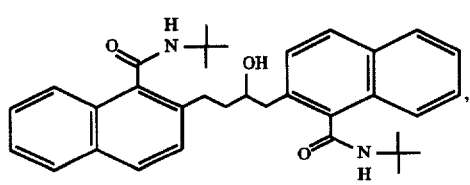
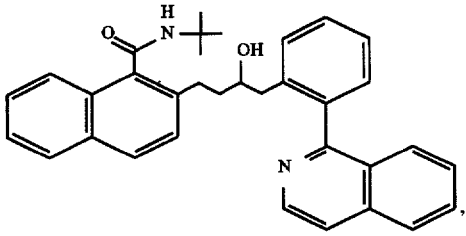
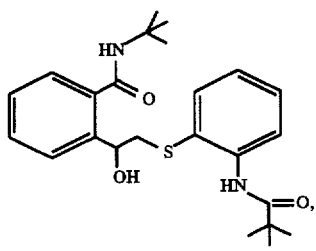
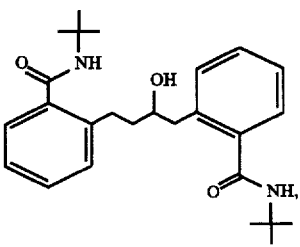
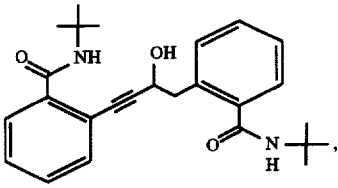
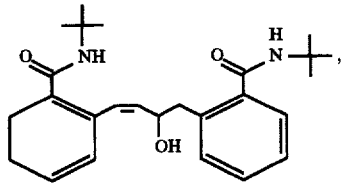
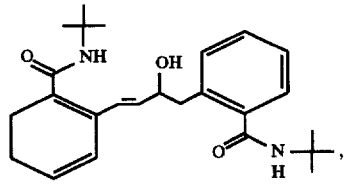
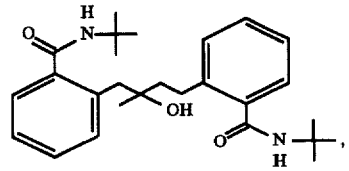

97
-continued
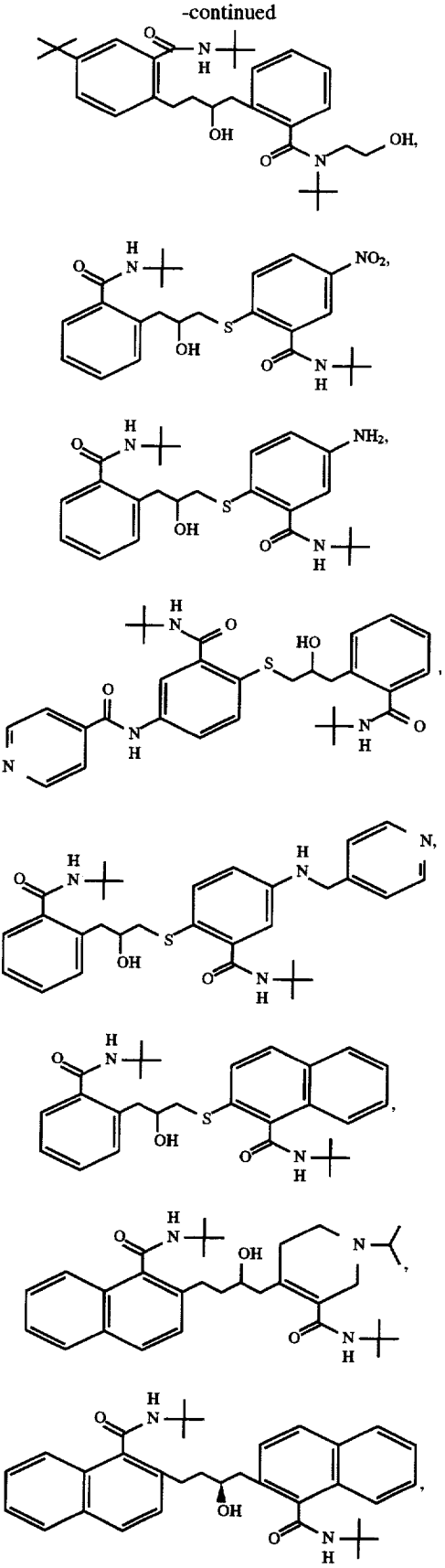
98
-continued
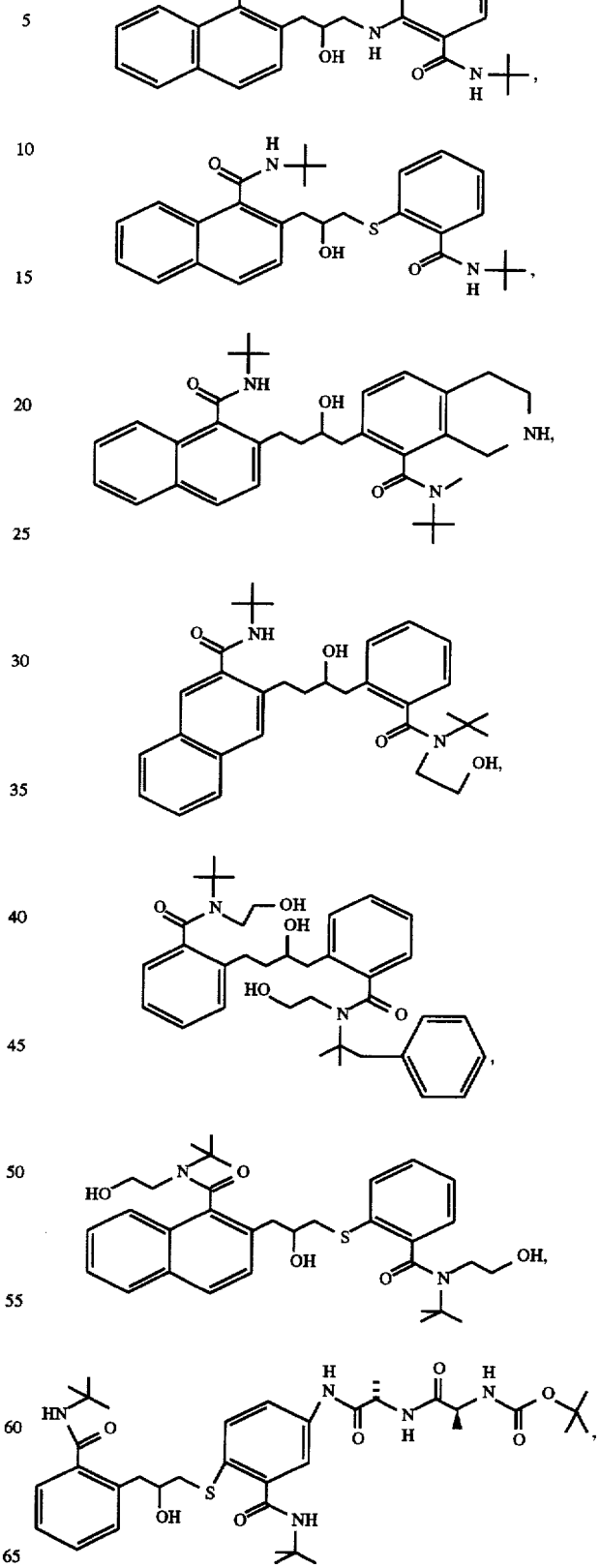

-continued
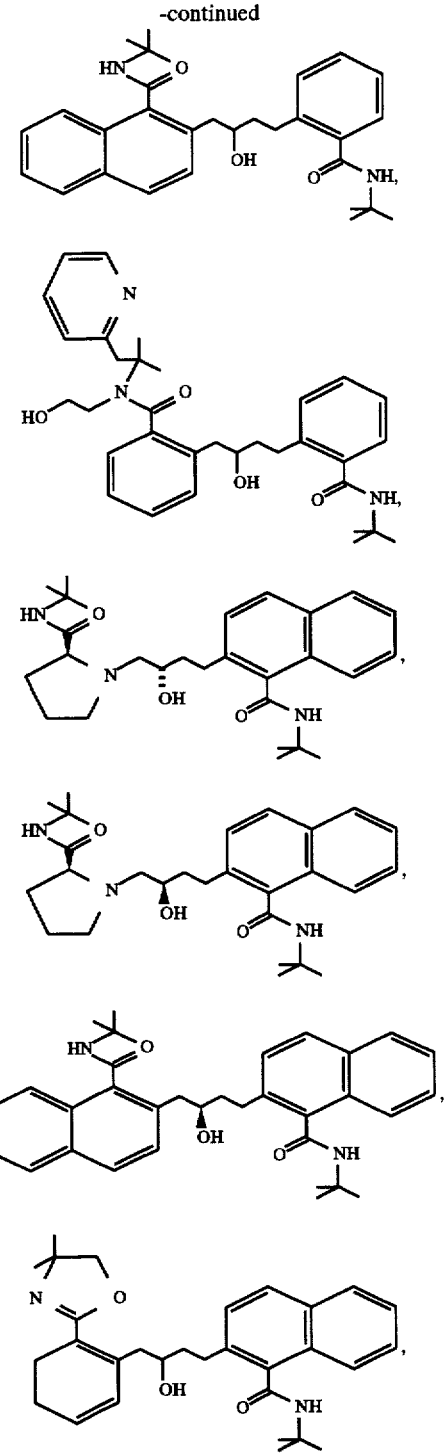
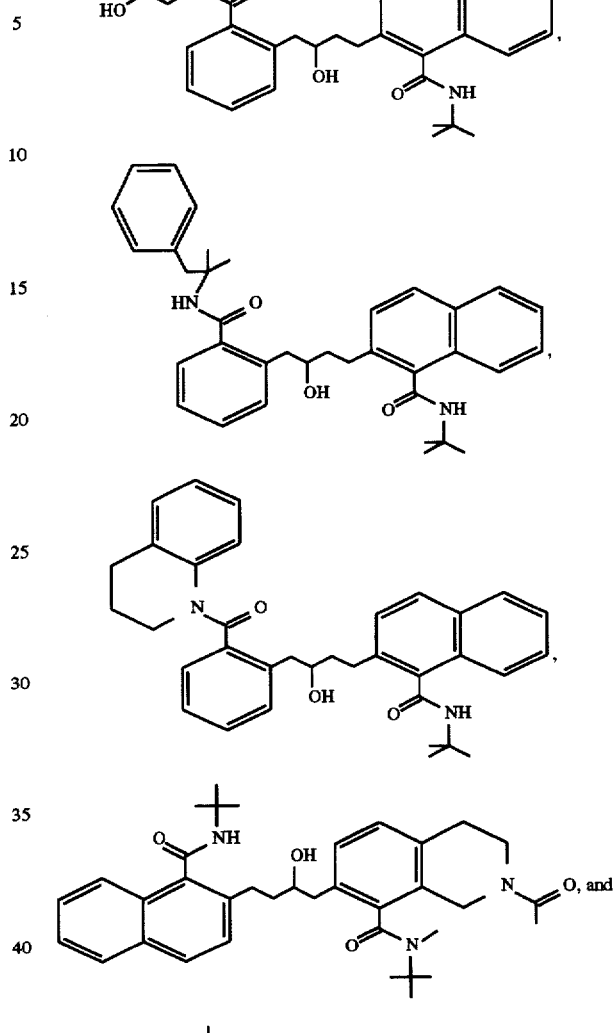
or a pharmaceutically acceptable salt thereof.
2. A composition useful for inhibiting HIV protease which comprise
(1) a compound selected from
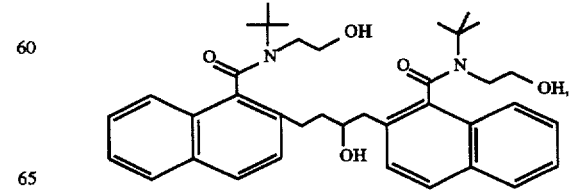

101
-continued
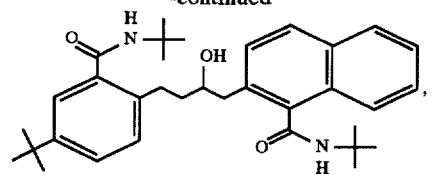
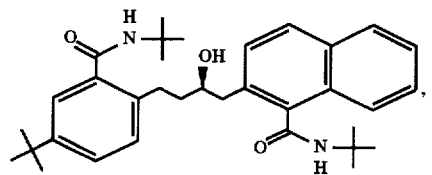
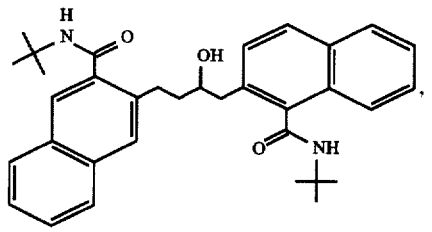
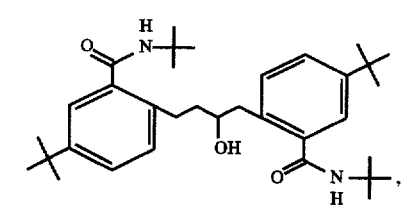
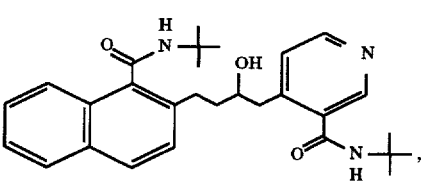
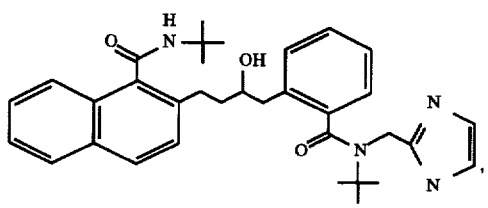
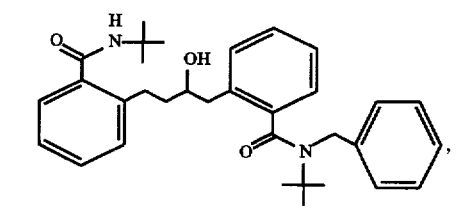
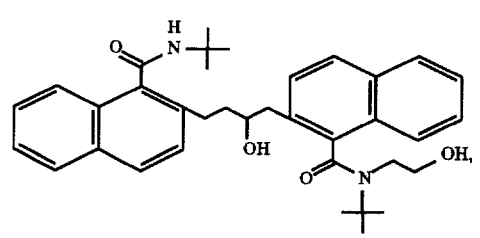
102
-continued
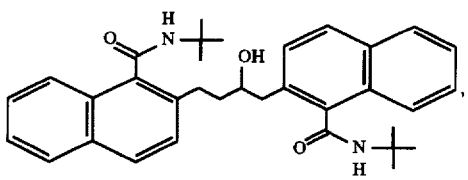
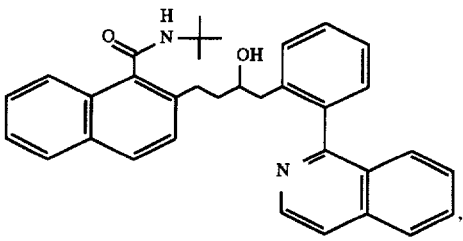
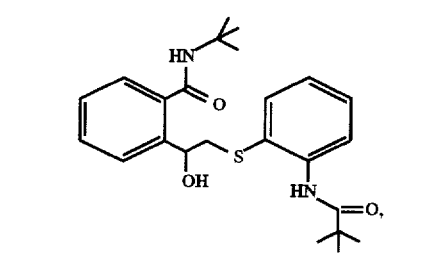
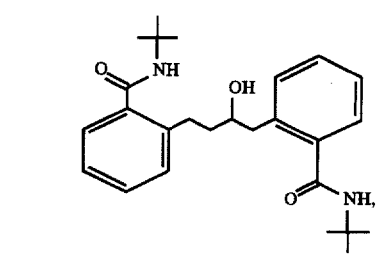
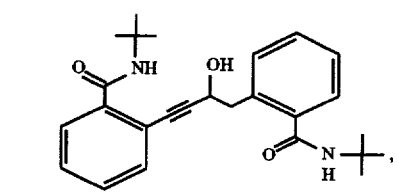
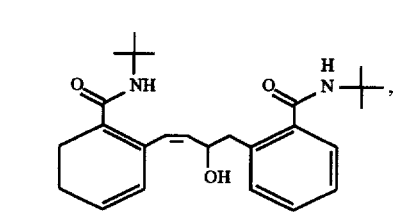
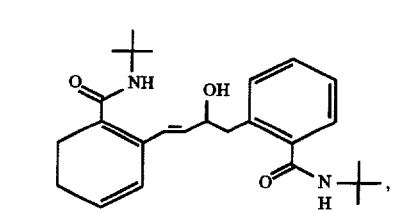

103
-continued
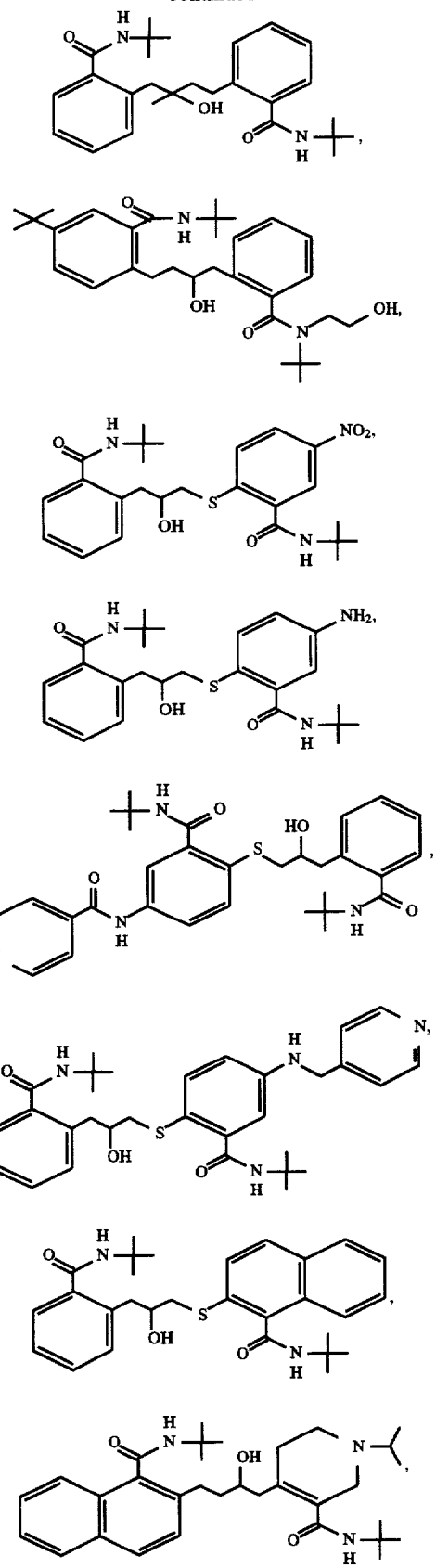
104
-continued
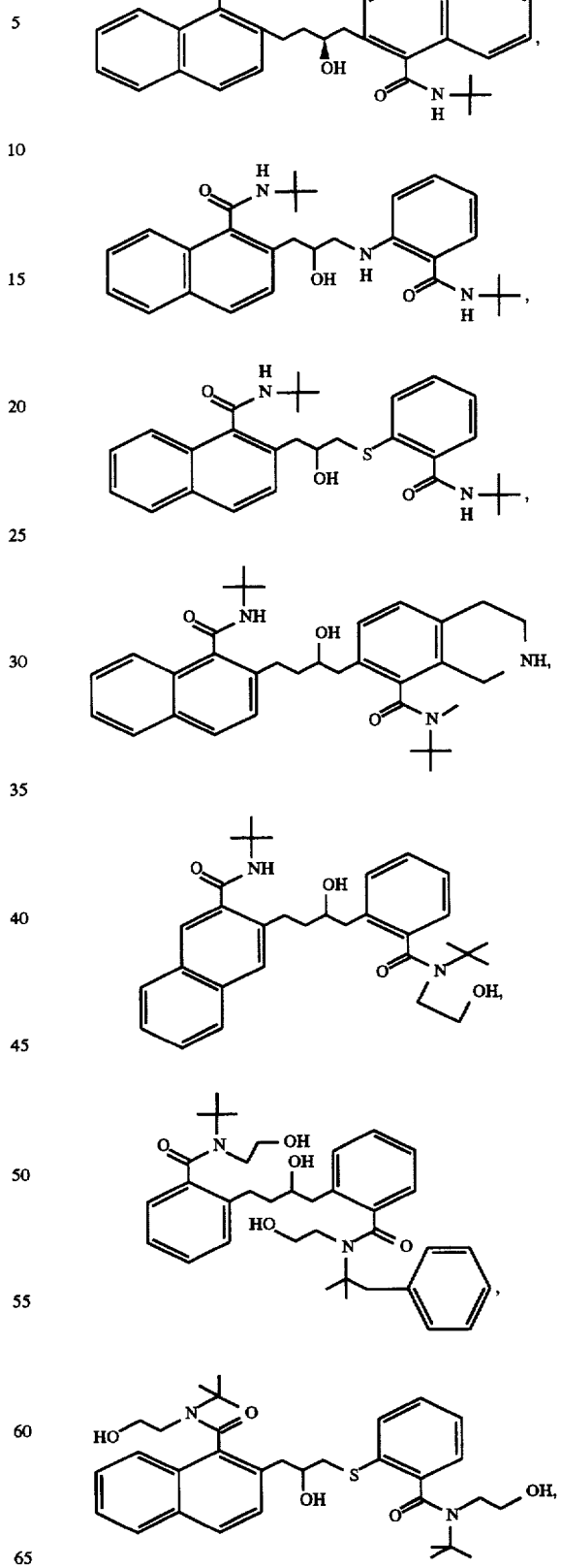

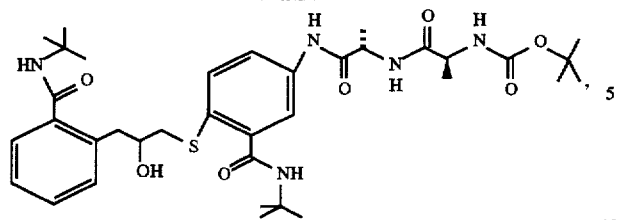
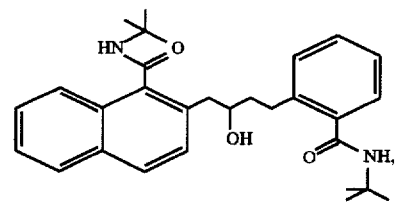
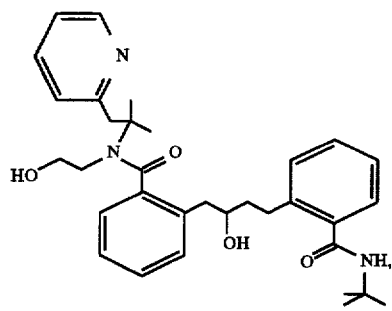
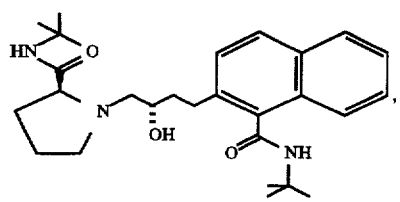
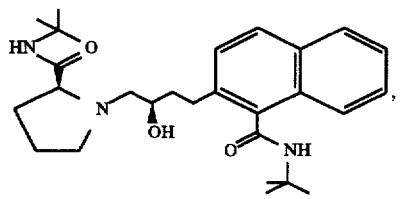
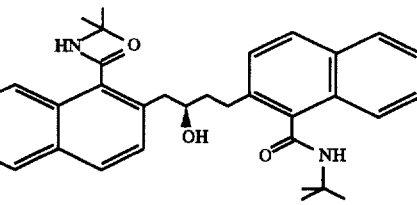
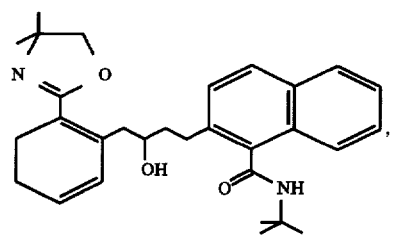
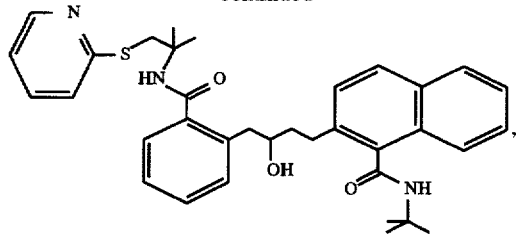
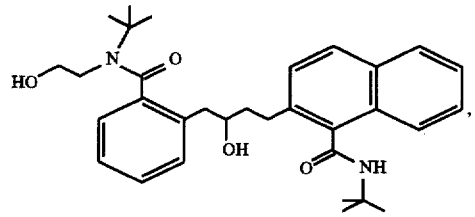
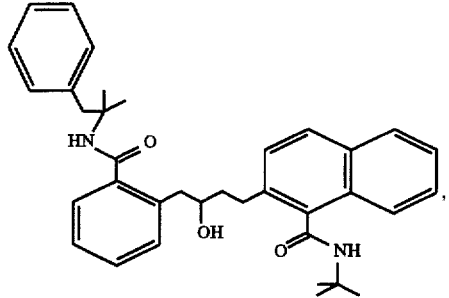
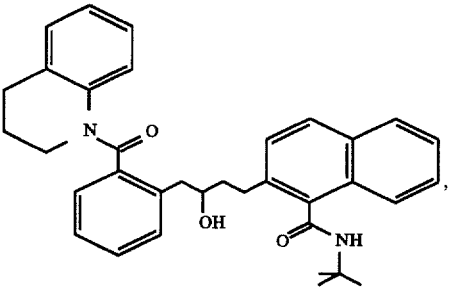
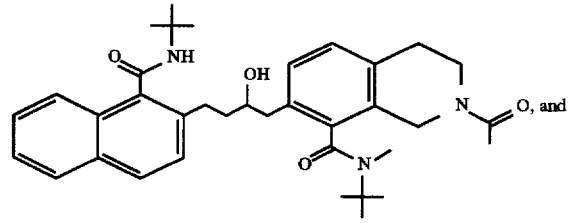
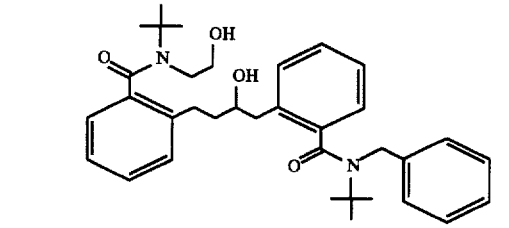
or a pharmaceutically acceptable salt thereof; and (2) a pharmaceutically acceptable carrier.

3. A method for preparing a compound of the formula XII

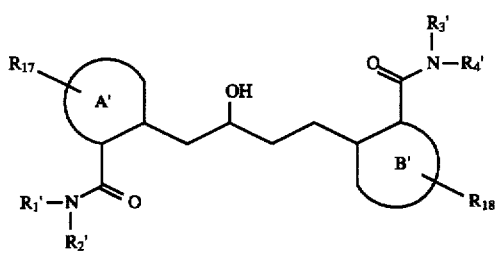

wherein:

A' and B' are individually selected from carbocyclic or heterocyclic, aromatic, saturated or partially saturated 5, 6 or 7 member rings which can be further substituted;

$R'_1$, $R'_2$, $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ or $R'_3$ and $R'_4$ can form a ring with the nitrogen atom to which they are attached provided that if $R'_1$, $R'_2$, $R'_3$ and $R'_4$ are individually selected from alkyl, cycloalkyl, aryl, and substituted alkyl, cycloalkyl or aryl, or $R'_1$ and $R'_2$ or $R'_3$ and $R'_4$ form a ring with the nitrogen atom to which they are attached, then at least one of $R'_1$, $R'_2$, $R'_3$ and $R'_4$ must be hydrogen;

$R_{17}$ and $R_{18}$ are individually selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{17}$ can form a fused ring structure with A' and $R_{18}$ can form a fused ring structure with B';

which method comprises carrying out the following reactions:

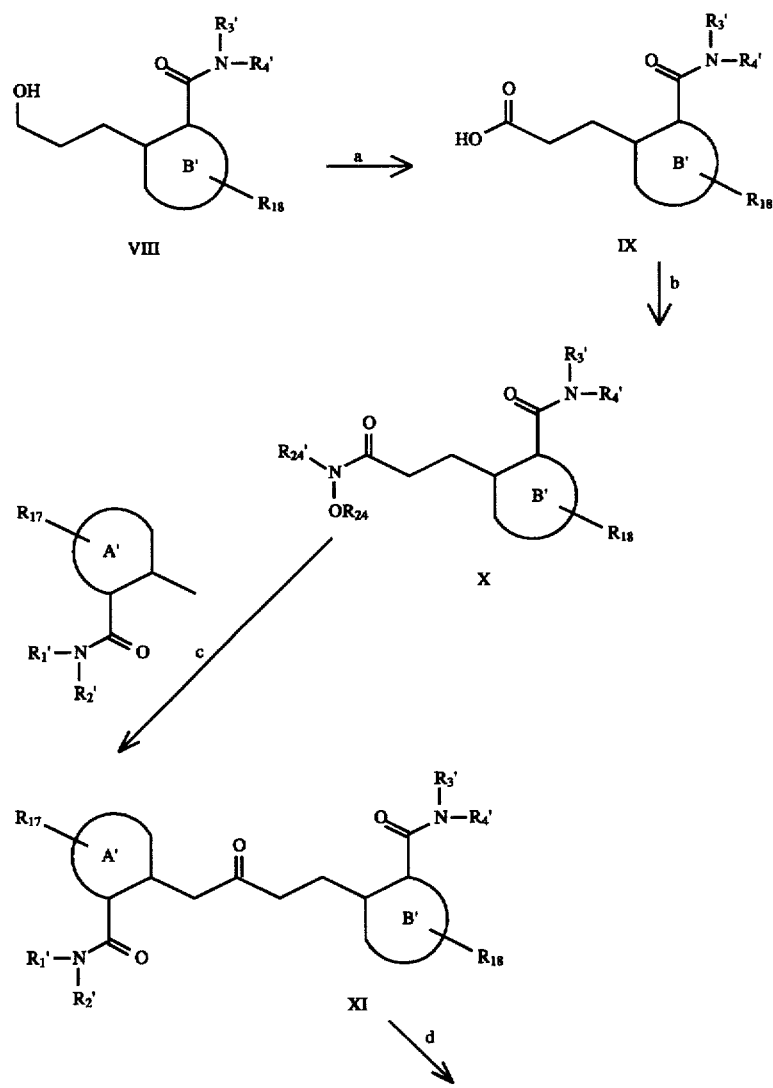

-continued

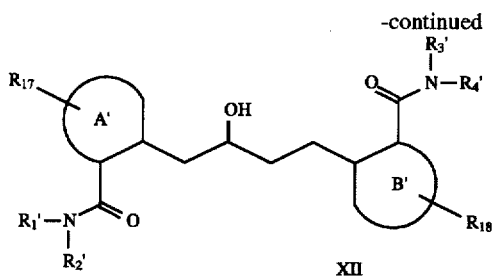

XII wherein:
a) the compound of the formula VIII is oxidized to obtain the compound of the formula IX;
b) the compound of the formula IX is reacted with the compound $HN(OR_{24})R'_{24}$ to obtain the compound of the formula X, wherein $R_{24}$ and $R'_{24}$ are individually selected from alkyl groups;
c) the compound of the formula X is reacted with the compound of the formula Xa to obtain the compound of the formula XI; and
d) the compound of the formula XI is reduced to obtain the compound of the formula XII.

4. The method of claim 3, further comprising the step of converting the compound of formula XII to a pharmaceutically acceptable salt thereof.

5. The method of claim 3, wherein in step a), the oxidation is accomplished using chromic oxide or pyridinium dichromate.

6. The method of claim 3, wherein in step b), the alkyl alkoxyamine is alkyl alkoxylamine hydrochloride.

7. The method of claim 6, wherein said alkyl alkoxylamine hydrochloride is N-methyl methoxy amine hydrochloride.

8. The method of claim 3, wherein in step c), the compound of the formula Xa is reacted with an alkyl lithium, followed by reaction with the compound of the formula X to obtain the compound of the formula XI.

9. The method of claim 8, wherein said alkyl lithium is s-butyl lithium.

10. The method of claim 3, wherein in step d), the reduction is accomplished using sodium borohydride.

11. The method of claim 3, wherein one or more of $R'_1$, $R'_2$, $R'_3$, and $R'_4$ is alkyl substituted with a protected hydroxyl group, and further comprising, after the reduction step d), carrying out the step e) of deprotecting said one or more of $R'_1$, $R'_2$, $R'_3$, and $R'_4$ alkyl groups substituted with a protected hydroxyl group.

12. The method of claim 11, wherein said deprotecting step e) is carried out using tetrabutyl ammonium fluoride.

* * * * *

UNITED STATES PATENT AND TRADEMARK OFFICE
CERTIFICATE OF CORRECTION

PATENT NO. : 5,714,518  Page 1 of 5
DATED : February 3, 1998
INVENTOR(S) : Reich et al.

It is certified that error appears in the above-identified patent and that said Letters Patent is hereby corrected as shown below:

In claim 1, col. 96, fifth formula down,

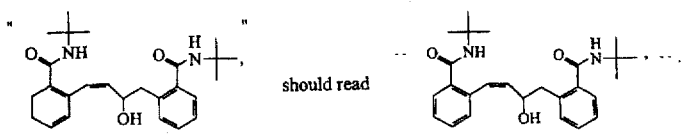

In claim 1, col. 97, first formula,

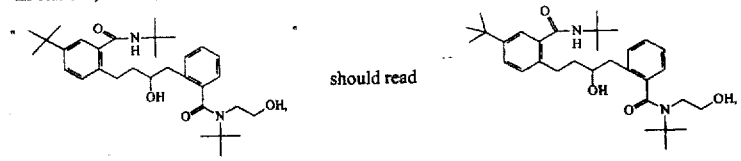

UNITED STATES PATENT AND TRADEMARK OFFICE
CERTIFICATE OF CORRECTION

PATENT NO. : 5,714,518

DATED : February 3, 1998

INVENTOR(S) : Reich et al.

Page 2 of 5

It is certified that error appears in the above-identified patent and that said Letters Patent is hereby corrected as shown below:

In claim 1, col. 97, eighth formula down,

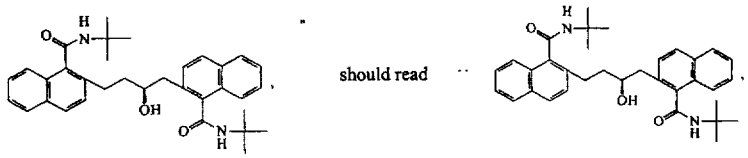

In claim 2, col. 100, line 55, "comprise" should read -- comprises --.

In claim 2, col. 102, sixth formula down,

UNITED STATES PATENT AND TRADEMARK OFFICE
CERTIFICATE OF CORRECTION

PATENT NO. : 5,714,518
DATED : February 3, 1998
INVENTOR(S) : Reich et al.

It is certified that error appears in the above-identified patent and that said Letters Patent is hereby corrected as shown below:

In claim 2, col. 103, second formula down,

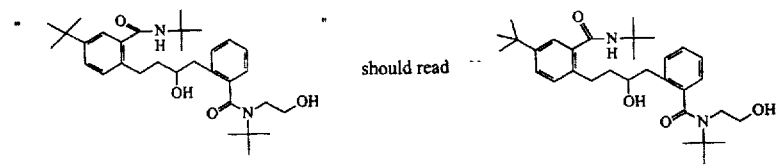

In claim 2, col. 104, first formula,

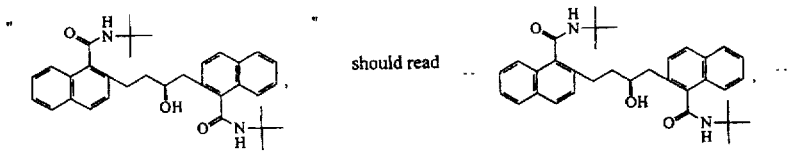

UNITED STATES PATENT AND TRADEMARK OFFICE
CERTIFICATE OF CORRECTION

PATENT NO. : 5,714,518

DATED : February 3, 1998

INVENTOR(S) : Reich et al.

It is certified that error appears in the above-identified patent and that said Letters Patent is hereby corrected as shown below:

In claim 2, col. 105, fourth formula down,

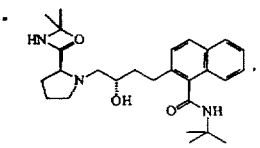   should read   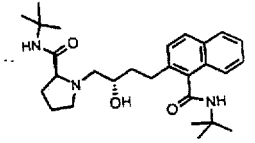

In claim 2, col. 105, fifth formula down,

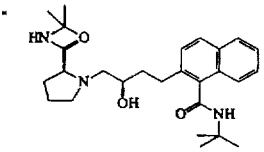   should read   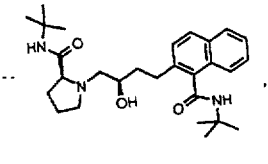

UNITED STATES PATENT AND TRADEMARK OFFICE
CERTIFICATE OF CORRECTION

PATENT NO. : 5,714,518
DATED : February 3, 1998
INVENTOR(S) : Reich et al.

It is certified that error appears in the above-identified patent and that said Letters Patent is hereby corrected as shown below:

In claim 2, col. 105, sixth formula down,

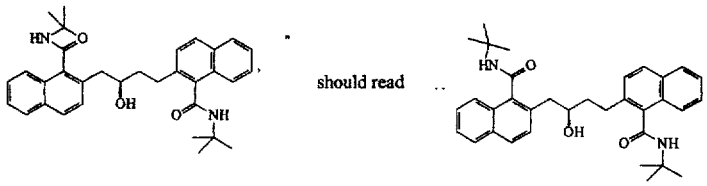

In claim 3, col. 107, second formula from the bottom,

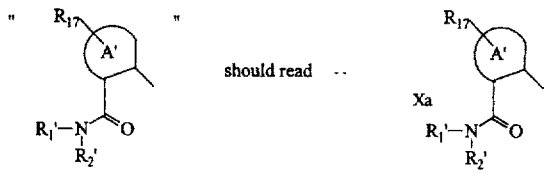

In claim 11, col. 110, line 24, after "R'$_1$", insert -- , --.

Signed and Sealed this

First Day of June, 1999

Q. TODD DICKINSON

Attest:

Attesting Officer

Acting Commissioner of Patents and Trademarks